US012606556B2

(12) United States Patent
Wang et al.

(10) Patent No.: US 12,606,556 B2
(45) Date of Patent: Apr. 21, 2026

(54) TYK-2 INHIBITOR

(71) Applicant: BEIGENE, LTD., Grand Cayman (KY)

(72) Inventors: Qiuwen Wang, Beijing (CN); Yunhang Guo, Beijing (CN); Zhiwei Wang, Beijing (CN)

(73) Assignee: BeOne Medicines I GmbH, Basel (CH)

( * ) Notice: Subject to any disclaimer, the term of this patent is extended or adjusted under 35 U.S.C. 154(b) by 873 days.

(21) Appl. No.: 17/801,551

(22) PCT Filed: Feb. 25, 2021

(86) PCT No.: PCT/CN2021/077936

§ 371 (c)(1),
(2) Date: Aug. 23, 2022

(87) PCT Pub. No.: WO2021/170046

PCT Pub. Date: Sep. 2, 2021

(65) Prior Publication Data

US 2023/0159520 A1 May 25, 2023

(30) Foreign Application Priority Data

Feb. 26, 2020 (WO) ................ PCT/CN2020/076690

(51) Int. Cl.

| | |
|---|---|
| ***C07D 471/04*** | (2006.01) |
| ***C07D 403/12*** | (2006.01) |
| ***C07D 413/12*** | (2006.01) |
| ***C07F 9/6561*** | (2006.01) |

(52) U.S. Cl.

CPC ......... *C07D 471/04* (2013.01); *C07D 403/12* (2013.01); *C07D 413/12* (2013.01); *C07F 9/6561* (2013.01); *C07B 2200/05* (2013.01)

(58) Field of Classification Search

CPC .................................................... C07D 471/04

See application file for complete search history.

(56) References Cited

U.S. PATENT DOCUMENTS

| | | | |
|---|---|---|---|
| 10,508,113 | B2 | 12/2019 | Argiriadi |
| 2019/0276450 | A1 | 9/2019 | Argiriadi |

FOREIGN PATENT DOCUMENTS

| | | | |
|---|---|---|---|
| JP | 6557436 | B1 | 8/2019 |
| WO | 2012117059 | A1 | 9/2012 |
| WO | 2013171690 | | 11/2013 |
| WO | 2013171690 | A1 | 11/2013 |
| WO | 2013192049 | | 12/2013 |
| WO | 2013192049 | A2 | 12/2013 |
| WO | 2014074661 | | 5/2014 |
| WO | 2018071794 | A1 | 4/2018 |
| WO | 2018183649 | | 10/2018 |
| WO | 2018183656 | A1 | 10/2018 |
| WO | 2019178079 | A1 | 9/2019 |
| WO | 2019178079 | A9 | 12/2019 |
| WO | 2019232138 | A1 | 12/2019 |
| WO | 2020086616 | A1 | 4/2020 |
| WO | 2021170046 | A1 | 9/2021 |
| WO | 2021259208 | A1 | 12/2021 |

OTHER PUBLICATIONS

Bryan et al., "Kinase Inhibitors for the Treatment of Immunological Disorders: Recent Advances", J Med. Chem., 61:9030-9058, 2018.

He et al., "Efficacy and Safety of Tofacitinib in the Treatment of Rheumatoid Arthritis: A Systematic Review and Meta-Analysis", BMC Musculoskelet Disorders, 14:12 pages, 2013.

International Preliminary Report on Patentability in PCT/CN2021/077936, dated Aug. 30, 2022, 5 pages.

International Preliminary Report on Patentability in PCT/CN2021/101282, dated Dec. 13, 2022, 8 pages.

International Search Report and Written Opinion in PCT/CN2021/077936, dated May 25, 2021, 10 pages.

International Search Report in PCT/CN2021/101282 dated Sep. 18, 2021, 4 pages.

Ishizaki et al., "Involvement of Tyrosine Kinase-2 in Both the IL-12/TH1 and IL-23/TH17 Axes in vivo", J. Immunol., 187:181-189, 2011.

Lochmuller, C. H. et al., "Chromatographic resolution of enantiomers," Journal of Chromatography, 113:283-302, 1975.

Minegishi et al., "Human tyrosine kinase 2 deficiency reveals its requisite roles in multiple cytokine signals involved in innate acquired immunity", Immunity, 25:745-755, 2006.

Neubauer et al., "JAK2 deficiency defines an essential developmental checkpoint in definitive hematopoiesis", Cell, 93:397-409, 1998.

Oyamada et al., "Tyrosine kinase 2 plays critical roles in the pathogenic CD4 T cell responses for the development of experimental autoimmune encephalomyelitis", J. Immunol., 183:7539-7546, 2009.

Prchal-Murphyl et al., "TYK2 kinase activity is required for functional type I interferon responses in vivo", PloS one, 7 (12 pages), 2012.

Wollenhaupt et al., "Safety and efficacy of tofacitinib, an oral Janus Kinase Inhibitor, for the treatment of rheumatoid arthritis in open-label", J. Rheumatol., 41:837-852, 2014.

Zerbini et al., "Tofacitinib for the treatment of rheumatoid arthritis", Expert Rev Clin. Immunol., 8:319-331, 2012. Abstract only.

*Primary Examiner* — Brian E Mcdowell

(74) *Attorney, Agent, or Firm* — McNeill PLLC

(57) ABSTRACT

Disclosed herein is a compound of Formula (I) for inhibiting TYK2 and treating disease associated with undesirable tyk-2 activity (tyk-2 related diseases), a method of using the compounds disclosed herein for treating inflammatory or autoimmune disease, and a pharmaceutical composition comprising the same.

17 Claims, No Drawings

TYK-2 INHIBITOR

CROSS-REFERENCE TO RELATED APPLICATIONS

This application is a U.S. National Stage Application under 35 U.S.C. § 371 of International Application No. PCT/CN2021/077936, filed Feb. 25, 2021, which claims priority to Patent Application No. PCT/CN2020/076690 (CN), filed on Feb. 26, 2020.

FIELD OF THE DISCLOSURE

Disclosed herein is a compound of Formula (I) for inhibiting TYK2 and treating disease associated with undesirable tyk-2 activity (tyk-2 related diseases), a method of using the compounds disclosed herein for treating inflammatory or autoimmune diseases, and a pharmaceutical composition comprising the same.

BACKGROUND OF THE DISCLOSURE

Janus family of kinases includes JAK1, JAK2, JAK3 and tyrosine kinase 2 (Tyk2) and are nonreceptor tyrosine kinases that bind to the intracellular portion of cell surface cytokine receptors. In response to the stimulation of these receptors, the Janus kinases phosphorylate signal transducer and activator of transcription (STAT) proteins, which then dimerize, translocate to the nucleus, and activate gene transcription. Tyrosine kinase 2 (Tyk2) is a member of the Janus kinase (JAK)family of nonreceptor tyrosine kinases and has been shown to be critical in regulating the signal transduction cascade downstream of receptors for IL-12, IL-23 and type I interferons in both mice (Ishizaki, M. et al., "Involvement of Tyrosine Kinase-2 in Both the IL-12/TH1 and IL-23/TH17 Axes in vivo", *J. Immunol.,* 187: 181-189 (2011); Prchal-Murphyl, M. et al., "TYK2 kinase activity is required for functional type I interferon responses in vivo", *PloS one,* 7:e39141 (2012)) and humans (Minegishi, Y et al., "Human tyrosine kinase 2 deficiency reveals its requisite roles in multiple cytokine signals involved in innate acquired immunity", *Immunity,* 25:745-755 (2006)). Tyk2 mediates the receptor-induced phosphorylation of members of the STAT family of transcription factors, an essential signal that leads to the dimerization of STAT proteins and the transcription of STAT-dependent pro-inflammatory genes. Tyk2-deficient mice are resistant to experimental model of colitis, psoriasis and multiple sclerosis, demonstrating the important of Tyk2-mediated signaling in autoimmunity and related disorders (Ishizaki, M. et al., "Involvement of Tyrosine Kinase-2 in Both the IL-12/TH1 and IL-23/TH17 Axes in vivo", *J. Immunol.,* 187: 181-189 (2011); Oyamada, A. et al., "Tyrosine kinase 2 plays critical roles in the pathogenic CD4 T cell responses for the development of experimental autoimmune encephalomyelitis", *J. Immunol.,* 2009, 183, 7539-7546).

To date, most of known small molecule JAK inhibitors that have progressed into development are active site-directed inhibitors that bind to the adenosine triphosphate (ATP) site of the catalytic domain (also referred to as the JH1 or "Janus Homology 1" domain) of the JAK protein, which prevents catalytic activity of the kinase by blocking ATP, downstream phosphorylation, and resulting pathway signal transduction (Bryan, M. et al., "Kinase Inhibitors for the Treatment of Immunological Disorders: Recent Advances", *J. Med. Chem.* 2018, 61, 9030-9058). It's well-known that JAK2 is involved in hematopoiesis (Neubauer, H.; et al., "JAK2 deficiency defines an essential developmental checkpoint in definitive hematopoiesis", *Cell* 1998, 93, 397-409) and the inhibition of JAK2 can cause side effects such as anemia, neutropenia, and increased infection risk and dyslipidemia (Wollenhaupt, J., et al., "Safety and efficacy of tofacitinib, an oral Janus Kinase Inhibitor, for the treatment of rheumatoid arthritis in open-label. *J. Rheumatol.* 2014, 41, 837-852; He, Y, et al., Efficacy and safety of tofacitinib in the treatment of rheumatoid arthritis: a systematic review and meta-analysis. *BMC Musculoskelet. Disord.* 2013, 14, 298; Zerbini, C. A, et al., Tofacitinib for the treatment of rheumatoid arthritis. *Expert Rev. Clin. Immunol.* 2012, 8, 319-331).

Small molecule inhibitors of TYK2-JH2 domain are being developed for treating autoimmune diseases. BMS986165 (WO2014074661A1, WO2018183649A1, WO2018183656A1 and WO2019232138A1) is a first-in-class of TYK2-JH2 inhibitor, currently undergoing multiple clinical trials in psoriasis, ulcerative colitis (UC), lupus and systemic lupus erythematosus. The other TYK2-JH2 inhibitor entered clinical trials is ABBV-712 (See, for example, WO2019178079A1, WO2019178079A9, JP6557436B1 and US2019276450A1) and it is in clinical trial for psoriasis.

In this patent, compounds bind to the pseudokinase (JH2) domain of TYK2 and inhibit its function through an allosteric mechanism. In the meanwhile, these compounds have greatly improved selectivity over other JAK family members (JAK1, JAK2 and JAK3).

SUMMARY OF THE DISCLOSURE

Disclosed herein provides a serial of compound which inhibit the pseudokinase (JH2) domain of TYK2. These compounds showed picomolar to nanomolar biochemical activity in TYK2-JH2 binding assay and also showed nanomolar activity in cellular assay. In the meanwhile, these compounds showed excellent selectivity in TYK2 biochemical/cellular assay against JAK1.

In first aspect, disclosed herein provides a compound having the following Formula (I):

(I)

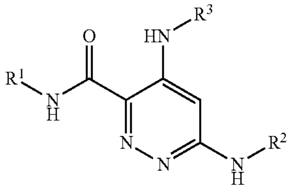

or a stereoisomer or pharmaceutically acceptable salt thereof, wherein:

- $R^1$ is hydrogen, $C_{1-6}$alkyl or $C_{3-6}$cycloalkyl, wherein said $C_{1-6}$alkyl and $C_{3-6}$cycloalkyl are each optionally substituted with 0-7 $R^{1a}$;
- $R^{1a}$ at each occurrence is independently hydrogen, deuterium, halogen, —CN or —OMe;
- $R^2$ is —C(O)$R^{2a}$ or a 4-10 membered heterocyclyl containing 1-2 heteroatoms selected from nitrogen, oxygen or sulfur, wherein said 4-10 membered heterocyclyl is optionally substituted with 0-4 $R^{2b}$;
- $R^{2a}$ is independently $C_{1-6}$alkyl or $C_{3-6}$cycloalkyl;
- $R^{2b}$ at each occurrence is independently hydrogen, =O, halo, —CN, $—(CH_2)_r—C_{3-6}$cycloalkyl, or a $—(CH_2)_r$-3-10 membered heterocyclyl comprising carbon atoms and 1-4 heteroatoms selected from nitrogen, oxygen or sulfur, wherein said —$(CH_2)_r$—$C_{3-6}$cycloalkyl and —$(CH_2)_r$-3-10 membered heterocyclyl are each optionally substituted with 0-2 $R^{2c}$;

$R^{2c}$ at each occurrence is independently hydrogen, -haloC$_{1-3}$alkyl or —$C_{1-3}$alkyl;

$R^3$ is

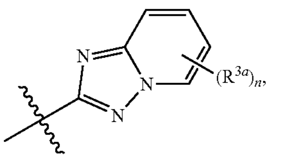

wherein n is an integer selected from 0, 1, 2, 3 and 4; and $R^{3a}$ at each occurrence is independently hydrogen, halogen, —CN, —$C_{1-6}$alkyl, —$C_{1-6}$alkoxyl, —P(O)$R^{3d}R^{3e}$, -$(L^1)_r$-CyA; or CyA, wherein said —$C_{1-6}$alkyl, and —$C_{1-6}$alkoxyl are each optionally substituted with 0-3 $R^{3d}$;

$L^1$ at each occurrence is independently —O—, —S—, —C(O)—, —NH—, —$CH_2$— or —NHC(O)—;

CyA is $C_{3-10}$ cycloalkyl, 3-10 membered heterocyclyl comprising carbon atoms and 1-4 heteroatoms selected from nitrogen, oxygen or sulfur, 6-10 membered aryl, or 4-10 membered heteroaryl comprising carbon atoms and 1-4 heteroatoms selected from nitrogen, oxygen or sulfur, wherein said $C_{3-10}$ cycloalkyl, 3-10 membered heterocyclyl, 6-10 membered aryl and 4-10 membered heteroaryl are each substituted with 0-3 $R^{3b}$;

$R^{3b}$ at each occurrence is independently hydrogen, halogen, —$C_{1-6}$alkyl, -oxo-, —$OR^{3c}$, —C(O)$R^{3d}$, —S(O)$_2R^{3d}$, —$NR^{3d}R^{3e}$, $C_{3-10}$cycloalkyl, a 3-10 membered heterocyclyl containing 1-4 heteroatoms selected from nitrogen, oxygen or sulfur, a 6-10 membered aryl, or a 4-10 membered heteroaryl comprising carbon atoms and 1-4 heteroatoms selected from nitrogen, oxygen or sulfur; wherein said-$C_{1-6}$alkyl, $C_{3-10}$ cycloalkyl, 3-10 membered heterocyclyl, 6-10 membered aryl and 4-10 membered heteroaryl are each optionally substituted with 0-3 —$R^{3d}$;

$R^{3c}$ and $R^{3d}$ at each occurrence are independently hydrogen, halogen, —CN, hydroxyl, —$C_{1-6}$alkyl, —$C_{1-6}$alkoxy, a 5-6 membered aryl, a 3-6 membered heterocyclyl containing 1-2 heteroatoms selected from nitrogen, oxygen or sulfur, or a 5-6 membered heteroaryl comprising carbon atoms and 1-3 heteroatoms selected from nitrogen, oxygen or sulfur, wherein said —$C_{1-6}$alkyl, —$C_{1-6}$alkoxy, 5-6 membered aryl, 3-6 membered heterocyclyl, 5-6 membered heteroaryl are optionally substituted by -halogen, —CN, hydroxyl, —$C_{1-6}$alkyl, —$C_{1-6}$alkoxyl, $C_{1-6}$alkylamino, di$C_{1-6}$alkylamino, a 3-6 membered heterocyclyl, a 6-10 membered aryl or a 5-10 membered heteroaryl;

$R^{3e}$ at each occurrence is independently selected from —H, —$C_{1-6}$alkyl, —S(O)$_2R^{3f}$ or —C(O)$R^{3f}$, wherein $R^{3f}$ is independently $C_{1-6}$alkyl or $C_{3-6}$cycloalkyl; and r is an integer of 0, 1 or 2.

In one embodiment, $R^2$ is oxetanyl, thiazolyl, pyridyl, pyrimidinyl, pyridazinyl, pyrazinyl or quinolinyl, each of which is substituted with 0-3 $R^{2b}$.

In one embodiment, $R^2$ is —C(O)$R^{2a}$.

In one embodiment, R2 is selected from

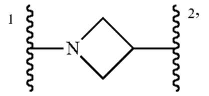 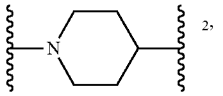

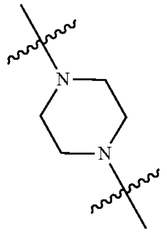, 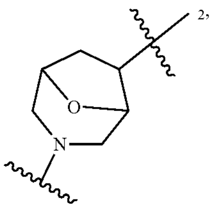

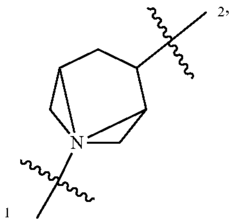 or 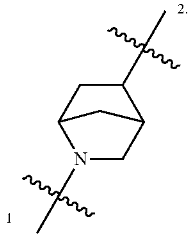

In one embodiment, $R^1$ is methyl, ethyl, propyl, isopropyl, isobutyl, cyclopropyl, cyclobutyl, cyclopentyl and cyclohexyl, each of which is optionally substituted with 0-3 $R^{1a}$.

In one embodiment, $R^1$ is methyl, or —$CD_3$.

In one embodiment, $R^3$ is

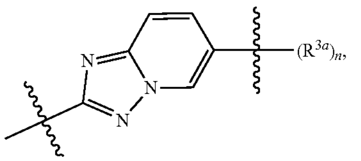

and $R^{3a}$ and n is defined as above.

In one embodiment, $R^{3a}$ is hydrogen, halogen, —CN, —$C_{1-6}$alkyl, —P(O)$R^{3d}R^{3e}$, -$(L^1)_{0-2}$-CyA or CyA, wherein CyA is a 3-6 membered heterocyclyl or heteroaryl comprising carbon atoms and 1-4 heteroatoms selected from nitrogen, oxygen or sulfur and optionally substituted with 0-3 $R^{3d}$.

In one embodiment, $L^1$ at each occurrence is independently —O—, —S—, —C(O)—, —NH—, —$CH_2$— or —NHC(O)—.

In one embodiment, $R^{3a}$ is 3-6 membered heterocyclyl or heteroaryl comprising carbon atoms and 1-4 heteroatoms selected from nitrogen, oxygen or sulfur.

In one embodiment, CyA is a 5-6 membered heterocyclyl comprising carbon atoms and 1-4 heteroatoms selected from nitrogen or oxygen.

In one embodiment, CyA is azetidinyl, piperidinyl and piperazinyl, each of which is substituted with 0-3 $R^{3b}$.

In one embodiment, CyA is a 7-10 membered bridged heterocyclyl comprising carbon atoms and 1-2 heteroatoms selected from N and O substituted with 0-3 $R^{3b}$.

In one embodiment, CyA is,

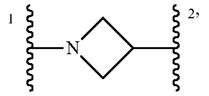 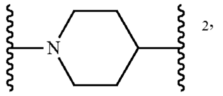

-continued

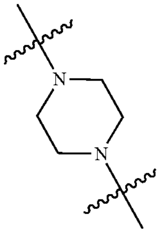

,

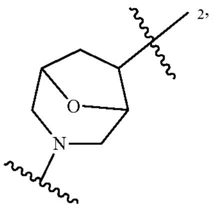

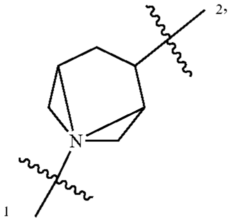

or

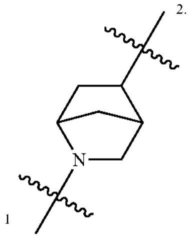

In one embodiment, the N heteroatom on CyA is attached to $R^3$.

In one embodiment, $R^{3b}$ is hydrogen, halogen, $—C_{1-3}$alkyl, $—OR^{3c}$, $—C(O)R^{3d}$ $NR^{3d}R^{3e}$, $C_{3-10}$cycloalkyl, wherein said $—C_{1-3}$alkyl and $C_{3-10}$cycloalkyl are optionally substituted with 0-3 $—R^{3d}$.

In one embodiment, $R^{3c}$ and $R^{3d}$ at each occurrence is independently selected from hydrogen, halogen, —CN, hydroxyl, $—C_{1-3}$alkyl, $—C_{1-3}$alkoxy, phenyl, a 3-6 membered heterocyclyl containing 1-2 heteroatoms selected from nitrogen, oxygen or sulfur, a 5-6 membered heteroaryl comprising carbon atoms and 1-3 heteroatoms selected from nitrogen, oxygen or sulfur, wherein said $—C_{1-6}$alkyl, $—C_{1-6}$alkoxy, phenyl, 3-6 membered heterocyclyl, 5-6 membered heteroaryl are optionally substituted by -halogen, —CN, hydroxyl, $—C_{1-3}$alkyl, $—C_{1-3}$alkoxyl, $C_{1-3}$alkylamino, di$C_{1-6}$alkylamino, a 3-6 membered heterocyclyl, a 6-10 membered aryl or a 5-10 membered heteroaryl.

In one embodiment, $R^{3b}$ is hydrogen, halogen, methyl, ethyl, propyl, isopropyl, isobutyl, methoxyl, cyclopropyl, cyclobutyl, cyclopentyl, cyclohexyl, $—OR_{3c}$, $NR_{3d}R_{3e}$, $C_{3-10}$cycloalkyl, wherein said $—C_{1-3}$alkyl and $C_{3-10}$cycloalkyl are optionally substituted with 0-3 $—R^{3d}$.

In one embodiment, $R^3$ is

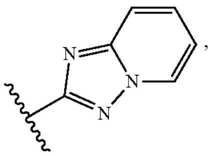

,

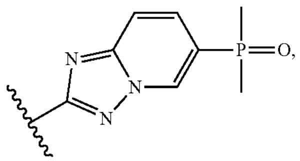

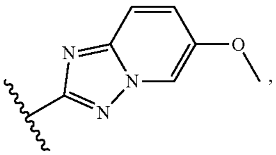

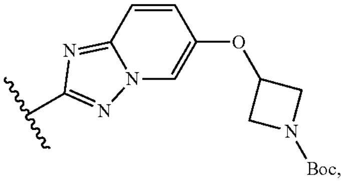

-continued

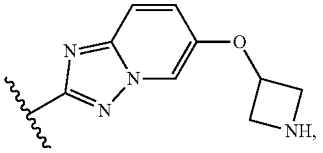

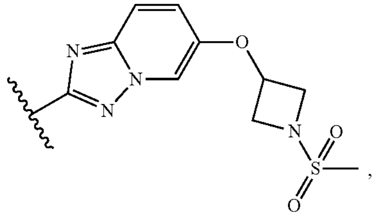

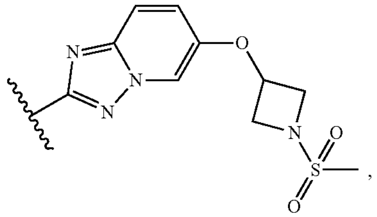

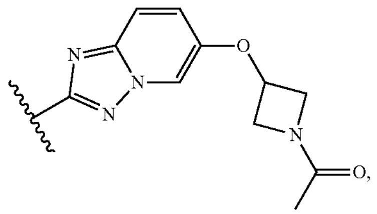

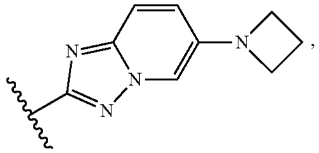

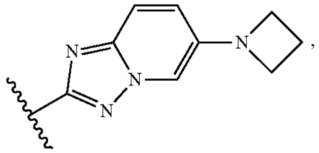

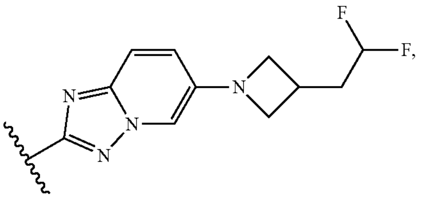

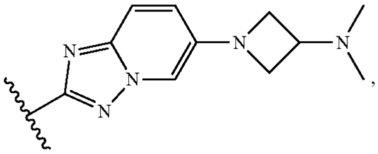

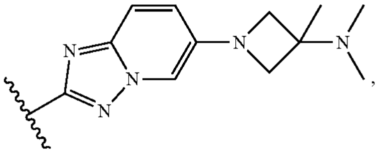

-continued
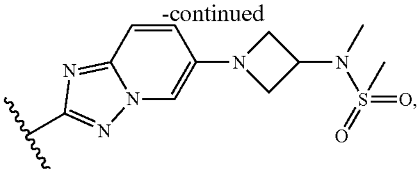
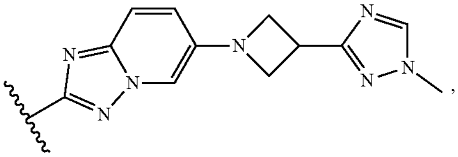
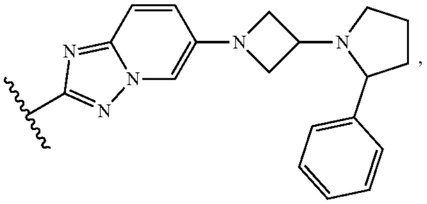
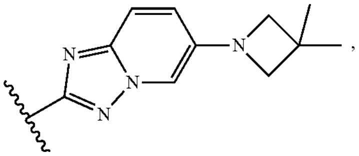
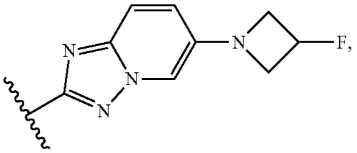
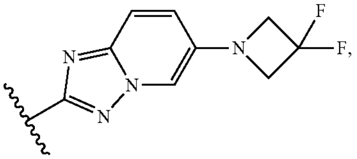
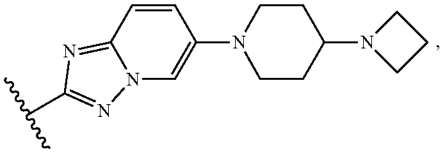
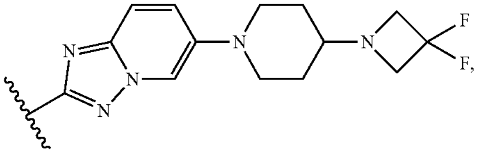
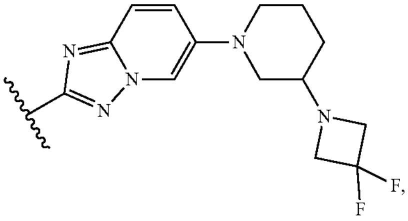
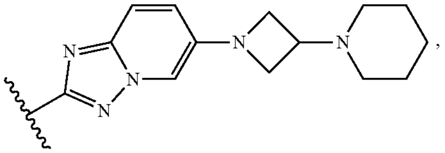
-continued
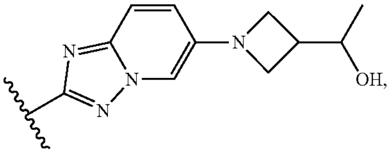
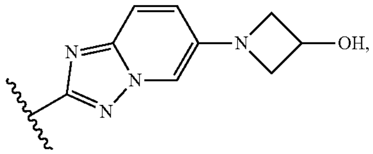
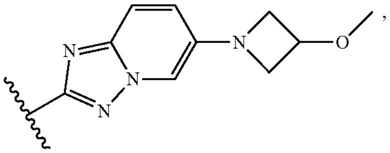
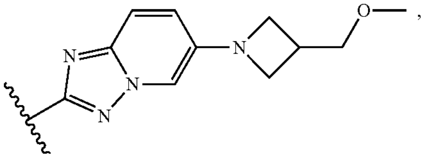
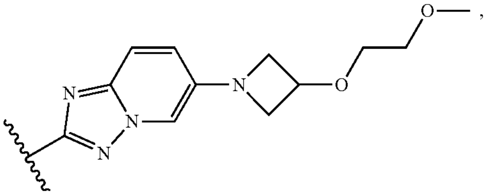
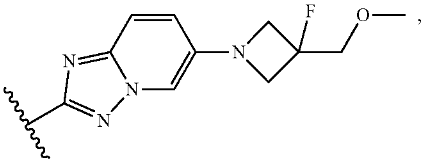
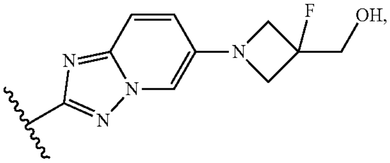
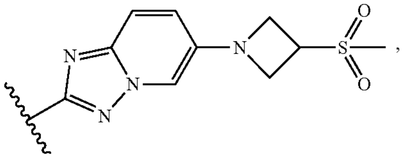
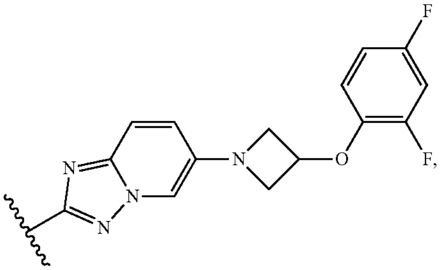

-continued
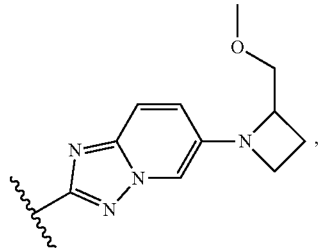
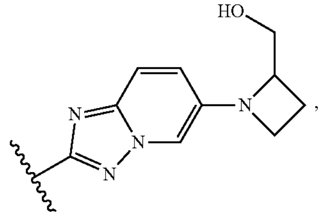
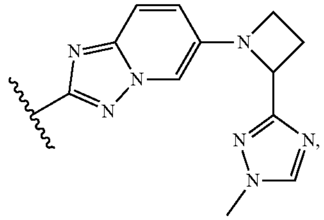
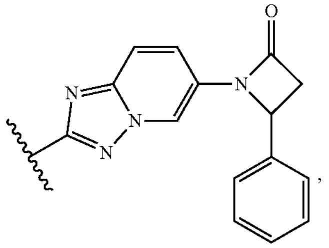
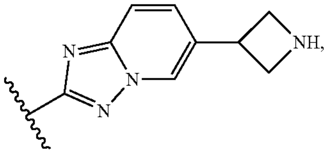
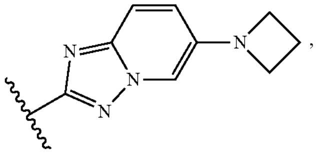
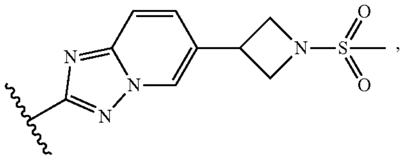
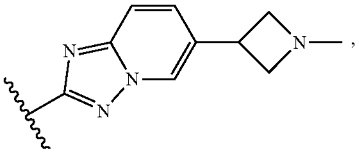
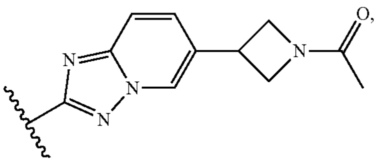
-continued
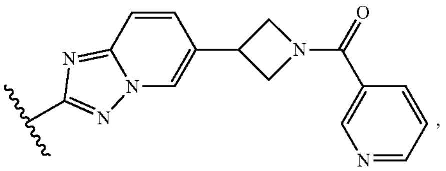
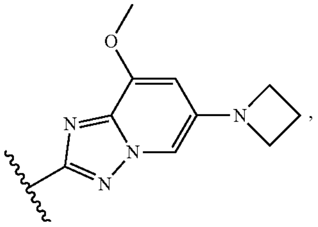
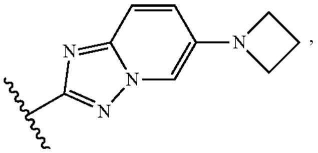
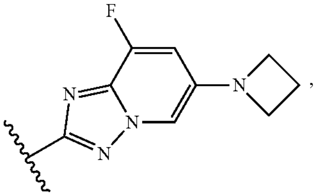
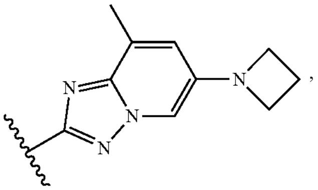
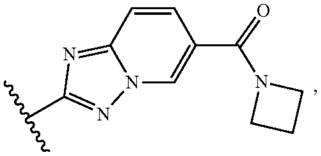
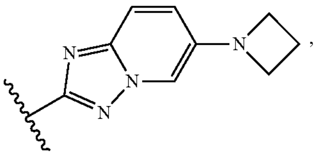
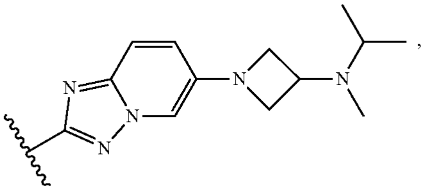
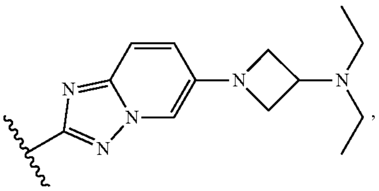

-continued
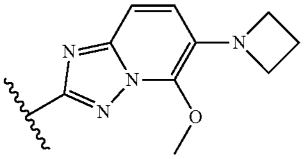
,
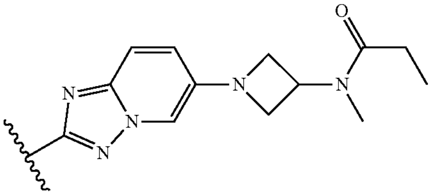
,
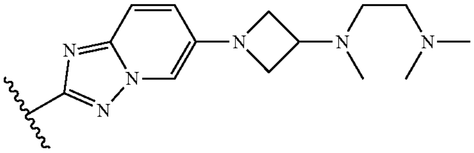
,
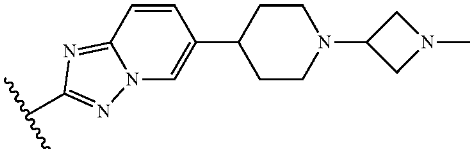
,
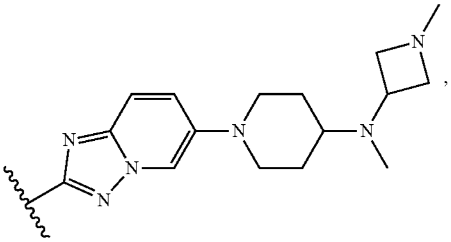
,
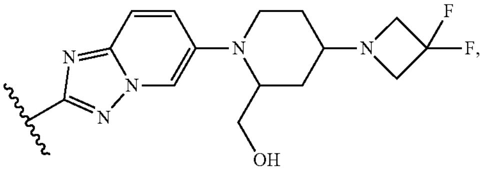
,
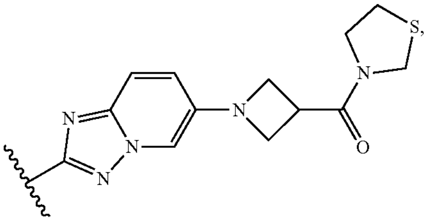
,
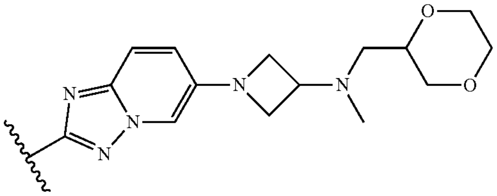
,
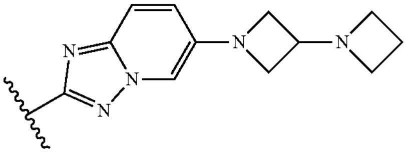
,
-continued
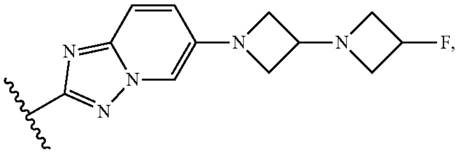
,
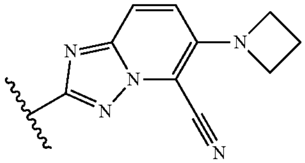
,
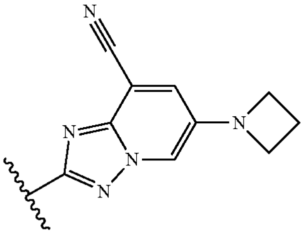
,
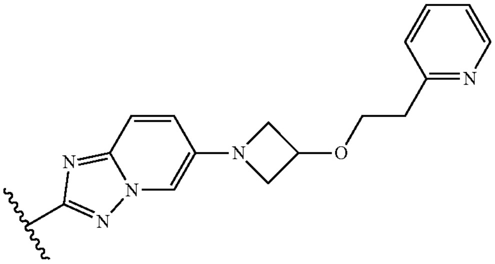
,
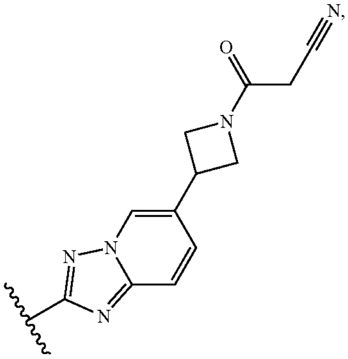
,
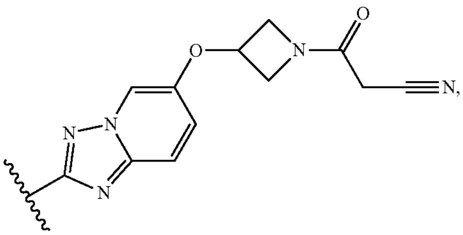
, -continued

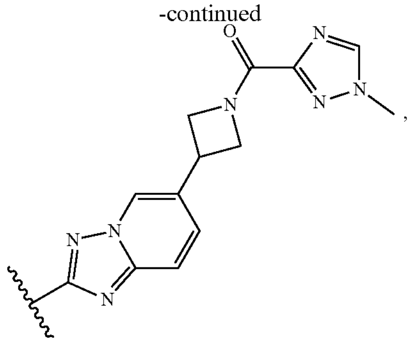

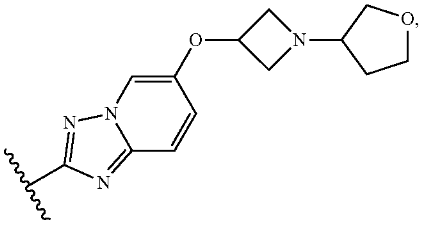

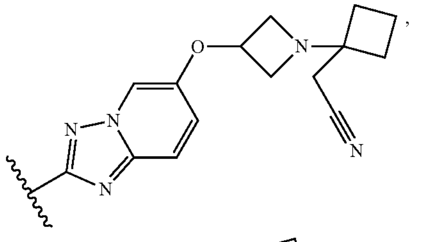

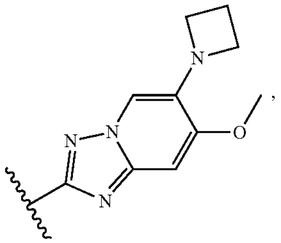

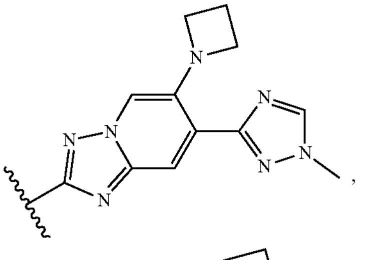

or

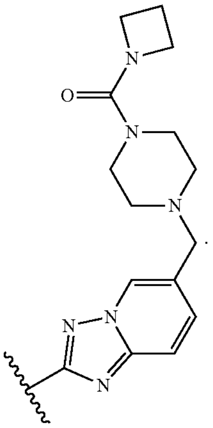

In one embodiment, the compound is selected from the exemplified compounds in Examples A4, A5, C1, C2, C3, C4, C5, D1, E1, E2, E3, E4, E5, E6, E7, E8, E9, E10, E11, E12, E13, E14, E15, E16, E17, E18, E19, E20, E21, E22, F1, G1, H1, J1, J2, K1, L1, L2, L3, L4, L5, M1, N2, N3, O1, P1, or Q1.

In second aspect, disclosed herein provides a pharmaceutical composition comprising one or more compounds in the present disclosure or a stereoisomer or pharmaceutically acceptable salt thereof, and a pharmaceutically acceptable excipient.

In third aspect, disclosed herein provides a method for treating disease associated with undesirable TYK2 activity (TYK2-related diseases), comprising administrating to a subject in need of such treatment a therapeutically effective amount of the compounds in the present disclosure or a stereoisomer or pharmaceutically acceptable salt thereof.

In one embodiment, the disease is an inflammatory or autoimmune disease.

DETAILED DESCRIPTION OF THE INVENTION

Definitions

The following terms have the indicated meanings throughout the specification:

As used herein, including the appended claims, the singular forms of words such as "a," "an," and "the," include their corresponding plural references unless the context clearly dictates otherwise.

The term "or" is used to mean, and is used interchangeably with, the term "and/or" unless the context clearly dictates otherwise.

The term "alkyl" refers to a hydrocarbon group selected from linear and branched saturated hydrocarbon groups comprising from 1 to 18, such as from 1 to 12, further such as from 1 to 10, more further such as from 1 to 8, or from 1 to 6, or from 1 to 4, carbon atoms. Examples of alkyl groups comprising from 1 to 6 carbon atoms (i.e., $C_{1-6}$ alkyl) include, but not limited to, methyl, ethyl, 1-propyl or n-propyl ("n-Pr"), 2-propyl or isopropyl ("i-Pr"), 1-butyl or n-butyl ("n-Bu"), 2-methyl-1-propyl or isobutyl ("i-Bu"), 1-methylpropyl or s-butyl ("s-Bu"), 1,1-dimethylethyl or t-butyl ("t-Bu"), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl and 3,3-dimethyl-2-butyl groups. The alkyl group can be optionally enriched in deuterium, e.g., $—CD_3$, $—CD_2CD_3$ and the like.

The term "halogen" refers to fluoro (F), chloro (Cl), bromo (Br) and iodo (I).

The term "haloalkyl" refers to an alkyl group in which one or more hydrogen is/are replaced by one or more halogen atoms such as fluoro, chloro, bromo, and iodo. Examples of the haloalkyl include halo$C_{1-8}$alkyl, halo$C_{1-6}$alkyl or halo $C_{1-4}$alkyl, but not limited to $—CF_3$, $—CH_2Cl$, $—CH_2CF_3$, $—CCl_2$, $CF_3$, and the like.

The term "alkyloxy" or "alkoxy" refers to an alkyl group as defined above attached to the parent molecular moiety through an oxygen atom. Examples of an alkyloxy, e.g., $C_{1-6}$alkyloxy or $C_{1-4}$ alkyloxy includes, but not limited to, methoxy, ethoxy, isopropoxy, propoxy, n-butoxy, tert-butoxy, pentoxy and hexoxy and the like.

The term "alkoxy-alkyl-" refers to an alkyl group as defined above further substituted with an alkoxy as defined above. Examples of an alkoxy-alkyl-, e.g., $C_{1-8}$alkoxy-$C_{1-}$ 8alkyl—or $C_{1-6}$alkoxy-$C_{1-6}$alkyl—includes, but not limited to, methoxymethyl, ethoxymethyl, ethoxyethyl, isopropoxymethyl, or propoxymethyl and the like.

The term "amino" refers to —$NH_2$. The term "alkylamino" refers to —NH(alkyl). The term "dialkylamino" refers to —$N(alkyl)_2$.

The term "alkenyl" herein refers to a hydrocarbon group selected from linear and branched hydrocarbon groups comprising at least one C═C double bond and from 2 to 18, such as from 2 to 8, further such as from 2 to 6, carbon atoms. Examples of the alkenyl group, e.g., $C_2$-6 alkenyl, include, but not limited to ethenyl or vinyl, prop-1-enyl, prop-2-enyl, 2-methylprop-1-enyl, but-1-enyl, but-2-enyl, but-3-enyl, buta-1,3-dienyl, 2-methylbuta-1,3-dienyl, hex-1-enyl, hex-2-enyl, hex-3-enyl, hex-4-enyl, and hexa-1,3-dienyl groups.

The term "alkynyl" herein refers to a hydrocarbon group selected from linear and branched hydrocarbon group, comprising at least one C≡C triple bond and from 2 to 18, such as 2 to 8, further such as from 2 to 6, carbon atoms. Examples of the alkynyl group, e.g., $C_2$-6 alkynyl, include, but not limited to ethynyl, 1-propynyl, 2-propynyl (propargyl), 1-butynyl, 2-butynyl, and 3-butynyl groups.

The term "cycloalkyl" refers to a hydrocarbon group selected from saturated cyclic hydrocarbon groups, comprising monocyclic and polycyclic (e.g., bicyclic and tricyclic) groups including fused, bridged or spiro cycloalkyl.

For example, the cycloalkyl group may comprise from 3 to 12, such as from 3 to 10, further such as 3 to 8, further such as 3 to 6, 3 to 5, or 3 to 4 carbon atoms. Even further for example, the cycloalkyl group may be selected from monocyclic group comprising from 3 to 12, such as from 3 to 10, further such as 3 to 8, 3 to 6 carbon atoms. Examples of the monocyclic cycloalkyl group include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, and cyclododecyl groups. In particular, Examples of the saturated monocyclic cycloalkyl group, e.g., $C_{3-8}$cycloalkyl, include, but not limited to cyclopropyl, cyclobutyl, cyclopentyl, cyclohexyl, cycloheptyl, and cyclooctyl groups. In a preferred embedment, the cycloalkyl is a monocyclic ring comprising 3 to 6 carbon atoms (abbreviated as $C_{3-6}$ cycloalkyl), including but not limited to, cyclopropyl, cyclobutyl, cyclopentyl, and cyclohexyl. Examples of the bicyclic cycloalkyl groups include those having from 7 to 12 ring atoms arranged as a fused bicyclic ring selected from [4,4], [4,5], [5,5], [5,6] and [6,6] ring systems, or as a bridged bicyclic ring selected from bicyclo[2.2.1]heptane, bicyclo[2.2.2]octane, and bicyclo[3.2.2]nonane. Further Examples of the bicyclic cycloalkyl groups include those arranged as a bicyclic ring selected from [5,6] and [6,6] ring systems.

The term "cycloalkenyl" refers to non-aromatic cyclic alkyl groups of from 3 to 10 carbon atoms having single or multiple rings and having at least one double bond and preferably from 1 to 2 double bonds. In one embodiment, the cycloalkenyl is cyclopentenyl or cyclohexenyl, preferably cyclohexenyl.

The term "cycloalkynyl" refers to non-aromatic cycloalkyl groups of from 5 to 10 carbon atoms having single or multiple rings and having at least one triple bond.

The term "deuterated" is used herein to modify a chemical structure or an organic group or radical, wherein one or more carbon-bound hydrogen(s) are replaced by one or more deuterium(s), e.g., "deuterated-alkyl", "deuterated-cycloalkyl", "deuterated-heterocycloalkyl", "deuterated-aryl", "deuterated-morpholinyl", and the like. For example, the term "deuterated-alkyl" defined above refers to an alkyl group as defined herein, wherein at least one hydrogen atom bound to carbon is replaced by a deuterium. In a deuterated alkyl group, at least one carbon atom is bound to a deuterium; and it is possible for a carbon atom to be bound to more than one deuterium; it is also possible that more than one carbon atom in the alkyl group is bound to a deuterium.

The term "aryl" used alone or in combination with other terms refers to a group selected from:

- 5- and 6-membered carbocyclic aromatic rings, e.g., phenyl;
- bicyclic ring systems such as 7 to 12 membered bicyclic ring systems, wherein at least one ring is carbocyclic and aromatic, e.g., naphthyl and indanyl; and,
- tricyclic ring systems such as 10 to 15 membered tricyclic ring systems wherein at least one ring is carbocyclic and aromatic, e.g., fluorenyl.

The terms "aromatic hydrocarbon ring" and "aryl" are used interchangeably throughout the disclosure herein. In some embodiments, a monocyclic or bicyclic aromatic hydrocarbon ring has 5 to 10 ring-forming carbon atoms (i.e., C5-10 aryl). Examples of a monocyclic or bicyclic aromatic hydrocarbon ring includes, but not limited to, phenyl, naphth-1-yl, naphth-2-yl, anthracenyl, phenanthrenyl, and the like. In some embodiments, the aromatic hydrocarbon ring is a naphthalene ring (naphth-1-yl or naphth-2-yl) or phenyl ring. In some embodiments, the aromatic hydrocarbon ring is a phenyl ring.

The term "heteroaryl" herein refers to a group selected from:

- 5-, 6- or 7-membered aromatic, monocyclic rings comprising at least one heteroatom, for example, from 1 to 4, or, in some embodiments, from 1 to 3, in some embodiments, from 1 to 2, heteroatoms, selected from nitrogen (N), sulfur (S) and oxygen (O), with the remaining ring atoms being carbon;
- 7- to 12-membered bicyclic rings comprising at least one heteroatom, for example, from 1 to 4, or, in some embodiments, from 1 to 3, or, in other embodiments, 1 or 2, heteroatoms, selected from nitrogen, oxygen or optionally oxidized sulfur as ring member(s), with the remaining ring atoms being carbon and wherein at least one ring is aromatic and at least one heteroatom is present in the aromatic ring; and
- 11- to 14-membered tricyclic rings comprising at least one heteroatom, for example, from 1 to 4, or in some embodiments, from 1 to 3, or, in other embodiments, 1 or 2, heteroatoms, selected from nitrogen, oxygen or optionally oxidized sulfur as ring member(s), with the remaining ring atoms being carbon and wherein at least one ring is aromatic and at least one heteroatom is present in an aromatic ring.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1. When the heteroaryl group contains more than one heteroatom ring member, the heteroatoms may be the same or different. The nitrogen atoms in the ring(s) of the heteroaryl group can be oxidized to form N-oxides.

The term "optionally oxidized sulfur" used herein refer to S, SO or SO2.

The terms "aromatic heterocyclic ring" and "heteroaryl" are used interchangeably throughout the disclosure herein.

In some embodiments, a monocyclic or bicyclic aromatic heterocyclic ring has 5-, 6-, 7-, 8-, 9- or 10-ring forming members with 1, 2, 3, or 4 heteroatom ring members independently selected from nitrogen (N), sulfur (S) and oxygen (O) and the remaining ring members being carbon. In some embodiments, the monocyclic or bicyclic aromatic heterocyclic ring is a monocyclic or bicyclic ring comprising 1 or 2 heteroatom ring members independently selected from nitrogen (N), sulfur (S) and oxygen (O). In some embodiments, the monocyclic or bicyclic aromatic heterocyclic ring is a 5- to 6-membered heteroaryl ring, which is monocyclic and which has 1 or 2 heteroatom ring members independently selected from nitrogen (N), sulfur (S) and oxygen (O). In some embodiments, the monocyclic or bicyclic aromatic heterocyclic ring is a 8- to 10-membered heteroaryl ring, which is bicyclic and which has 1 or 2 heteroatom ring members independently selected from nitrogen, sulfur and oxygen.

Examples of the heteroaryl group or the monocyclic or bicyclic aromatic heterocyclic ring include, but are not limited to, (as numbered from the linkage position assigned priority 1) pyridyl (such as 2-pyridyl, 3-pyridyl, or 4-pyridyl), cinnolinyl, pyrazinyl, 2,4-pyrimidinyl, 3,5-pyrimidinyl, 2,4-imidazolyl, imidazopyridinyl, isoxazolyl, oxazolyl, thiazolyl, isothiazolyl, thiadiazolyl (such as 1,2,3-thiadiazolyl, 1,2,4-thiadiazolyl, or 1,3,4-thiadiazolyl), tetrazolyl, thienyl (such as thien-2-yl, thien-3-yl), triazinyl, benzothienyl, furyl or furanyl, benzofuryl, benzoimidazolyl, indolyl, isoindolyl, indolinyl, oxadiazolyl (such as 1,2,3-oxadiazolyl, 1,2,4-oxadiazolyl, or 1,3,4-oxadiazolyl), phthalazinyl, pyrazinyl, pyridazinyl, pyrrolyl, triazolyl (such as 1,2,3-triazolyl, 1,2,4-triazolyl, or 1,3,4-triazolyl), quinolinyl, isoquinolinyl, pyrazolyl, pyrrolopyridinyl (such as 1H-pyrrolo[2,3-b]pyridin-5-yl), pyrazolopyridinyl (such as 1H-pyrazolo[3,4-b]pyridin-5-yl), benzoxazolyl (such as benzo[d]oxazol-6-yl), pteridinyl, purinyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, furazanyl (such as furazan-2-yl, furazan-3-yl), benzofurazanyl, benzothiophenyl, benzothiazolyl, benzoxazolyl, quinazolinyl, quinoxalinyl, naphthyridinyl, furopyridinyl, benzothiazolyl (such as benzo[d]thiazol-6-yl), indazolyl (such as 1H-indazol-5-yl) and 5,6,7,8-tetrahydroisoquinoline.

"Heterocyclyl," "heterocycle" or "heterocyclic" are interchangeable and refer to a non-aromatic heterocyclyl group comprising one or more heteroatoms selected from nitrogen, oxygen or optionally oxidized sulfur as ring members, with the remaining ring members being carbon, including monocyclic, fused, bridged, and spiro ring, i.e., containing monocyclic heterocyclyl, bridged heterocyclyl, spiro heterocyclyl, and fused heterocyclic groups.

The term "monocyclic heterocyclyl" refers to monocyclic groups in which at least one ring member is a heteroatom selected from nitrogen, oxygen or optionally oxidized sulfur. A heterocycle may be saturated or partially saturated.

Exemplary monocyclic 4 to 9-membered heterocyclyl groups include, but not limited to, (as numbered from the linkage position assigned priority 1) pyrrolidin-1-yl, pyrrolidin-2-yl, pyrrolidin-3-yl, imidazolidin-2-yl, imidazolidin-4-yl, pyrazolidin-2-yl, pyrazolidin-3-yl, piperidin-1-yl, piperidin-2-yl, piperidin-3-yl, piperidin-4-yl, 2,5-piperazinyl, pyranyl, morpholinyl, morpholino, morpholin-2-yl, morpholin-3-yl, oxiranyl, aziridin-1-yl, aziridin-2-yl, azocan-1-yl, azocan-2-yl, azocan-3-yl, azocan-4-yl, azocan-5-yl, thiiranyl, azetidin-1-yl, azetidin-2-yl, azetidin-3-yl, oxetanyl, thietanyl, 1,2-dithietanyl, 1,3-dithietanyl, dihydropyridinyl, tetrahydropyridinyl, thiomorpholinyl, thioxanyl, piperazinyl, homopiperazinyl, homopiperidinyl, azepan-1-yl, azepan-2-yl, azepan-3-yl, azepan-4-yl, oxepanyl, thiepanyl, 1,4-oxathianyl, 1,4-dioxepanyl, 1,4-oxathiepanyl, 1,4-oxaazepanyl, 1,4-dithiepanyl, 1,4-thiazepanyl and 1,4-diazepanyl, 1,4-dithianyl, 1,4-azathianyl, oxazepinyl, diazepinyl, thiazepinyl, dihydrothienyl, dihydropyranyl, dihydrofuranyl, tetrahydrofuranyl, tetrahydrothienyl, tetrahydropyranyl, tetrahydrothiopyranyl, 1-pyrrolinyl, 2-pyrrolinyl, 3-pyrrolinyl, indolinyl, 2H-pyranyl, 4H-pyranyl, 1,4-dioxanyl, 1,3-dioxolanyl, pyrazolinyl, pyrazolidinyl, dithianyl, dithiolanyl, pyrazolidinyl, imidazolinyl, pyrimidinonyl, or 1,1-dioxo-thiomorpholinyl.

The term "spiro heterocyclyl" refers to a 5 to 20-membered polycyclic heterocyclyl with rings connected through one common carbon atom (called a spiro atom), comprising one or more heteroatoms selected from nitrogen, oxygen or optionally oxidized sulfur as ring members, with the remaining ring members being carbon. One or more rings of a spiro heterocyclyl group may contain one or more double bonds, but none of the rings has a completely conjugated pi-electron system. Preferably a spiro heterocyclyl is 6 to 14-membered, and more preferably 7 to 12-membered. According to the number of common spiro atoms, a spiro heterocyclyl is divided into mono-spiro heterocyclyl, di-spiro heterocyclyl, or poly-spiro heterocyclyl, and preferably refers to mono-spiro heterocyclyl or di-spiro heterocyclyl, and more preferably 4-membered/4-membered, 3-membered/5-membered, 4-membered/5-membered, 4-membered/6-membered, 5-membered/5-membered, or 5-membered/6-membered mono-spiro heterocyclyl.

The term "fused heterocyclic group" refers to a 5 to 20-membered polycyclic heterocyclyl group, wherein each ring in the system shares an adjacent pair of atoms (carbon and carbon atoms or carbon and nitrogen atoms) with another ring, comprising one or more heteroatoms selected from nitrogen, oxygen or optionally oxidized sulfur as ring members, with the remaining ring members being carbon. One or more rings of a fused heterocyclic group may contain one or more double bonds, but none of the rings has a completely conjugated pi-electron system. Preferably, a fused heterocyclyl is 6 to 14-membered, and more preferably 7 to 10-membered. According to the number of membered rings, a fused heterocyclyl is divided into bicyclic, tricyclic, tetracyclic, or polycyclic fused heterocyclyl, preferably refers to bicyclic or tricyclic fused heterocyclyl, and more preferably 5-membered/5-membered, or 5-membered/6-membered bicyclic fused heterocyclyl.

Representative examples of fused heterocycles include, but not limited to, the following groups octahydrocyclopenta[c]pyrrole (e.g., octahydrocyclopenta[c]pyrrol-2-yl), octahydropyrrolo[3,4-c]pyrrolyl, octahydroisoindolyl, isoindolinyl (e.g., isoindoline-2-yl), octahydro-benzo[b][1,4]dioxin.

The term "bridged heterocyclyl" refers to a 5 to 14-membered polycyclic heterocyclic alkyl group, wherein every two rings in the system share two disconnected atoms, comprising one or more heteroatoms selected from nitrogen, oxygen or optionally oxidized sulfur as ring members, with the remaining ring members being carbon. One or more rings of a bridged heterocyclyl group may contain one or more double bonds, but none of the rings has a completely conjugated pi-electron system. Preferably, a bridged heterocyclyl is 6 to 14-membered, and more preferably 7 to 10-membered. According to the number of membered rings, a bridged heterocyclyl is divided into bicyclic, tricyclic, tetracyclic or polycyclic bridged heterocyclyl, and preferably refers to bicyclic, tricyclic or tetracyclic bridged heterocyclyl, and more preferably bicyclic or tricyclic bridged heterocyclyl. Representative examples of bridged heterocyclyls include, but not limited to, the following groups: 2-azabicyclo[2.2.1]heptyl, azabicyclo[3.1.0]hexyl, 2-azabicyclo[2.2.2]octyl and 2-azabicyclo[3.3.2]decyl.

Compounds disclosed herein may contain an asymmetric center and may thus exist as enantiomers. "Enantiomers" refer to two stereoisomers of a compound which are non-superimposable mirror images of one another. Where the compounds disclosed herein possess two or more asymmetric centers, they may additionally exist as diastereomers. Enantiomers and diastereomers fall within the broader class of stereoisomers. All such possible stereoisomers as substantially pure resolved enantiomers, racemic mixtures thereof, as well as mixtures of diastereomers are intended to be included. All stereoisomers of the compounds disclosed herein and/or pharmaceutically acceptable salts thereof are intended to be included. Unless specifically mentioned otherwise, reference to one isomer applies to any of the possible isomers. Whenever the isomeric composition is unspecified, all possible isomers are included.

The term "substantially pure" as used herein means that the target stereoisomer contains no more than 35%, such as no more than 30%, further such as no more than 25%, even further such as no more than 20%, by weight of any other stereoisomer(s). In some embodiments, the term "substantially pure" means that the target stereoisomer contains no more than 10%, for example, no more than 5%, such as no more than 1%, by weight of any other stereoisomer(s).

When compounds disclosed herein contain olefinic double bonds, unless specified otherwise, such double bonds are meant to include both E and Z geometric isomers.

When compounds disclosed herein contain a di-substituted cyclohexyl or cyclobutyl group, substituents found on cyclohexyl or cyclobutyl ring may adopt cis and trans formations. C is formation means that both substituents are found on the upper side of the 2 substituent placements on the carbon, while trans would mean that they were on opposing sides.

It may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography.

Chromatography can involve any number of methods including, for example: reverse-phase and normal phase; size exclusion; ion exchange; high, medium and low pressure liquid chromatography methods and apparatus; small scale analytical; simulated moving bed ("SMB") and preparative thin or thick layer chromatography, as well as techniques of small scale thin layer and flash chromatography. One skilled in the art will apply techniques most likely to achieve the desired separation.

"Diastereomers" refers to stereoisomers of a compound with two or more chiral centers but which are not mirror images of one another. Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Enantiomers can also be separated by use of a chiral HPLC column.

A single stereoisomer, e.g., a substantially pure enantiomer, may be obtained by resolution of the racemic mixture using a method such as formation of diastereomers using optically active resolving agents [Eliel, E. and Wilen, S. *Stereochemistry of Organic Compounds*. New York: John Wiley & Sons, Inc., 1994; Lochmuller, C. H., et al. "*Chromatographic resolution of enantiomers: Selective review*." J. Chromatogr., 113(3) (1975): pp. 283-302]. Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: Wainer, Irving W, *Ed. Drug Stereochemistry: Analytical Methods and Pharmacology*. New York: Marcel Dekker, Inc., 1993.

"Pharmaceutically acceptable salts" refers to those salts which are, within the scope of sound medical judgment, suitable for use in contact with the tissues of humans and lower animals without undue toxicity, irritation, allergic response and the like, and are commensurate with a reasonable benefit/risk ratio. A pharmaceutically acceptable salt may be prepared in situ during the final isolation and purification of the compounds disclosed herein, or separately by reacting the free base function with a suitable organic acid or by reacting the acidic group with a suitable base.

In addition, if a compound disclosed herein is obtained as an acid addition salt, the free base can be obtained by basifying a solution of the acid salt. Conversely, if the product is a free base, an addition salt, such as a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used without undue experimentation to prepare non-toxic pharmaceutically acceptable addition salts.

As defined herein, "a pharmaceutically acceptable salt thereof" include salts of at least one compound of Formula (I), and salts of the stereoisomers of the compound of Formula (I), such as salts of enantiomers, and/or salts of diastereomers.

The terms "administration", "administering", "treating" and "treatment" herein, when applied to an animal, human, experimental subject, cell, tissue, organ, or biological fluid, mean contact of an exogenous pharmaceutical, therapeutic, diagnostic agent, or composition to the animal, human, subject, cell, tissue, organ, or biological fluid. Treatment of a cell encompasses contact of a reagent to the cell, as well as contact of a reagent to a fluid, where the fluid is in contact with the cell. The term "administration" and "treatment" also means in vitro and ex vivo treatments, e.g., of a cell, by a reagent, diagnostic, binding compound, or by another cell. The term "subject" herein includes any organism, preferably an animal, more preferably a mammal (e.g., rat, mouse, dog, cat, rabbit) and most preferably a human.

The term "effective amount" or "therapeutically effective amount" refers to an amount of the active ingredient, such as compound that, when administered to a subject for treating a disease, or at least one of the clinical symptoms of a disease or disorder, is sufficient to affect such treatment for the disease, disorder, or symptom. The "therapeutically effective amount" can vary with the compound, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be apparent to those skilled in the art or can be determined by routine experiments. In some embodiments, "therapeutically effective amount" is an amount of at least one compound and/or at least one stereoisomer thereof, and/or at least one pharmaceutically acceptable salt thereof disclosed herein effective to "treat" as defined above, a disease or disorder in a subject. In the case of combination therapy, the "therapeutically effective amount" refers to the total amount of the combination objects for the effective treatment of a disease, a disorder or a condition.

The pharmaceutical composition comprising the compound disclosed herein can be administrated via oral, inhalation, rectal, parenteral or topical administration to a subject in need thereof. For oral administration, the pharmaceutical composition may be a regular solid Formulation such as tablets, powder, granule, capsules and the like, a liquid Formulation such as water or oil suspension or other liquid Formulation such as syrup, solution, suspension or the like; for parenteral administration, the pharmaceutical composition may be solution, water solution, oil suspension concentrate, lyophilized powder or the like. Preferably, the Formulation of the pharmaceutical composition is selected from tablet, coated tablet, capsule, suppository, nasal spray or injection, more preferably tablet or capsule. The pharmaceutical composition can be a single unit administration with an accurate dosage. In addition, the pharmaceutical composition may further comprise additional active ingredients.

All Formulations of the pharmaceutical composition disclosed herein can be produced by the conventional methods in the pharmaceutical field. For example, the active ingredient can be mixed with one or more excipients, then to make the desired Formulation. The "pharmaceutically acceptable excipient" refers to conventional pharmaceutical carriers suitable for the desired pharmaceutical Formulation, for example: a diluent, a vehicle such as water, various organic solvents, etc., a filler such as starch, sucrose, etc. a binder such as cellulose derivatives, alginates, gelatin and polyvinylpyrrolidone (PVP); a wetting agent such as glycerol; a disintegrating agent such as agar, calcium carbonate and sodium bicarbonate; an absorption enhancer such as quaternary ammonium compound; a surfactant such as hexadecanol; an absorption carrier such as Kaolin and soap clay; a lubricant such as talc, calcium stearate, magnesium stearate, polyethylene glycol, etc. In addition, the pharmaceutical composition further comprises other pharmaceutically acceptable excipients such as a decentralized agent, a stabilizer, a thickener, a complexing agent, a buffering agent, a permeation enhancer, a polymer, aromatics, a sweetener, and a dye.

The term "disease" refers to any disease, discomfort, illness, symptoms or indications, and can be interchangeable with the term "disorder" or "condition".

Throughout this specification and the claims which follow, unless the context requires otherwise, the term "comprise," and variations such as "comprises" and "comprising" are intended to specify the presence of the features thereafter, but do not exclude the presence or addition of one or more other features. When used herein the term "comprising" can be substituted with the term "containing", "including" or sometimes "having".

Throughout this specification and the claims which follow, the term "Cn-m" indicates a range which includes the endpoints, wherein n and m are integers and indicate the number of carbons. Examples include C1-8, C1-6, and the like.

Unless specifically defined elsewhere in this document, all other technical and scientific terms used herein have the meaning commonly understood by one of ordinary skill in the art to which this invention belongs.

EXAMPLE

The examples below are intended to be purely exemplary and should not be considered to be limiting in any way. Efforts have been made to ensure accuracy with respect to numbers used (for example, amounts, temperature, etc.), but some experimental errors and deviations should be accounted for. Unless indicated otherwise, temperature is in degrees Centigrade.

Reagents were purchased from commercial suppliers such as Sigma-Aldrich, Alfa Aesar, or TCI, and were used without further purification unless indicated otherwise.

Unless indicated otherwise, the reactions set forth below were performed under a positive pressure of nitrogen or argon or with a drying tube in anhydrous solvents; the reaction flasks were fitted with rubber septa for the introduction of substrates and reagents via syringe; and glassware was oven dried and/or heat dried.

Unless otherwise indicated, the reactions set forth below were performed under a positive pressure of nitrogen or argon or with a drying tube in anhydrous solvents; the reaction flasks were fitted with rubber septa for the introduction of substrates and reagents via syringe; and glassware was oven dried and/or heat dried.

Unless otherwise indicated, column chromatography purification was conducted on a Biotage system (Manufacturer: Dyax Corporation) having a silica gel column or on a silica SepPak cartridge (Waters), or was conducted on a Teledyne Isco Combiflash purification system using pre-packed silica gel cartridges.

$^1$H NMR spectra were recorded on a Varian instrument operating at 400 MHz. $^1$H-NMR spectra were obtained using $CDCl_3$, $CD_2Cl_2$, $CD_3OD$, $D_2O$, $d_6$-DMSO, $d_6$-acetone or $(CD_3)_2CO$ as solvent and tetramethylsilane (0.00 ppm) or residual solvent ($CDCl_3$: 7.25 ppm; $CD_3OD$: 3.31 ppm; $D_2O$: 4.79 ppm; $d_6$-DMSO: 2.50 ppm; $d_6$-acetone: 2.05; $(CD_3)_2CO$: 2.05) as the reference standard. When peak multiplicities are reported, the following abbreviations are used: s (singlet), d (doublet), t (triplet), q (quartet), qn (quintuplet), sx (sextuplet), m (multiplet), br (broadened), dd (doublet of doublets), dt (doublet of triplets). Coupling constants, when given, are reported in Hertz (Hz). Compound names except the reagents were generated by ChemDraw version 12.0.

Abbreviations:

AcOH Acetic acid
Aq Aqueous
Brine Saturated aqueous sodium chloride solution
Bn Benzyl
BnBr Benzyl Bromide
$(Boc)_2O$ di-tert-butyl dicarbonate
DMF N,N-Dimethylformamide
Dppf 1,1"-bis(diphenylphosphino)ferrocene
DBU 1,8-diazabicyclo[5.4.0]undec-7-ene
DIEA or DIPEA N-ethyl-N-isopropylpropan-2-amine
DMAP 4-N,N-dimethylaminopyridine
DMF N,N-dimethylformamide
DMSO Dimethyl sulfoxide
EtOAc Ethyl acetate
EtOH Ethanol
$Et_2O$ or ether Diethyl ether
$Et_3N$ Triethyl amine
HATU O(7-Azabenzotriazol-1-yl)-N,N,N',N'-tetramethyluronium hexafluorophosphate
HPLC High-performance liquid chromatography
IPA 2-propanol
i-PrOH Isopropyl alcohol
ms or MS Mass spectrum
NaHMDS Sodium Hexamethylenedisilazane
PE petroleum ether
PPA Polyphosphoric acid
p-TSA p-Tolunesulfonic acid
Rt Retention time
Rt or rt Room temperature
TBAF Tetra-butyl ammonium fluoride
TBSCl tert-Butyldimethylsilyl chloride
TFA Trifluoroacetic acid
THE tetrahydrofuran
TLC thin layer chromatography

Example A

Example A1: Synthesis of 4-(benzo[d]oxazol-2-ylamino)-6-(cyclopropanecarboxamido)-N-methylpyridazine-3-carboxamide (Compound 1)

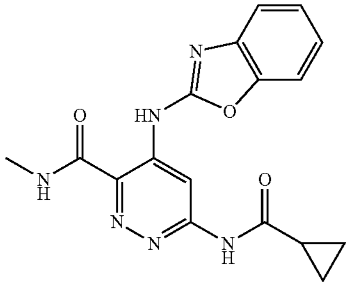 [SMILES: CNC(=O)c1nnc(NC(=O)C2CC2)cc1Nc1nc2ccccc2o1]

Step 1: 4-(benzo[d]oxazol-2-ylamino)-6-chloro-N-methylpyridazine-3-carboxamide

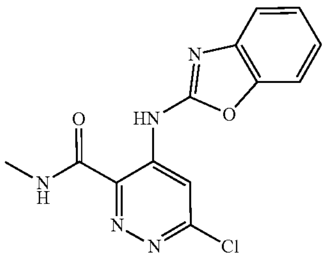 [SMILES: CNC(=O)c1nnc(Cl)cc1Nc1nc2ccccc2o1]

To a solution of benzo[d]oxazol-2-amine (134 mg, 1 mmol) and 4,6-dichloro-N-methylpyridazine-3-carboxamide (410 mg, 2 mmol) in 10 mL of THF was added KHMDS (4 mL, 1M in THF) at room temperature and the resulting solution was stirred at this temperature for 2 h. Upon completion of the reaction, 1N HCl was added to adjust the pH=7. The solution was concentrated in vacuo and the residue was purified by CombiFlash (MeOH/DCM=1%-10%) to give the product (60 mg, 19%) as a yellow solid. MS (ESI) m/e [M+1]+=303.9.

Step 2: 4-(benzo[d]oxazol-2-ylamino)-6-(cyclopropanecarboxamido)-N-methylpyridazine-3-carboxamide (Compound 1)

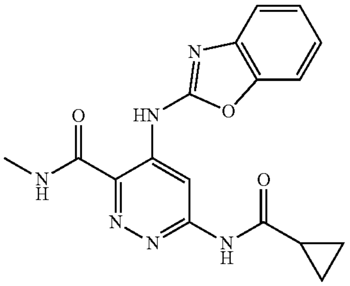 [SMILES: CNC(=O)c1nnc(NC(=O)C2CC2)cc1Nc1nc2ccccc2o1]

A mixture of 4-(benzo[d]oxazol-2-ylamino)-6-chloro-N-methylpyridazine-3-carboxamide (30 mg, 0.1 mmol), cyclopropanecarboxamide (34 mg, 0.4 mmol), xantPhos-Pd-G3 (5 mg, 0.005 mmol), Xantphos (3 mg, 0.005 mmol), and Cs2CO3 (163 mg, 0.5 mmol) in 3 mL of dioxane was heated at 130° C. under N2 in a sealed tube for 4 h. After cooled to room temperature, the solution was concentrated under vacuum and the residue was purified by Prep-TLC (MeOH/DCM=10:1) to give the product (3 mg, 9%). 1H NMR (400 MHz, DMSO-d6) δ 12.03 (s, 1H), 10.45 (s, 1H), 7.57 (t, J=7.9 Hz, 1H), 7.47 (s, 1H), 7.34 (d, J=6.5 Hz, 1H), 7.20 (d, J=8.3 Hz, 1H), 7.13 (t, J=7.7 Hz, 1H), 3.55 (s, 3H), 2.05 (d, J=4.4 Hz, 1H), 0.84 (d, J=7.6 Hz, 2H), 0.78 (d, J=3.8 Hz, 2H). MS (ESI) m/e [M+1]+=352.9.

The following Compounds 2-5 were synthesized starting from the corresponding starting materials according to the similar procedures described as those of Compound 1.

| Example | Compound | Chemical Name | $^{1}$H NMR data LC /MS m/z (M + 1) |
|---|---|---|---|
| Example A2 | Compound 2 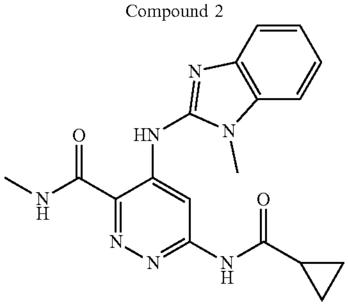 | 6-(cyclopropanecarboxamido)-N-methyl-4-((1-methyl-1H-benzo[d]imidazol-2-yl)amino) pyridazine-3-carboxamide | $^{1}$H NMR (400 MHz, DMSO-$d_6$) δ 12.58 (s, 1H), 11.43 (s, 1H), 9.67 (s, 1H), 9.45 (s, 1H), 7.46 (d, J = 8.4 Hz, 2H), 7.22-7.12 (m, 2H), 3.76 (s, 3H), 2.90 (d, J = 4.6 Hz, 3H), 1.99 (s, 1H), 0.92-0.83 (m, 4H). MS (ESI) m/e $[M + 1]^+$ = 365.9. |
| Example A3 | Compound 3 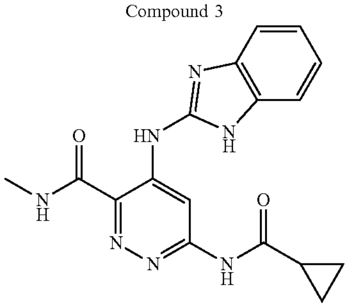 | 4-((1H-benzo [d]imidazol-2-yl)amino)-6-(cyclopropane-carboxamido)-N-methyl-pyridazine-3-carboxamide | $^{1}$H NMR (400 MHz, DMSO-$d_6$) δ 12.43 (s, 1H), 12.11 (s, 1H), 11.39 (s, 1H), 9.74 (s, 1H), 9.34 (d, J = 4.5 Hz, 1H), 7.45 (d, J = 5.0 Hz, 1H), 7.33 (s, 1H), 7.10 (dd, J = 5.6, 3.1 Hz, 2H), 2.89 (d, J = 4.5 Hz, 3H), 2.00 (dd, J = 14.3, 6.7 Hz, 1H), 0.90 (dd, J = 9.7, 6.2 Hz, 4H). MS (ESI) m/e $[M + 1]^+$ 351.9. |
| Example A4 | Compound 4 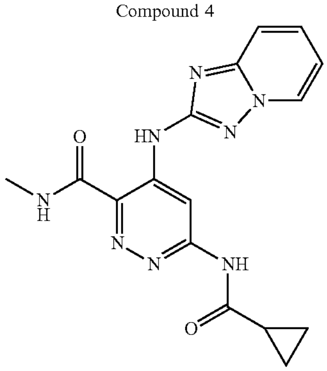 | 4-([1,2,4]triazolo[1,5-a]pyridin-2-ylamino)-6-(cyclopropane-carboxamido)-N-methyl-pyridazine-3-carboxamide | MS (ESI) m/e $[M + 1]^+$ 352.9. |
| Example A5 | Compound 5 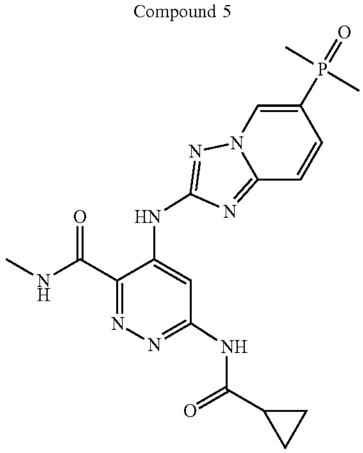 | 6-(cyclopropanecarboxamido)-4-((6-(dimethylphosphoryl)-[1,2,4]triazolo[1,5-a]pyridin-2-yl)amino)-N-methyl-pyridazine-3-carboxamide | $^{1}$H NMR (400 MHz, DMSO-$d_6$) δ 12.25 (s, 1H), 11.47 (s, 1H), 9.45 (s, 1H), 9.36 (d, J = 4.4 Hz, 1H), 9.03 (d, J = 8.8 Hz, 1H), 7.96 (t, J = 9.0 Hz, 1H), 7.84 (d, J = 8.8 Hz, 1H), 2.88 (d, J = 4.4 Hz, 3H), 2.20-2.14 (m, 1H), 1.80 (s, 3H), 1.77 (s, 3H), 0.97-0.84 (m, 4H). MS (ESI) m/e $[M + 1]^+$ 428.8 |

Example B

Example B1: Synthesis of 4-((6-(azetidin-1-yl)-7-methoxy-[1,2,4]triazolo[1,5-a]pyridin-2-yl)amino)-6-(cyclopropanecarboxamido)-N-methylpyridazine-3-carboxamide (Compound 6)

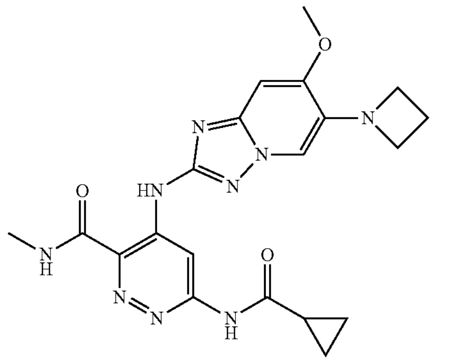 [SMILES: CNC(=O)c1nnc(NC(=O)C2CC2)cc1Nc1nc2cc(OC)c(N3CCC3)cn2n1]

Step 1: 6-bromo-7-methoxy-[1,2,4]triazolo[1,5-a]pyridin-2-amine

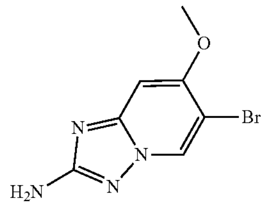

A solution of 5-bromo-4-methoxypyridin-2-amine (950 mg, 5 mmol) and O-ethyl carbonisothiocyanatidate (606 mg, 3 mmol) in 10 mL of dioxane was stirred at room temperature for 2 h. Upon completion of the reaction, the solvent was removed in vacuo and the residue was re-dissolved with 10 mL of ethanol, then hydroxylamine hydrochloride (1 g, 15 mmol) and DIPEA (1.16 g, 9 mmol) were added and the mixture was stirred at 70° C. for 24 h. After cooled to room temperature, the solution was concentrated, and 50 mL of water was added. The precipitated solid was collected and dried to give the product (500 mg, 69%) as a white solid. MS (ESI) m/e [M+1]+=242.9.

Step 2: 6-(azetidin-1-yl)-7-methoxy-[1,2,4]triazolo[1,5-a]pyridin-2-amine

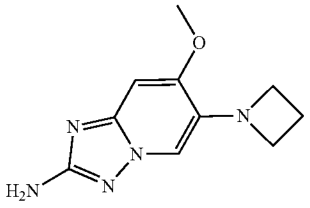 [SMILES: COc1cc2nc(N)nn2cc1N1CCC1]

A mixture of 6-bromo-7-methoxy-[1,2,4]triazolo[1,5-a]pyridin-2-amine (570 mg, 2.35 mmol), azetidine hydrochloride (441 mg, 4.7 mmol), $Pd_2(dba)_3$ (1.1 g, 1.18 mmol), Xantphos (683 mg, 1.18 mmol) and Cs2CO3 (3.06 g, 9.4 mmol) in 20 mL of dioxane was heated at 130° C. under $N_2$ atmosphere in a sealed tube for 4 h. After cooled to room temperature, the solution was removed in vacuo and the residue was purified by Combiflash (MeOH/DCM=1%-15%) to give the product (300 mg, 58%) as a white solid. MS (ESI) m/e $[M+1]^+$=220.

Step 3: 4-((6-(azetidin-1-yl)-7-methoxy-[1,2,4]triazolo[1,5-a]pyridin-2-yl)amino)-6-chloro-N-methylpyridazine-3-carboxamide

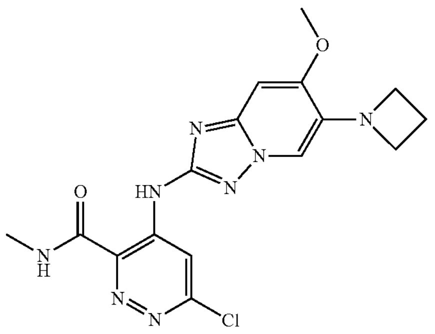 [SMILES: CNC(=O)c1nnc(Cl)cc1Nc1nc2cc(OC)c(N3CCC3)cn2n1]

The desired compound was prepare from 6-(azetidin-1-yl)-7-methoxy-[1,2,4]triazolo[1,5-a]pyridin-2-amine and 4,6-dichloro-N-methylpyridazine-3-carboxamide according to the procedure similar to that for compound 1 step 1 to give the product (140 mg, 56%) as a brown solid. MS (ESI) m/e $[M+1]^+$=388.9.

Step 4: 4-((6-(azetidin-1-yl)-7-methoxy-[1,2,4]triazolo[1,5-a]pyridin-2-yl)amino)-6-(cyclopropanecarboxamido)-N-methylpyridazine-3-carboxamide (Compound 6)

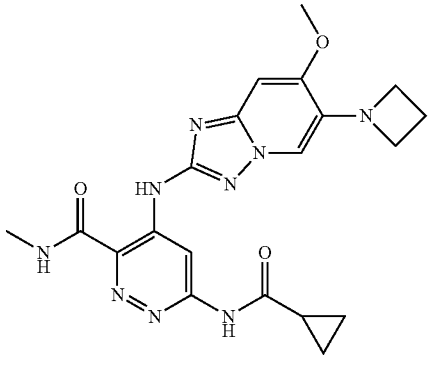 [SMILES: CNC(=O)c1nnc(NC(=O)C2CC2)cc1Nc1nc2cc(OC)c(N3CCC3)cn2n1]

The desired compound was prepared from 4-((6-(azetidin-1-yl)-7-methoxy-[1,2,4]triazolo[1,5-a]pyridin-2-yl)amino)-6-chloro-N-methylpyridazine-3-carboxamide according to the procedure similar to that for Compound 1 in Example A1 step 2 to give the product (10 mg, 91%). MS (ESI) m/e $[M+1]^+$=438. $^1$H NMR (400 MHz, DMSO-$d_6$) δ 11.90 (s, 1H), 11.35 (s, 1H), 9.28 (s, 2H), 7.71 (s, 1H), 7.01

(s, 1H), 3.91 (s, 3H), 3.84 (t, J=6.7 Hz, 4H), 2.86 (d, J=3.7 Hz, 3H), 2.30-2.19 (m, 2H), 2.14 (s, 1H), 0.89 (d, J=8.3 Hz, 4H). (s, 4H).

Example C

Examples C1, C2 and C3: Synthesis of tert-butyl 3-((2-((6-(cyclopropanecarboxamido)-3-(methylcarbamoyl)pyridazin-4-yl)amino)-[1,2,4]triazolo[1,5-a]pyridin-6-yl)oxy)azetidine-1-carboxylate (Compound 7), 4-((6-(azetidin-3-yloxy)-[1,2,4]triazolo[1,5-a]pyridin-2-yl)amino)-6-(cyclopropanecarboxamido)-N-methylpyridazine-3-carboxamide (Compound 8), and 6-(cyclopropanecarboxamido)-N-methyl-4-((6-((1-(methylsulfonyl)azetidin-3-yl)oxy)-[1,2,4]triazolo[1,5-a]pyridin-2-yl)amino)pyridazine-3-carboxamide (Compound 9)

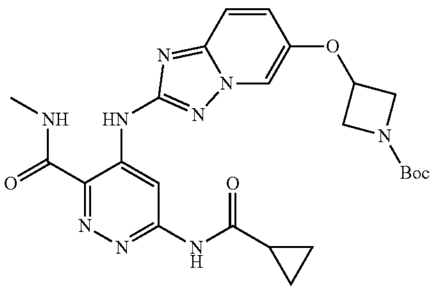

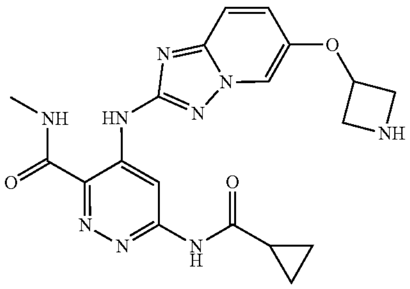

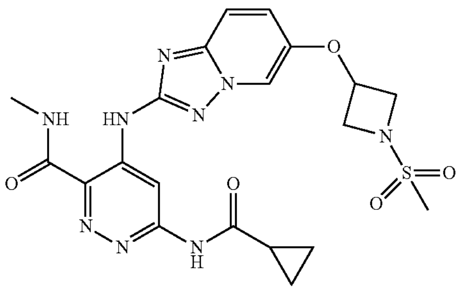

Step 1: 2-amino-[1,2,4]triazolo[1,5-a]pyridin-6-ol

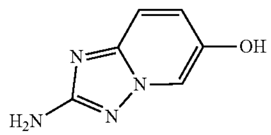

To a slurry of aluminum trichloride (1.29 g, 9.76 mmol) in DCM (50 mL) was added 6-methoxy-[1,2,4]triazolo[1,5-a]pyridin-2-amine (800 mg, 4.88 mmol) and the resulting mixture was stirred at room temperature for overnight. Upon completion of the reaction, water was added and the resulting solution was extracted with DCM. The combined organic layer was concentrated and the residue was purified by flash chromatography (MeOH: DCM=15:85) to give the product (600 mg, 73%) as yellow oil. MS (ESI) m/e $[M+H]^+$=151.

Step 2: tert-butyl 3-((2-amino-[1,2,4]triazolo[1,5-a]pyridin-6-yl)oxy)azetidine-1-carboxylate

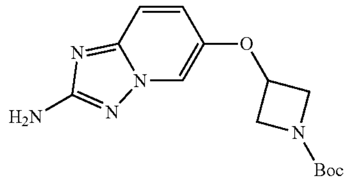 [SMILES: CC(C)(C)OC(=O)N1CC(Oc2ccc3nc(N)nn3c2)C1]

A mixture of 2-amino-[1,2,4]triazolo[1,5-a]pyridin-6-ol (300 mg, 2.00 mmol), tert-butyl 3-bromoazetidine-1-carboxylate (517 mg, 2.20 mmol) and $Cs_2CO_3$ (1.30 g, 4.00 mmol) in DMF (20 mL) was stirred at 60° C. for overnight. After cooled to room temperature, the solution was removed in vacuo and the residue was dissolved in MeOH/DCM (5 mL/25 mL), the solid was removed by filtration and the filtrate was concentrated in vacuo. The residue was purified by silica gel column chromatography (MeOH:DCM=6:94) to give the product (600 mg, 73%) as a white solid. MS (ESI) m/e $[M+H]^+$=306.

Step 3: tert-butyl 3-((2-((6-chloro-3-(methylcarbamoyl)pyridazin-4-yl)amino)-[1,2,4]triazolo[1,5-a]pyridin-6-yl)oxy)azetidine-1-carboxylate To a solution of tert-butyl 3-((2-amino-[1,2,4]triazolo[1,5-a]pyridin-6-yl)oxy)azetidine-1-carboxylate (133 mg, 0.44 mmol) and 4,6-dichloro-N-methylpyridazine-3-carboxamide (133 mg, 0.65 mmol) in THE (10 mL) was added NaHMDS (1M in THF, 1.95 mL) in one portion at 70° C. and the resulting mixture was stirred at this temperature for 10 min. After cooled to room temperature, the solvent was removed in vacuo and the residue was purified by silica gel column chromatography (MeOH: DCM=7:93) to give the product (120 mg, 39%) as a yellow solid. MS (ESI) m/e $[M+H]^+$=475.

Step 4: tert-butyl 3-((2-((6-(cyclopropanecarboxamido)-3-(methylcarbamoyl)pyridazin-4-yl)amino)-[1,2,4]triazolo[1,5-a]pyridin-6-yl)oxy)azetidine-1-carboxylate (Compound 7)

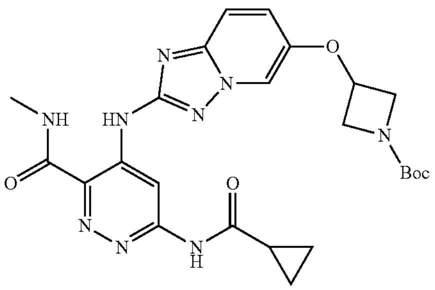 [SMILES: CNC(=O)c1nnc(NC(=O)C2CC2)cc1Nc1nc2ccc(OC3CN(C(=O)OC(C)(C)C)C3)cn2n1]

The desired compound was prepared from tert-butyl 3-((2-((6-chloro-3-(methylcarbamoyl)pyridazin-4-yl)amino)-[1,2,4]triazolo[1,5-a]pyridin-6-yl)oxy)azetidine-1-carboxylate according to the procedure similar to that for Compound 1 Example A1 step 2 to give the product (66 mg, 55%). $^1$H NMR (400 MHz, DMSO-$d_6$) 12.09 (s, 1H), 11.40 (s, 1H), 9.31-9.34 (m, 2H), 8.44 (d, J=2.2 Hz, 1H), 7.67 (d, J=9.7 Hz, 1H), 7.46 (dd, J=9.6, 2.3 Hz, 1H), 5.12-5.13 (m, 1H), 4.34-4.35 (m, 2H), 3.86-3.88 (m, 2H), 2.87 (d, J=4.8 Hz, 3H), 2.14-2.15 (m, 1H), 1.42 (s, 9H), 0.88-0.92 (m, 4H). MS (ESI) m/e $[M+H]^+$=524.

Step 5: 4-((6-(azetidin-3-yloxy)-[1,2,4]triazolo[1,5-a]pyridin-2-yl)amino)-6-(cyclopropanecarboxamido)-N-methylpyridazine-3-carboxamide (Compound 8)

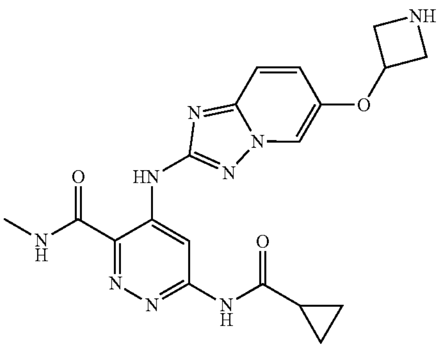 [SMILES: CNC(=O)c1nnc(NC(=O)C2CC2)cc1Nc1nc2ccc(OC3CNC3)cn2n1]

To a solution of tert-butyl 3-((2-((6-(cyclopropanecarboxamido)-3-(methylcarbamoyl)pyridazin-4-yl)amino)-[1,2,4]triazolo[1,5-a]pyridin-6-yl)oxy)azetidine-1-carboxylate (60 mg, 0.11 mmol) in DCM (10 mL) was added TFA (1 mL) and the resulting mixture was stirred at room temperature for 2 h. Upon completion of the reaction, the solvent was removed in vacuo and the residue was lyophilized with 0.5 M HCl to give the product (30 mg, 48%). $^1$H NMR (400 MHz, DMSO-$d_6$) 12.12 (s, 1H), 11.43 (s, 1H), 9.20-9.35 (m, 4H), 8.55 (s, 1H), 7.71 (d, J=9.6 Hz, 1H), 7.49 (d, J=9.6 Hz, 1H), 5.19-5.20 (m, 1H), 4.47-4.48 (m, 2H), 4.06-4.07 (m, 2H), 2.87 (d, J=4.7 Hz, 3H), 2.15-2.17 (m, 1H), 0.89-0.91 (m, 4H). MS (ESI) m/e $[M+H]^+$=424.

Step 6: 6-(cyclopropanecarboxamido)-N-methyl-4-(6-((1methylsulfonyl)azetidin-3-yl)oxy)-[1,2,4]triazolo[1,5-a]pyridin-2-yl)amino)pyridazine-3-carboxamide (Compound 9)

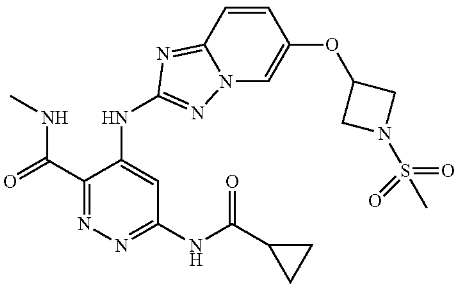 [SMILES: CNC(=O)c1nnc(NC(=O)C2CC2)cc1Nc1nc2ccc(OC3CN(S(C)(=O)=O)C3)cn2n1]

To a solution of 4-((6-(azetidin-3-yloxy)-[1,2,4]triazolo[1,5-a]pyridin-2-yl)amino)-6-(cyclopropanecarboxamido)-N-methylpyridazine-3-carboxamide (7 mg, 0.017 mmol) in THE (2 mL) were added methanesulfonyl chloride (4 mg, 0.034 mmol) and TEA (5 mg, 0.051 mmol). The resulting mixture was stirred at room temperature for 2 h. Upon completion of the reaction, the solvent was removed in vacuo and the residue was purified by Prep-TLC (MeOH: DCM=1: 20) to give the product (2.13 mg, 30) $^1$H NMR (400 MHz, DMSO-$d_6$) 12.10 (s, 1H), 11.40 (s, 1H), 9.30-9.33 (m, 2H), 8.52 (s, 1H), 7.69 (d, J=9.5 Hz, 1H), 7.48 (d, J=12.0 Hz, 1H), 5.16-5.17 (m, 1H), 4.34-4.35 (i, 2H), 3.98-4.00 (i, 2H), 3.09 (s, 3H), 2.87 (d, J=4.8 Hz, 3H), 2.15-2.16 (m, 1H), 0.88-0.90 (, 4H). MS (ESI) m/e $[M+H]^+$=502.

Compounds 10 and 51 were synthesized starting from the corresponding starting materials according to the similar procedures described as those of Compound 9.

| Example | Compound | Chemical Name | $^1$H NMR data LC/MS m/z (M + 1) |
| --- | --- | --- | --- |
| Example C4 | Compound 10 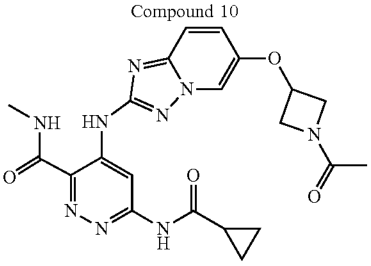 | 4-((6-((1-acetylazetidin-3-yl)oxy)-[1,2,4]triazolo[1,5-a]pyridin-2-yl)amino)-6-(cyclopropanecarboxamido)-N-methyl-pyridazine-3-carboxamide | H NMR (400 MHz, DMSO-$d_6$) δ 12.10 (s, 1H), 11.40 (s, 1H), 9.30-9.33 (m, 2H), 8.46 (s, 1H), 7.68 (d, J = 9.5 Hz, 1H), 7.47 (d, J = 9.4 Hz, 1H), 5.15-5.16 (m, 1H), 4.59-4.60 (m, 1H), 4.29-4.33 (m, 1H), 4.14 (d, J = 13.0 Hz, 1H), 3.84 (d, J = 11.3 Hz, 1H), 2.87 (d, J = 4.8 Hz, 4H), 2.14-2.15 (m, 1H), 1.80 (s, 3H), 0.88-0.92 (m, 4H). MS (ESI) m/e $[M + H]^+$ = 466. |

-continued

| Example | Compound | Chemical Name | $^1$H NMR data LC/MS m/z (M + 1) |
|---|---|---|---|
| Example C5 | Compound 51 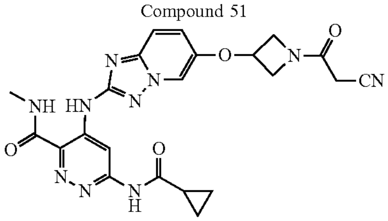 | 4-((6-((1-(2-cyanoacetyl) azetidin-3-yl) oxy)-[1,2,4] triazolo[1,5-a] pyridin-2-yl)amino)-6-(cyclopropanecarboxamido)-N-methylpyridazine-3-carboxamide | $^1$H NMR (400 MHz, DMSO-$d_6$) 12.10 (s, 1H), 11.40 (s, 1H), 9.30-9.33 (m, 2H), 8.49 (s, 1H), 7.69 (d, J = 9.6 Hz, 1H), 7.48 (d, J = 10.1 Hz, 1H), 5.19-5.20 (m, 1H), 4.59-4.62 (m, 1H), 4.38-4.40 (m, 1H), 4.20-4.21 (m, 1H), 3.93 (d, J = 9.8 Hz, 1H), 3.81 (s, 2H), 2.87 (d, J = 4.7 Hz, 3H), 2.15-2.16 (m, 1H), 0.88-0.90 (m, 4H). MS (ESI) m/e [M + H]$^+$ = 491. |

Example D

Example D1: Synthesis of 6-(cyclopropanecarboxamido)-N-methyl-4-((6-((1-(tetrahydrofuran-3-yl) azetidin-3-yl)oxy)-[1,2,4]triazolo[1,5-a]pyridin-2-yl) amino)pyridazine-3-carboxamide (Compound 52)

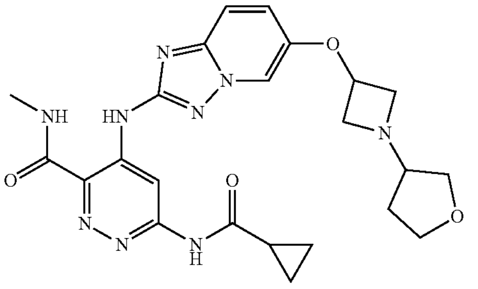 [SMILES: CNC(=O)c1nnc(NC(=O)C2CC2)cc1Nc1nc2ccc(OC3CN(C4CCOC4)C3)cn2n1]

To a solution of 4-((6-(azetidin-3-yloxy)-[1,2,4]triazolo [1,5-a]pyridin-2-yl)amino)-6-(cyclopropanecarboxamido)-N-methylpyridazine-3-carboxamide (7 mg, 0.017 mmol) and dihydrofuran-3(2H)-one (7 mg, 0.085 mmol) in DMF (2 mL) was added $NaBH(OAc)_3$ (35 mg, 0.17 mmol) and the resulting mixture was stirred at room temperature for overnight. Upon completion of the reaction, the solvent was removed in vacuo and the residue was purified by Prep-TLC (MeOH: DCM=1:20) to give the product (2.23 mg, 31%). $^1$H NMR (400 MHz, DMSO-$d_6$) 12.09 (s, 1H), 11.40 (s, 1H), 9.30-9.34 (m, 2H), 8.42 (s, 1H), 7.66 (d, J=9.3 Hz, 1H), 7.45 (d, J=9.3 Hz, 1H), 4.96-4.97 (m, 1H), 3.40-3.74 (m, 7H), 3.07-3.10 (m, 2H), 2.87 (d, J=3.9 Hz, 3H), 2.15-2.16 (m, 1H), 1.67-1.83 (m, 2H), 0.88-0.90 (m, 4H). MS (ESI) m/e [M+H]$^+$=494.

Example E

Example E1: Synthesis of 4-((6-(azetidin-1-yl)-[1,2,4]triazolo[1,5-a]pyridin-2-yl)amino)-6-(cyclopropanecarboxamido)-N-methylpyridazine-3-carboxamide (Compound 11)

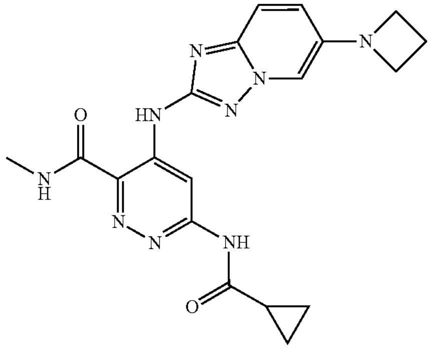 [SMILES: CNC(=O)c1nnc(NC(=O)C2CC2)cc1Nc1nc2ccc(N3CCC3)cn2n1]

Step 1: 5-(azetidin-1-yl)-2-nitropyridine

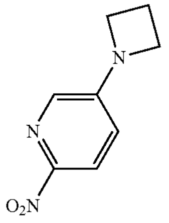 [SMILES: O=[N+]([O-])c1ccc(N2CCC2)cn1]

To a solution of 5-bromo-2-nitropyridine (3.0 g, 14.8 mmol) in EtOH (30 mL) were added azetidine hydrochloride (1.38 g, 14.8 mmol) and N-ethyl-N-isopropylpropan-2-amine (7.64 g, 59.1 mmol) at rt. The mixture was heated up to 60° C. and stirred at this temperature for 16 h under $N_2$. After cooled to room temperature, the solution was removed in vacuo and the residue was re-dissolved with water (5 mL). The resulting solution was extracted with EA/THF (v:v=2:1, 20 mL, 10 mL). The combined organic layer was washed with brine (10 mL), dried over $Na_2SO_4$, filtered and concentrated. The residue was purified by silica gel column chromatography (PE/EA=50:1, to 0:1) to give the product (1.2 g, 45.3%) as a yellow solid. MS (ESI) m/e $[M+1]^+$ 180.3.

Step 2: 5-(azetidin-1-yl)pyridin-2-amine

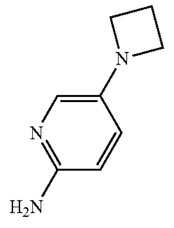 [SMILES: Nc1ccc(N2CCC2)cn1]

To a solution of 5-(azetidin-1-yl)-2-nitropyridine (1.2 g, 6.7 mmol) in MeOH/$H_2O$ (v:v=10:1, 11 mL) were added $NH_4Cl$ (716.5 mg, 13.4 mmol) and Iron powder (1.12 g, 20 mmol) at rt. The reaction mixture was stirred at rt for 12 h under $N_2$ atmosphere. Upon completion of the reaction, the solid was filtered and the filtrate was concentrated in vacuo to give the product (650 mg, 65%) as a light yellow solid, which was used for the next step without further purification.

P Step 3: ethyl N-([5-(azetidin-1-yl)pyridin-2-yl] carbonothioyl)carbamate

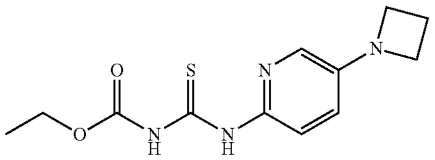 [SMILES: CCOC(=O)NC(=S)Nc1ccc(N2CCC2)cn1]

To a solution of 5-(azetidin-1-yl)pyridin-2-amine (650 mg, 4.4 mmol) in 1,4-dioxane (3 mL) was added O-ethyl carbonisothiocyanatidate (685.7 mg, 5.2 mmol) and the resulting mixture was stirred at rt for 3 h under $N_2$ atmosphere. Upon completion of the reaction, the solvent was removed in vacuo to give the product (1.3 g, crude) as a brown solid, which was used for the next step without further purification.

Step 4: 6-(azetidin-1-yl)-[1,2,4]triazolo[1,5-a]pyridin-2-amine

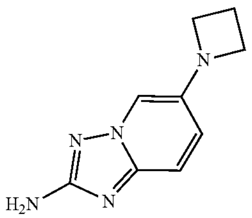 [SMILES: Nc1nc2ccc(N3CCC3)cn2n1]

To a solution of ethyl N-([5-(azetidin-1-yl)pyridin-2-yl] carbamothioyl)carbamate (1.3 g, 4.6 mmol) in MeOH/EtOH (v:v=1:1, 15 mL) were added DIPEA (1.2 g, 9.3 mmol) and $NH_2OH$ HCl (966.7 mg, 13.9 mmol) at rt. The resulting mixture was stirred at 60° C. for 15 h.

After cooled to room temperature, the solution was removed in vacuo and the residue was re-dissolved with water (15 mL). The resulting solution was extracted with DCM/MeOH (v:v=5:1, 30 mL×3). The combined organic layer was washed with brine (5 mL), dried over $Na_2SO_4$, filtered and concentrated. The residue was purified by silica gel column chromatography (DCM/MeOH, 100:1 to 1:1) to give the product (240 mg, 27.3%) as an off-white solid. $^1H$ NMR (DMSO-$d_6$) δ 7.65 (s, 1H), 7.21-7.18 (d, J=9.2 Hz, 1H), 6.84-6.81 (m, 1H), 5.67 (s, 2H), 3.76-3.72 (t, J=7 Hz, 4H), 2.3-2.24 (m, 2H). MS (ESI) m/e $[M+1]^+$190.1.

Step 5: 4-((6-(azetidin-1-yl)-[1,2,4]triazolo[1,5-a] pyridin-2-yl)amino)-6-chloro-N-methylpyridazine-3-carboxamide

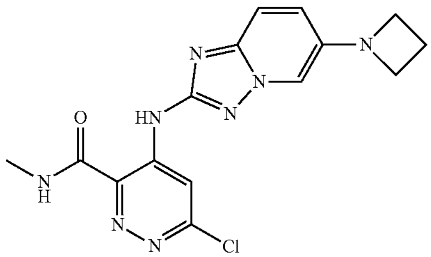 [SMILES: CNC(=O)c1nnc(Cl)cc1Nc1nc2ccc(N3CCC3)cn2n1]

To a suspension of 4,6-dichloro-N-methylpyridazine-3-carboxamide (54 mg, 0.26 mmol) and 6-(azetidin-1-yl)-[1,2,4]triazolo[1,5-a]pyridin-2-amine (50 mg, 0.26 mmol) in THF (10 mL) was added NaHMDS (0.5 mL, 1M in THF) in one portion at 70° C. and the resulting mixture was stirred at this temperature for 2 h. After cooled to room temperature, the solution was removed in vacuo and the residue was purified by silica gel column chromatography (MeOH/DCM=0-10%) to give the product (32 mg, 31%) as a brown solid. MS (ESI) m/e $[M+1]^+$ 358.9.

Step 6: 4-((6-(azetidin-1-yl)-[1,2,4]triazolo[1,5-a] pyridin-2-yl)amino)-6-(cyclopropanecarboxamido)-N-methylpyridazine-3-carboxamide (Compound 11)

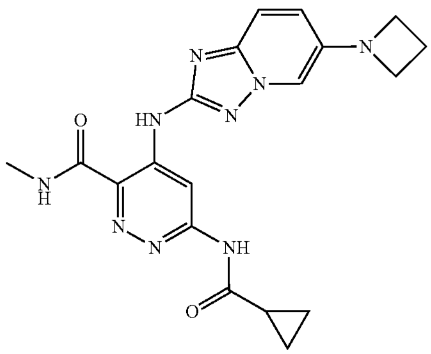 [SMILES: CNC(=O)c1nnc(NC(=O)C2CC2)cc1Nc1nc2ccc(N3CCC3)cn2n1]

A mixture of 4-((6-(azetidine-1-carbonyl)-[1,2,4]triazolo [1,5-a]pyridin-2-yl)amino)-6-chloro-N-methylpyridazine-3-carboxamide (32 mg, 0.09 mmol), cyclopropanecarboxamide (50 mg, 0.59 mmol), $Pd_2(dba)_3$ (30 mg, 0.03 mmol), Xant-Phos (30 mg, 0.05 mmol) and $Cs_2CO_3$ (100 mg, 0.31 mmol) in 1,4-dioxane (4 mL) and DMA (1 mL) was heated at 130° C. under $N_2$ atmosphere in a sealed tube for 4 h. After cooled to room temperature, DCM (10 mL) and MeOH (5 mL) were added and the resulting solution was filtered. The filtrate was concentrated in vacuo and the residue was purified by pre-TLC (DCM: MeOH=15:1) to give the product (2.02 mg, 5.8%) as a white solid. $^1$H NMR (400 MHz, DMSO-$d_6$) δ 12.00 (s, 1H), 11.38 (s, 1H), 9.35 (s, 1H), 9.30 (d, J=4.7 Hz, 1H), 7.87 (d, J=1.9 Hz, 1H), 7.56 (d, J=9.4 Hz, 1H), 7.09 (dd, J=9.4, 2.1 Hz, 1H), 3.86 (t, J=7.2 Hz, 4H), 2.87 (d, J=4.8 Hz, 3H), 2.39-2.26 (m, 2H), 2.14 (m, 1H), 1.04-0.76 (m, 4H). MS (ESI) m/e $[M+1]^+$ 407.9.

Example E2: Synthesis of 6-(cyclopropanecarboxamido)-4-((6-(3-methoxyazetidin-1-yl)-[1,2,4]triazolo[1,5-a]pyridin-2-yl)amino)-N-methylpyridazine-3-carboxamide (Compound 12)

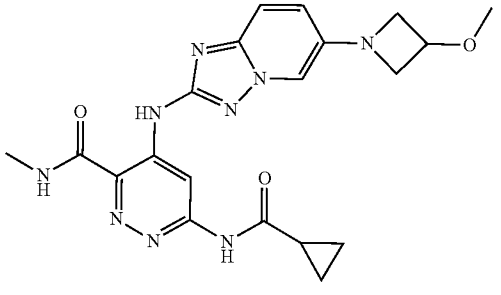

Step 1: 5-(3-methoxyazetidin-1-yl)-2-nitropyridine

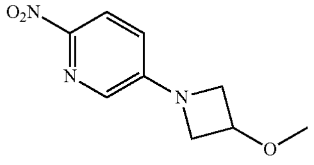

A mixture of 5-fluoro-2-nitropyridine (1 g, 7.0 mmol), 3-methoxyazetidine hydrochloride (1.13 g, 9.1 mmol) and DIEA (2.73 g, 21.2 mmol) in dioxane (10 mL) was stirred at 100° C. for 3 hr. The mixture was concentrated and the residue was re-dissolved in EA (20 mL). The organic phase was washed with sat. $NH_4Cl$ (20 mL×2) and brine (10 mL), dried over with $Na_2SO_4$, filtered and concentrated to afford the product (1 g, 68.3%) as yellow solid. H NMR (DMSO-$d_6$) δ 8.15 (d, J=9.0 Hz, 1H), 7.71 (d, J=2.8 Hz, 1H), 6.94 (d, J=9.0, 3.0 Hz, 1H), 4.36-4.43 (m, 1H), 4.26-4.34 (m, 2H), 3.90-3.97 (m, 2H), 3.25 (s, 3H).

Step 2: 5-(3-methoxyazetidin-1-yl)pyridin-2-amine

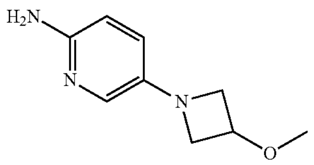

A mixture of 5-(3-methoxyazetidin-1-yl)-2-nitropyridine (500 mg, 2.39 mmol) and Raney Ni (wet, 500 mg) in THE (20 mL) was stirred at 25° C. for 3 hr under H2 (15 Psi) atmosphere. Upon completion of the reaction, the catalyst was removed by filtration and the filtrate was concentrated to afford the product (500 mg, crude) as brown solid. It was used directly for next step without further purification.

Step 3: ethyl N-([5-(3-methoxyazetidin-1-yl)pyridin-2-yl]carbamothioyl)carbamate

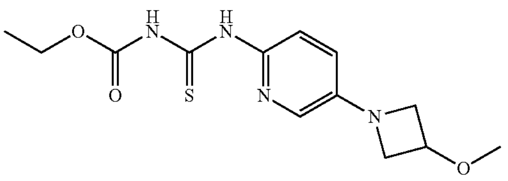 [SMILES: CCOC(=O)NC(=S)Nc1ccc(N2CC(OC)C2)cn1]

A mixture of 5-(3-methoxyazetidin-1-yl)pyridin-2-amine (500 mg, 2.79 mmol) and O-ethyl carbonisothiocyanatidate (549 mg, 4.19 mmol) in dioxane (10 mL) was stirred at 25° C. for 3 hr. The solvent was removed to afford the product (1 g, crude) as brown solid. It was used directly for next step without further purification.

Step 4: 6-(3-methoxyazetidin-1-yl)-[1,2,4]triazolo[1,5-a]pyridin-2-amine

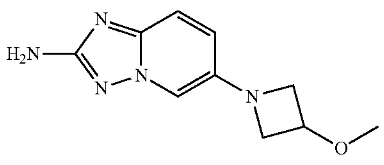 [SMILES: COC1CN(c2ccc3nc(N)nn3c2)C1]

A mixture of ethyl N-([5-(3-methoxyazetidin-1-yl)pyridin-2-yl]carbamothioyl)-carbamate (1 g, 2.7 mmol), $NH_2OH \cdot HCl$ (562.8 mg, 8.1 mmol) and DIEA (1.05 g, 8.1 mmol) in MeOH (5 mL)/EtOH (5 mL) was stirred at 60° C. for 10 hr. The mixture was concentrated and the residue was re-dissolved with EA (20 mL). The organic layer was washed with sat. $NH_4Cl$ (20 mL×2) and brine (10 mL), dried over $Na_2SO_{04}$, filtered and concentrated to give the residue, which was purified by silica gel column chromatography (PE: EA=2: 1) to afford the product (300 mg, 50.6%) as a yellow solid. $^1$H NMR (DMSO-$d_6$) δ 7.72 (d, J=2.0 Hz, 1H), 7.23 (d, J=9.2 Hz, 1H), 6.87 (d, J=9.3, 2.2 Hz, 1H), 5.63-5.73 (m, 2H), 4.26-4.33 (m, 1 H), 3.98-4.07 (m, 2H), 3.56 (d, J=8.3, 4.5 Hz, 2H), 3.21 (s, 3H). MS (ESI) m/e $[M+1]^+$ 220.2.

Step 5: 6-chloro-4-((6-(3-methoxyazetidin-1-yl)-[1,2,4]triazolo[1,5-a]pyridin-2-yl)amino)-N-methylpyridazine-3-carboxamide

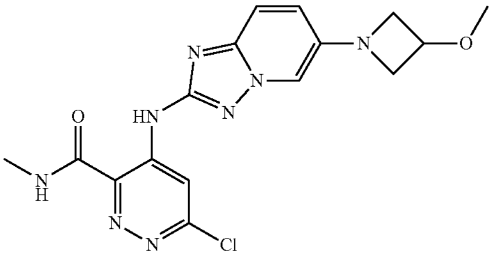

To a solution of 6-(3-methoxyazetidin-1-yl)-[1,2,4]triazolo[1,5-a]pyridin-2-amine (1.0 g, 4.56 mmol) in THE (30 mL) was added 4,6-dichloro-N-methylpyridazine-3-carboxamide (1.88 g, 9.12 mmol) at 25° C. under nitrogen atmosphere. The resulting mixture was heated up to 70° C. and to this was added KHMDS (18.2 mL, 1.0 M) in one portion. The resulting mixture was stirred at this temperature for 1 h under nitrogen atmosphere. After cooled to room temperature, the mixture was poured into water (500 mL) and extracted with EA (300 mL×2). The combined organic layer was washed with brine (200 mL), dried over $Na_2SO_4$, filtered and concentrated in vacuo to give the residue, which was purified by silica gel column chromatography (PE: EA=1: 1) to give the product (2.1 g, 20%) as a light yellow solid. $^1$H NMR ($CDCl_3$) δ: 11.89 (s, 1H), 8.76 (s, 1H), 8.2 (d, J=4.4 Hz, 1H), 7.58 (s, 1H), 7.40 (d, J=9.2 Hz, 1H), 6.87 (t, J=5.8 Hz, 1H), 4.31-4.34 (m, 1H), 4.09 (t, J=6.8 Hz, 2H), 3.66-3.69 (m, 2H), 3.29 (s, 3H), 3.00 (s, 3H). MS (ESI) m/e $[M+1]^+$ 389.1.

Step 6: 6-(cyclopropanecarboxamido)-4-((6-(3-methoxyazetidin-1-yl)-[1,2,4]triazolo[1,5-a]pyridin-2-yl)amino)-N-methylpyridazine-3-carboxamide

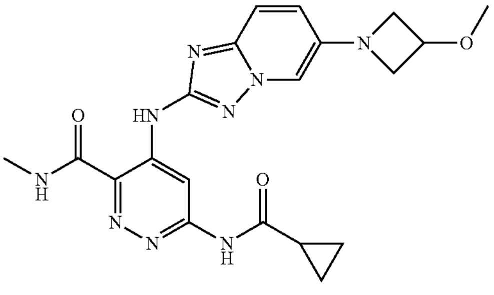

To a solution of 6-chloro-4-((6-(3-methoxyazetidin-1-yl)-[1,2,4]triazolo[1,5-a]pyridin-2-yl)amino)-N-methylpyridazine-3-carboxamide (500 mg, 1.29 mmol) in DMA (5 mL) were added cyclopropanecarboxamide (438 mg, 5.14 mmol), Xantphos (149 mg, 257 umol), $Pd_2(dba)_3$ (235 mg, 257 umol) and $Cs_2CO_3$ (1.68 g, 5.14 mmol) in a sealed tube. The reaction mixture was heated up to 120° C. and stirred at this temperature for 15 hr under nitrogen atmosphere. After cooled to room temperature, the solid was removed by filtration and the filtrate was concentrated in vacuo. The residue was purified by prep-HPLC (column: Phenomenex Gemini-NX; phase: A-$H_2O$ (10 mM $NH_4HCO_3$); B-Acetonitrile, B %:13%-43% in 20 min) to give the product (290 mg, 12%) as a light-yellow solid. $^1$H NMR (400 MHz, DMSO-$d_6$) δ 12.00 (s, 1H), 11.38 (s, 1H), 9.37-9.24 (m, 2H), 7.92 (d, J=1.9 Hz, 1H), 7.58 (d, J=9.3 Hz, 1H), 7.12 (d, J=9.4 Hz, 1H), 4.33 (d, J=6.2 Hz, 1H), 4.14-4.09 (m, 2H), 3.68 (d, J=8.3 Hz, 2H), 3.25 (s, 3H), 2.87 (d, J=4.8 Hz, 3H), 2.14 (s, 1H), 0.93-0.86 (m, 4H). MS (ESI) m/e $[M+1]^+$=437.9.

Compounds 13-15, 17, 19-25, 29-31, 33, 35, 54-55 below were synthesized starting from the corresponding starting materials according to the similar procedures described as those of Compound 11.

| Example | Compound | Chemical Name | $^1$H NMR data LC/MS m/z (M + 1) |
| --- | --- | --- | --- |
| Example E3 | Compound 13 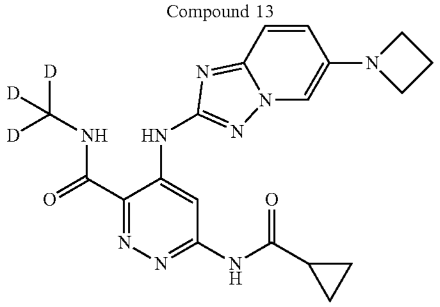 | 4-((6-(azetidin-1-yl)-[1,2,4]triazolo [1,5-a] pyridin-2-yl)amino)-6-(cyclopropanecarbox-amido)-N-(methyl-d3) pyridazine-3-carboxamide | $^1$H NMR (400 MHz, DMSO-$d_6$) δ 12.00 (s, 1H), 11.38 (s, 1H), 9.31 (d, J = 28.9 Hz, 2H), 7.87 (s, 1H), 7.56 (d, J = 9.4 Hz, 1H), 7.09 (d, J = 9.3 Hz, 1H), 3.86 (s, 4H), 2.33 (s, 2H), 2.14 (s, 1H), 0.90 (d, J= 13.2 Hz, 4H). MS (ESI) m/e $[M + 1]^+$ 411.4. |

-continued

| Example | Compound | Chemical Name | $^1H$ NMR data LC/MS m/z (M + 1) |
|---|---|---|---|
| Example E4 | Compound 14 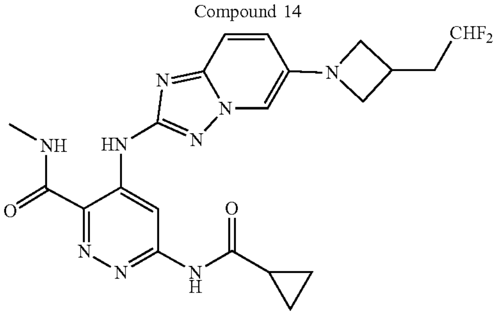 | 6-(cyclopropanecarboxamido)-4-((6-(3-(2,2-difluoroethyl)azetidin-1-yl)-[1,2,4]triazolo[1,5-a]pyridin-2-yl)amino)-N-methylpyridazine-3-carboxamide | $^1H$ NMR (400 MHz, DMSO-$d_6$) δ 11.99 (s, 1H), 11.37 (s, 1H), 9.34 (s, 1H), 9.29 (s, 1H), 7.89 (s, 1H), 7.56 (d, J = 9.4 Hz, 1H), 7.10 (d, J = 9.7 Hz, 1H), 6.13 (t, J = 56.6 Hz, 1H), 4.04 (t, J = 7.5 Hz, 2H), 3.60 (d, J = 6.2 Hz, 2H), 2.94 (m, 1H), 2.86 (d, J = 4.0 Hz, 3H), 2.18 (m, 3H), 0.88 (m, 4H). MS (ESI) m/e $[M + 1]^+$ 471.9. |
| Example E5 | Compound 15 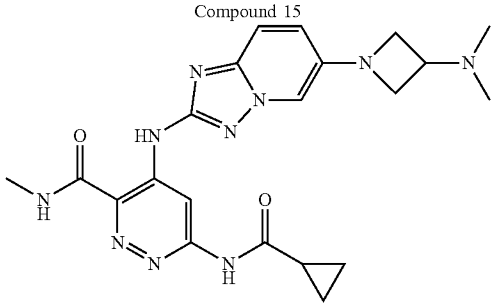 | 6-(cyclopropanecarboxamido)-4-((6-(3-(dimethylamino)azetidin-1-yl)-[1,2,4]triazolo [1,5-a]pyridin-2-yl)amino)-N-methylpyridazine-3-carboxamide | $^1H$ NMR (400 MHz, DMSO-$d_6$) δ δ 12.00 (s, 1H), 11.37 (s, 1H), 9.35 (s, 1H), 9.30 (d, J = 4.9 Hz, 1H), 8.15 (s, 1H), 7.89 (d, J = 1.8 Hz, 1H), 7.57 (d, J = 9.4 Hz, 1H), 7.11 (dd, J = 9.5, 2.2 Hz, 1H), 3.98 (t, J = 7.1 Hz, 2H), 3.61 (t, J = 7.1 Hz 2H), 3.25-3.18 (m, 1H), 2.87 (d, J = 4.8 Hz, 3H), 2.14 (m, 1H), 2.12 (s, 6H), 0.90 (m, 4H). MS (ESI) m/e $[M + 1]^+$ 450.9. |
| Example E6 | Compound 16 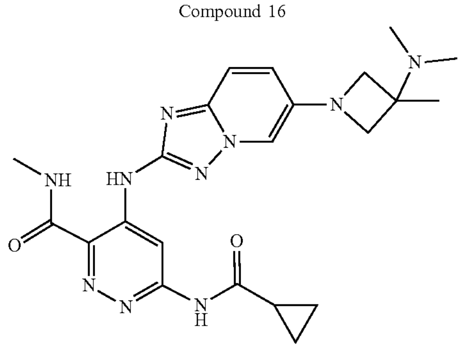 | 6-(cyclopropanecarboxamido)-4-((6-(3-(dimethylamino)-3-methylazetidin-1-yl)-[1,2,4]triazolo[1,5-alpyridin-2-yl)amino)-N-methylpyridazine-3-carboxamide | $^1H$ NMR (400 MHz, DMSO-$d_6$) δ 11.98 (s, 1H), 11.36 (s, 1H), 9.33 (s, 2H), 7.91 (s, 1H), 7.56 (d, J = 9.4 Hz, 1H), 7.11 (dd, J = 9.4, 2.1 Hz, 1H), 3.68 (s, 3H), 2.84 (d, J = 4.8 Hz, 3H), 2.37-1.99 (m, 7H), 1.36 (s, 3H), 0.88 (s, 4H). MS (ESI) m/e $[M + 1]^+$ 465.5. |
| Example E7 | Compound 17 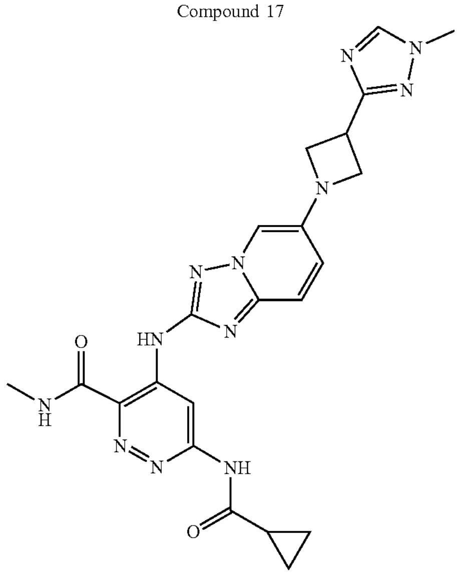 | 6-(cyclopropanecarboxamido)-N-methyl-4-((6-(3-(1-methyl-1H-1,2,4-triazol-3-yl)azetidin-1-yl)-[1,2,4]triazolo [1,5-a]pyridin-2-yl)amino)pyridazine-3-carboxamide | $^1H$ NMR (400 MHz, DMSO-$d_6$) δ 12.00 (s, 1H), 11.37 (s, 1H), 9.35 (s, 1H), 9.29 (s, 1H),8.41 (s, 1H), 8.00 (s, 1H), 7.64-7.43 (m, 2H), 7.16 (d, J = 9.0 Hz, 1H), 6.74 (s, 1H), 4.32-4.26 (m, 1H), 4.05-3.97 (m, 2H), 3.90-3.81 (m, 3H), 2.88 (s, 3H), 2.15-1.97 (m, 1H), 1.55-1.47 (m, 1H), 0.92-0.87 (m, 2H), 0.65-0.61 (m, 3H).MS (ESI) m/e $[M + 1]^+$ 488.9. |

-continued

| Example | Compound | Chemical Name | $^1$H NMR data LC/MS m/z (M + 1) |
|---|---|---|---|
| Example E8 | Compound 19 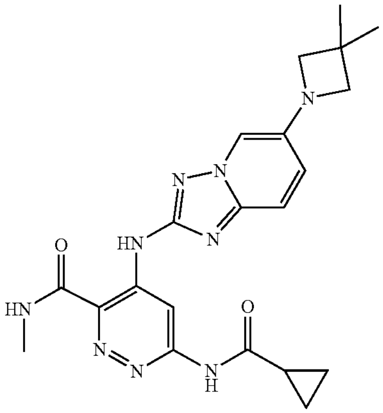 [SMILES: CNC(=O)c1nnc(NC(=O)C2CC2)cc1Nc1nc2ccc(N3CC(C)(C)C3)cn2n1] | 6-(cyclopropanecar-boxamido)-4-((6-(3,3-dimethylazetidin-1-yl)-[1,2,4]triazolo[1,5-a]pyridin-2-yl)amino)-N-methylpyridazine-3-carboxamide | $^1$H NMR (400 MHZ, DMSO-$d_6$) δ = 11.98 (s, 1H), 11.37 (s, 1H), 9.32 (d, J = 17.9, 2H), 7.87 (s, 1H), 7.56 (d, J = 9.5, 1H), 7.09 (d, J = 8.8, 1H), 3.59 (s, 5H), 2.87 (d, J = 3.9, 3H), 2.14 (s, 1H), 1.30 (s, 6H), 0.90 (s, 4H). MS (ESI) m/e [M + 1]$^+$ 436.4. |
| Example E9 | Compound 20 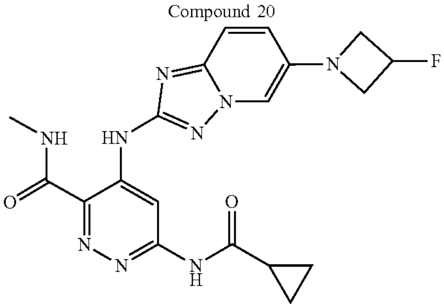 | 6-(cyclopropanecar-boxamido)-4-((6-(3-fluoroazetidin-1-yl)-[1,2,4]triazolo[1,5-a]pyridin-2-yl)amino)-N-methylpyridazine-3-carboxamide | $^1$H NMR (DMSO-$d_6$) δ 12.02 (s, 1H), 11.38 (s, 1H), 9.46-9.20 (m, 2H), 8.01 (s, 1H), 7.60 (d, J = 9.4 Hz, 1H), 7.16 (dd, J = 9.4, 1.7 Hz, 1H), 5.50 (d, J = 57.5 Hz, 1H), 4.27-4.18(m, 2H), 4.01-3.93 (m, 2H), 2.87 (d, J = 4.6 Hz, 3H), 2.17-2.11 (m, 1H), 0.91-0.85 (m, 4H). MS (ESI) m/e [M + 1]$^+$ 426.4. |
| Example E10 | Compound 21 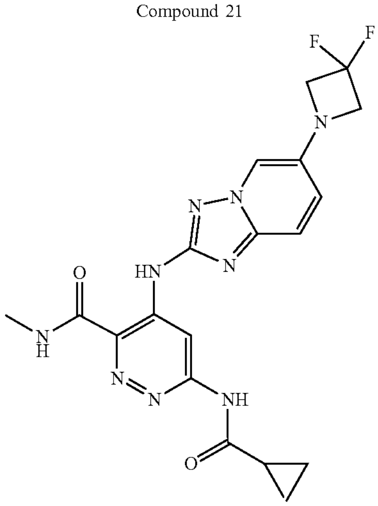 | 6-(cyclopropanecar-boxamido)-4-((6-(3,3-difluoroazetidin-1-yl)-[1,2,4]triazolo[1,5-a]pyridin-2-yl)amino)-N-methylpyridazine-3-carboxamide | MS (ESI) m/e [M + 1]$^+$ 443.9. |
| Example E11 | Compound 22 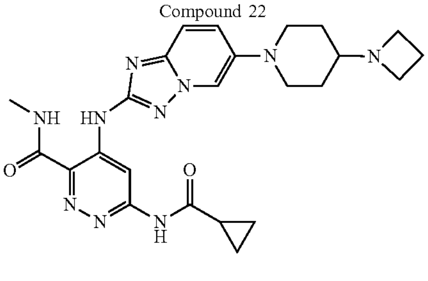 | 4-((6-(4-(azetidin-1-yl)piperidin-1-yl)-[1,2,4]triazolo[1,5-a]pyridin-2-yl)amino)-6-(cyclopropanecarbox-amido)-N-methyl-pyridazine-3-carboxamide | $^1$H NMR (400 MHz, DMSO-$d_6$) 12.04 (s, 1H), 11.39 (s, 1H), 9.30-9.34 (m, 2H), 8.24 (s, 1H), 7.66 (d, J = 9.8 Hz, 1H), 7.59 (d, J = 9.6 Hz, 1H), 4.01-4.11 (m, 4H), 3.73-3.74 (m, 2H), 2.87 (d, J = 3.4 Hz, 3H), 2.67-2.73 (m, 3H), 2.15-2.20 (m, 3H), 1.98-2.01 (m, 2H), 1.57-1.60 (m, 2H), 0.88-0.90 (m, 4H). MS (ESI) m/e [M + H]$^+$ = 491. |

-continued

| Example | Compound | Chemical Name | $^{1}H$ NMR data LC/MS m/z (M + 1) |
|---|---|---|---|
| Example E12 | Compound 23 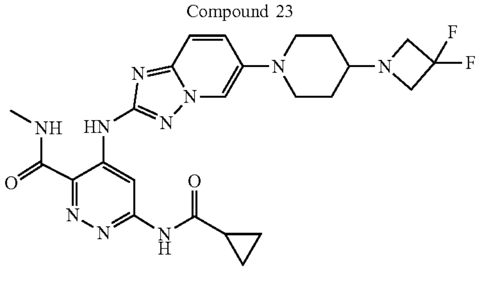 | 6-(cyclopropanecarboxamido)-4-((6-(4-(3,3-difluoroazetidin-1-yl)piperidin-1-yl)-[1,2,4]triazolo[1,5-a]pyridin-2-yl)amino)-N-methylpyridazine-3-carboxamide | $^{1}H$ NMR (400 MHz, DMSO-$d_6$) δ 12.02 (s, 1H), 11.39 (s, 1H), 9.27-9.37 (m, 2H), 8.16 (s, 1H), 7.64 (dd, 1H), 7.56 (d, 1H), 3.59 (t, 4H), 3.49-3.52 (m, 2H), 2.87 (d, 3H), 2.78 (t, 2H), 2.30-2.35 (m, 1H), 2.13-2.16 (m, 1H), 1.78-1.81 (m, 2H), 1.36-1.39 (m, 2H), 0.88-0.92 (m, 4H). MS (ESI) m/e $[M + H]^+$ = 527. |
| Example E13 | Compound 24 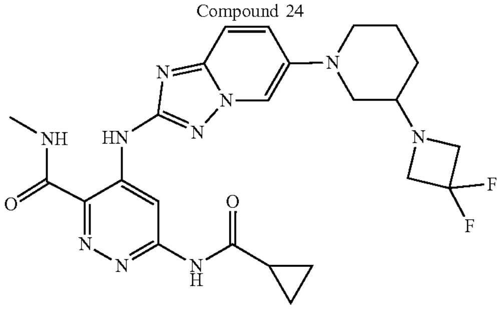 | 6-(cyclopropanecarboxamido)-4-((6-(3-(3,3-difluoroazetidin-1-yl)piperidin-1-yl)-[1,2,4]triazolo[1,5-a]pyridin-2-yl)amino)-N-methylpyridazine-3-carboxamide | $^{1}H$ NMR (400 MHz, DMSO-$d_6$) 12.02 (s, 1H), 11.37 (s, 1H), 9.34 (s, 1H), 9.30 (d, J = 4.7 Hz, 1H), 8.19 (s, 1H), 7.66 (d, J = 9.9 Hz, 1H), 7.57 (d, J = 9.7 Hz, 1H), 3.65 (t, J = 12.4 Hz, 4H), 3.45 (t, J = 10.6 Hz, 2H), 2.87 (d, J = 4.7 Hz, 3H), 2.68 (t, J = 10.3 Hz, 1H), 2.40-2.47 (m, 2H), 2.14-2.15 (m, 1H), 1.80 (d, J = 10.3 Hz, 2H), 1.55-1.62 (m, 1H), 1.05-1.17 (m, 1H), 0.88-0.92 (m, 4H). MS (ESI) m/e $[M + H]^+$ = 527. |
| Example E14 | Compound 25 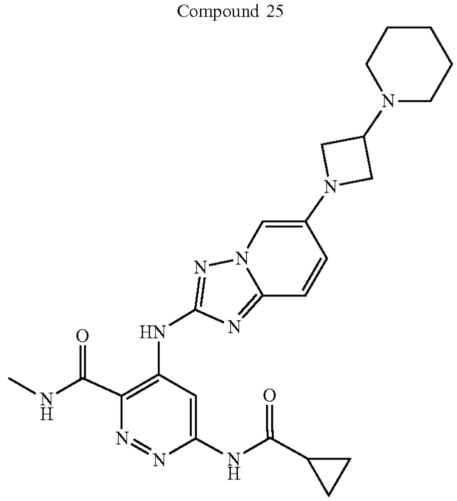 | 6-(cyclopropanecarboxamido)-N-methyl-4-((6-(3-(piperidin-1-yl)azetidin-1-yl)-[1,2,4]triazolo [1,5-a] pyridin-2-yl)amino) pyridazine-3-carboxamide | $^{1}H$ NMR (400 MHz, DMSO-$d_6$) δ 9.56 (s, 1H), 8.07 (s, 1H), 7.47 (d, J = 9.6 Hz, 1H), 7.23-7.10 (m, 1H), 4.10 (t, J = 7.2 Hz, 2H), 3.82-3.72 (m, 2H), 3.48-3.40 (m, 1H), 2.99 (s, 3H), 2.57-2.46 (m, 3H), 2.02-1.97 (m, 1H), 1.70-1.62 (m, 4H), 1.58-1.50 (m, 2H), 1.12-1.04 (m, 2H), 1.02-0.95 (m, 2H), 0.92-0.85 (m, 1H).MS (ESI) m/e $[M + 1]^+$ 490.9. |
| Example E15 | Compound 29 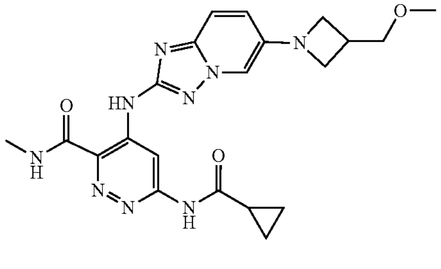 | 6-(cyclopropanecarboxamido)-4-((6-(3-(methoxymethyl) azetidin-1-yl)-[1,2,4]triazolo[1,5-a] pyridin-2-yl)amino)-N-methylpyridazine-3-carboxamide | $^{1}H$ NMR (400 MHz, DMSO-$d_6$) δ 11.99 (s, 1H), 11.37 (s, 1H), 9.35 (S, 1H), 9.29 (d, J = 4.5 Hz, 1H), 7.89 (s, 1H), 7.56 (d, J = 9.5 Hz, 1H), 7.10 (d, J = 9.4, 2.1 Hz, 1H), 3.94 (t, J = 7.5 Hz, 2H), 3.64-3.58 (m, 2H), 3.54 (d, J = 6.6 Hz, 2H), 2.94 (m, 1H), 2.87 (d, J = 4.7 Hz, 4H), 2.14 (m, 1H), 0.93-0.85 (m, 4H). MS (ESI) m/e $[M + 1]^+$ = 452.4. |

-continued

| Example | Compound | Chemical Name | $^1H$ NMR data LC/MS m/z (M + 1) |
|---|---|---|---|
| Example E16 | Compound 30 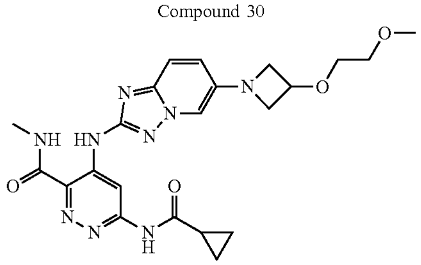 | 6-(cyclopropanecar-boxamido)-4-((6-(3-(2-methoxyethoxy)azetidin-1-yl)-[1,2,4]triazolo[1,5-a]pyridin-2-yl)amino)-N-methylpyridazine-3-carboxamide | $^1H$ NMR (400 MHz, DMSO-$d_6$) 12.00 (s, 1H), 11.37 (s, 1H), 9.34 (s, 1H), 9.30 (d, J = 5.0 Hz, 1H), 7.92 (s, 1H), 7.57 (d, J = 9.4 Hz, 1H), 7.12 (dd, J = 9.5, 2.0 Hz, 1H), 4.44 (s, 1H), 4.12 (t, J = 7.2 Hz, 2H), 3.63-3.65 (m, 2H), 3.52-3.53 (m, 2H), 3.46-3.47 (m, 2H), 3.26 (s, 3H), 2.87 (d, J = 4.8 Hz, 3H), 2.13-2.14 (m, 1H), 0.88-0.90 (m, 4H). MS (ESI) m/e $[M + H]^+$ = 482. |
| Example E17 | Compound 31 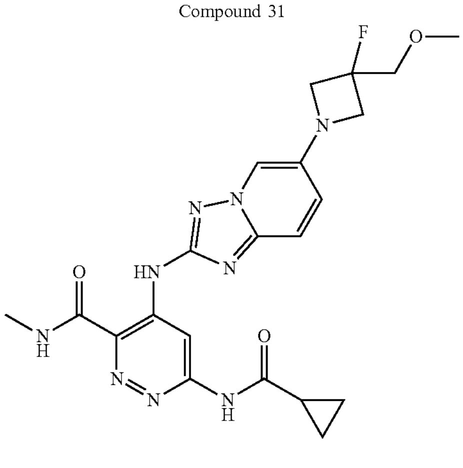 | 6-(cyclopropanecar-boxamido)-4-((6-(3-fluoro-3-(methoxy-methyl)azetidin-1-yl)-[1,2,4]triazolo[1,5-a]pyridin-2-yl)amino)-N-methylpyridazine-3-carboxamide | MS (ESI) m/e $[M + 1]^+$ = 469.9. |
| Example E18 | Compound 33 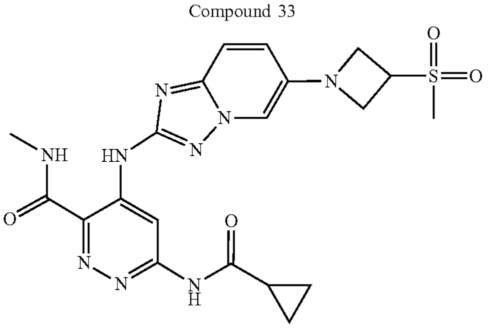 | 6-(cyclopropanecar-boxamido)-N-methyl-4-((6-(3-(methyl-sulfonyl)azetidin-1-yl)-[1,2,4]triazolo[1,5-a]pyridin-2-yl)amino)pyridazine-3-carboxamide | $^1H$ NMR (400 MHz, DMSO-$d_6$) 12.03 (s, 1H), 11.39 (s, 1H), 9.36 (s, 1H), 9.31 (d, J = 4.7 Hz, 1H), 8.06 (d, J = 2.0 Hz, 1H), 7.62 (d, J = 9.4 Hz, 1H), 7.17 (d, J = 9.5, 2.2 Hz, 1H), 4.42 (d, J = 7.9, 5.3 Hz, 1H), 4.21 (t, J = 8.4 Hz, 2H), 4.12-4.15 (m, 2H), 3.07 (s, 3H), 2.87 (d, J = 4.8 Hz, 3H), 2.13-2.16 (m, 1H), 0.84-0.92 (m, 4H). MS (ESI) m/e $[M + H]^+$ = 486. |

-continued

| Example | Compound | Chemical Name | $^1H$ NMR data LC/MS m/z (M + 1) |
|---|---|---|---|
| Example E19 | Compound 34 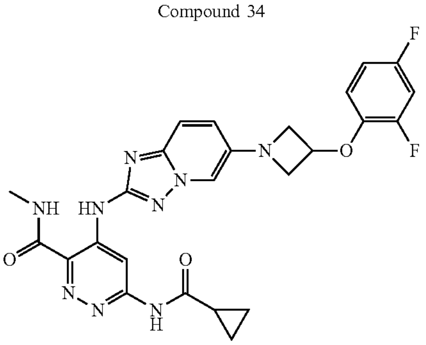 | 6-(cyclopropanecarboxamido)-4-((6-(3-(2,4-difluorophenoxy)azetidin-1-yl)-[1,2,4]triazolo[1,5-a]pyridin-2-yl)amino)-N-methylpyridazine-3-carboxamide | $^1H$ NMR (400 MHz, DMSO-$d_6$) δ 12.01 (s, 1H), 11.37 (s, 1H), 9.35 (s, 1H), 9.29 (d, J = 4.4 Hz, 1H), 8.02 (s, 1H), 7.60 (d, J = 9.3 Hz, 1H), 7.36 (t, J = 9.6 Hz, 1H), 7.18 (d, J = 9.5 Hz, 1H), 7.07 (m, 2H), 5.21 (m, 1H), 4.42-4.30 (m, 2H), 3.91 (d, J = 8.3, 3.8 Hz, 2H), 2.87 (d, J = 4.6 Hz, 1H), 2.14 (m, 1H), 0.95-0.86 (m, 4H). MS (ESI) m/e $[M + 1]^+$ = 535.8. |
| Example E20 | Compound 35 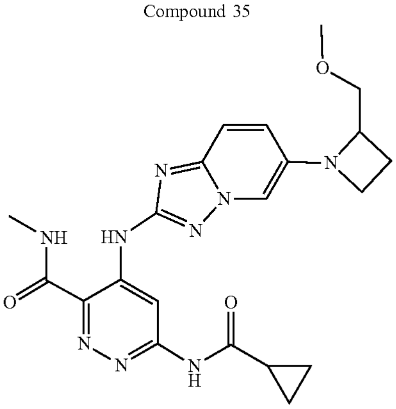 | 6-(cyclopropanecarboxamido)-4-((6-(2-(methoxymethyl)azetidin-1-yl)-[1,2,4]triazolo[1,5-a]pyridin-2-yl)amino)-N-methylpyridazine-3-carboxamide | $^1H$ NMR (400 MHz, DMSO-$d_6$) δ 11.98 (s, 1H), 11.38 (s, 1H), 9.40 (s, 1H), 9.29 (d, J = 4.5 Hz, 1H), 8.05 (s, 1H), 7.56 (d, J = 9.4 Hz, 1H), 7.26 (d, J = 9.5 Hz, 1H), 4.18 (d, J = 5.1 Hz, 1H), 3.92 (s, 1H), 3.72 - 3.52 (m, 3H), 3.37 (s, 3H), 2.87 (d, J = 4.7 Hz, 3H), 2.42-2.08 (m, 3H), 0.89 (m, 4H). MS (ESI) m/e $[M + 1]^+$ = 452.5. |
| Example E21 | Compound 53 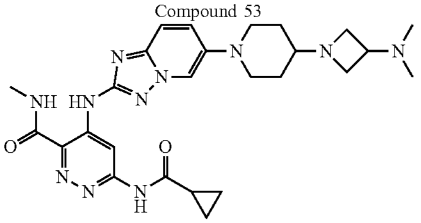 | 6-(cyclopropanecarboxamido)-4-((6-(4-(3-(dimethylamino)azetidin-1-yl)piperidin-1-yl)-[1,2,4]triazolo [1,5-a]pyridin-2-yl)amino)-N-methylpyridazine-3-carboxamide | $^1H$ NMR (400 MHz, DMSO-$d_6$) 12.03 (s, 1H), 11.39 (s, 1H), 9.30-9.34 (m, 2H), 8.22 (s, 1H), 7.57-7.67 (m, 2H), 3.74-4.09 (m, 5H), 2.87 (d, J = 3.9 Hz, 3H), 2.67-2.71 (m, 3H), 2.48-2.49 (m, 6H), 2.10-2.15 (m, 5H), 1.40-1.60 (m, 2H), 0.88-0.90 (m, 4H). MS (ESI) m/e $[M + H]^+$ = 534. |
| Example E22 | Compound 54 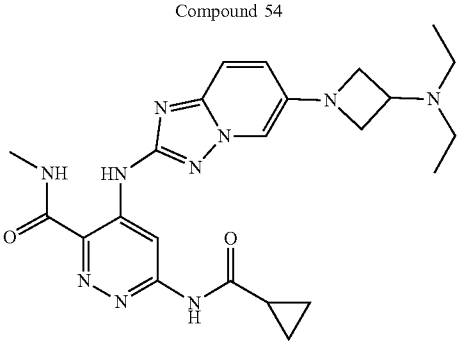 | 6-(cyclopropanecarboxamido)-4-((6-(3-(diethylamino)azetidin-1-yl)-[1,2,4]triazolo [1,5-a]pyridin-2-yl)amino)-N-methylpyridazine-3-carboxamide | $^1H$ NMR (400 MHz, DMSO-$d_6$) δ 12.02 (d, J = 20.6 Hz, 1H), 11.39 (s, 1H), 9.33 (d, J = 20.1 Hz, 2H), 8.08 (s, 0.6H), 7.89 (s, 0.4H), 7.61 (d, J = 25.0 Hz, 1H), 7.15 (d, J = 19.8 Hz, 1H), 4.32 (d, J = 55.1 Hz, 2H), 4.06 (s, 2H), 3.58 (s, 1H), 3.15 (s, 4H), 2.86 (s, 3H), 2.15 (s, 1H), 1.21 (s, 4H), 0.92 (d, J = 16.8 Hz, 6H). MS (ESI) m/e $[M + 1]^+$ = 479. |

Example F

Example F1: Synthesis of 6-(cyclopropanecarboxamido)-N-methyl-4-((6-(3-(N-methylmethylsulfonamido)azetidin-1-yl)-[1,2,4]triazolo[1,5-a]pyridin-2-yl)amino)pyridazine-3-carboxamide (Compound 16)

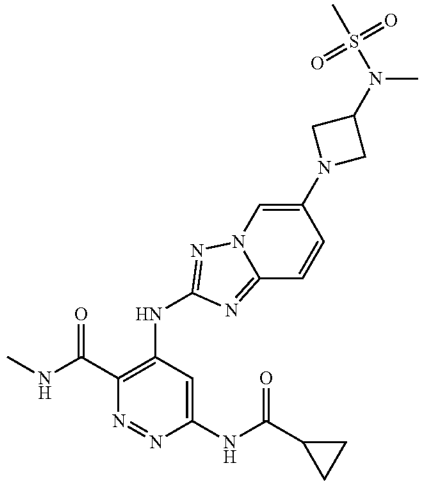

Step 1: Tert-butyl 3-(N-methylmethylsulfonamido) azetidine-1-carboxylate

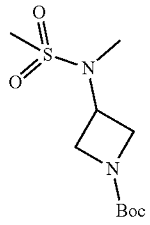 [SMILES: CN(C1CN(C(=O)OC(C)(C)C)C1)S(C)(=O)=O]

To a mixture of tert-butyl 3-(methylamino)azetidine-1-carboxylate (930 mg, 5 mmol) and $K_2CO_3$ (1380 mg, 10 mmol) in $CH_3CN$ (20 mL) was added methanesulfonyl chloride (575 mg, 5 mmol) and the resulting mixture was stirred at rt for 4 h. Upon completion of the reaction, the solid was removed by filtration and the filtrate was concentrated in vacuo to give the crude product as a white solid. It was used directly for next step without further purification. MS (ESI) m/e $[M+1]^+$=208.9.

Step 2: N-(azetidin-3-yl)-N-methylmethanesulfonamide

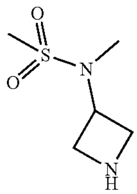

To a solution of tert-butyl 3-(N-methylmethylsulfonamido)azetidine-1-carboxylate (2.3 g, 8.5 mmol) in DCM (40 mL) was added TFA (4 mL) and the resulting solution was stirred at rt for 16 h. Upon completion of the reaction, the solvent was removed in vacuo and the residue was dissolved in DCM (50 mL), then $K2CO_3$ (1 g) was added and the resulting slurry was stirred at rt for 30 min, filtered and concentrated to give a product as yellow oil. (1.18 g, crude). MS (ESI) m/e $[M+1]^+$=164.9.

Step 3: N-(1-(2-amino-[1,2,4]triazolo[1,5-a]pyridin-6-yl)azetidin-3-yl)-N-methylmethanesulfonamide

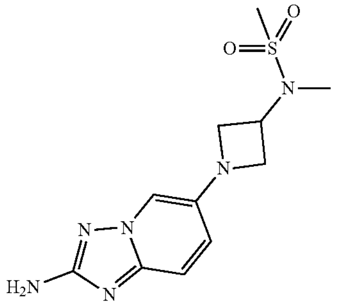 [SMILES: CN(C1CN(c2ccc3nc(N)nn3c2)C1)S(C)(=O)=O]

The desired compound was prepared from 6-bromo-[1,2,4]triazolo[1,5-a]pyridin-2-amine and N-(azetidin-3-yl)-N-methylmethanesulfonamide according to the procedure similar to that for compound 1 step 2 to give the product as yellow solid (yield: 193 mg, 71.4%). MS (ESI) m/e $[M+1]^+$=296.9.

Step 4: 6-chloro-N-methyl-4-((6-(3-(N-methylmethylsulfonamido)azetidin-1-yl)-[1,2,4]triazolo[1,5-a]pyridin-2-yl)amino)pyridazine-3-carboxamide

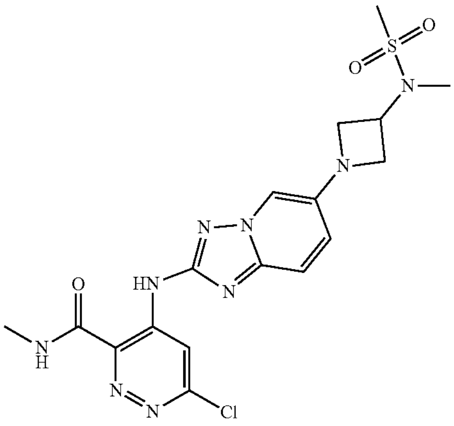

The desired compound was prepared from N-(1-(2-amino-[1,2,4]triazolo[1,5-a]pyridin-6-yl)azetidin-3-yl)-N-methylmethanesulfonamide and 4,6-dichloro-N-methylpyridazine-3-carboxamide according to the procedure similar to that for compound 7 step 3 to give the product as yellow solid (15 mg, 13.1%). MS (ESI) m/e $[M+1]^+$=465.8.

Step 5: 6-(cyclopropanecarboxamido)-4-((6-(3-(N-ethylmethylsulfonamido)azetidin-1-yl)-[1,2,4]triazolo[1,5-a]pyridin-2-yl)amino)-N-methylpyridazine-3-carboxamide (Compound 16)

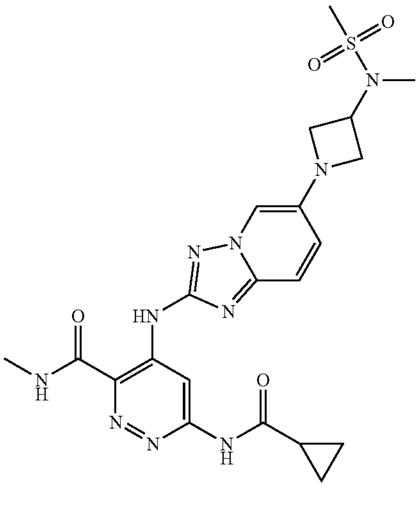

The desired compound was prepared from 6-chloro-N-methyl-4-((6-(3-(N-methylmethylsulfonamido)azetidin-1-yl)-[1,2,4]triazolo[1,5-a]pyridin-2-yl)amino)pyridazine-3-carboxamide according to the procedure similar to that for compound 1 step 2 to give the product (yield: 3 mg, 6.8%). MS (ESI) m/e $[M+1]^+$=514.9.

Example G

Example G1: Synthesis of 6-(cyclopropanecarboxamido)-4-((6-(3-(1-hydroxyethyl)azetidin-1-yl)-[1,2,4]triazolo[1,5-a]pyridin-2-yl)amino)-N-methylpyridazine-3-carboxamide (Compound 26)

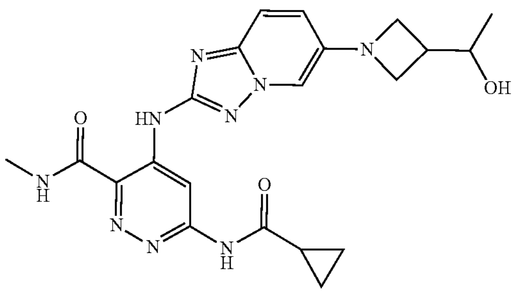 [SMILES: CNC(=O)c1nnc(NC(=O)C2CC2)cc1Nc1nc2ccc(N3CC(C(C)O)C3)cn2n1]

Step 1: 4-((6-(3-(1-((tert-butyldimethylsilyl)oxy)ethyl)azetidin-1-yl)-[1,2,4]triazolo[1,5-a]pyridin-2-yl)amino)-6-chloro-N-methylpyridazine-3-carboxamide

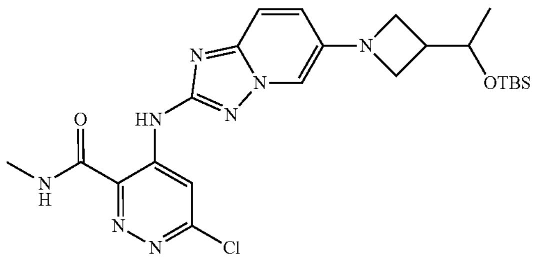 [SMILES: CNC(=O)c1nnc(Cl)cc1Nc1nc2ccc(N3CC(C(C)O[Si](C)(C)C(C)(C)C)C3)cn2n1]

To a solution of 6-(3-(1-((tert-butyldimethylsilyl)oxy)ethyl)azetidin-1-yl)-[1,2,4]triazolo[1,5-a]pyridin-2-amine (173 mg, 0.5 mmol) and 4,6-dichloro-N-methylpyridazine-3-carboxamide (205 mg, 1 mmol) in 5 mL of THF was added KHMDS (2 mL, 1M in THF) at room temperature, the resulting solution was stirred at room temperature for 2 h. Upon completion of the reaction, the solution was poured into 30 mL of water and the resulting mixture was extracted with DCM (10 mL×3). The combined organic layer was washed with 50 mL of water, dried over $Na_2SO_4$ and concentrated in vacuo. The crude product was washed with 10 mL of MeOH to give the product (100 mg, 39%) as a brown solid.

Step 2: 4-((6-(3-(1-((tert-butyldimethylsilyl)oxy)ethyl)azetidin-1-yl)-[1,2,4]triazolo[1,5-a]pyridin-2-yl)amino)-6-(cyclopropanecarboxamido)-N-methylpyridazine-3-carboxamide

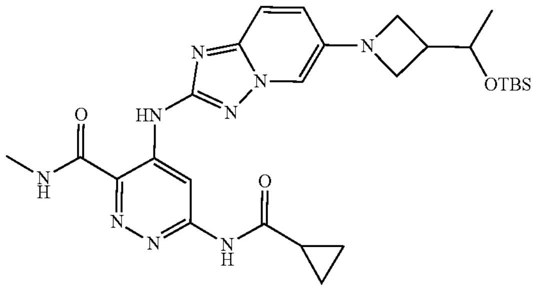 [SMILES: CNC(=O)c1nnc(NC(=O)C2CC2)cc1Nc1nc2ccc(N3CC(C(C)O[Si](C)(C)C(C)(C)C)C3)cn2n1]

The desired compound was prepared from 4-((6-(3-(1-((tert-butyldimethylsilyl)oxy)ethyl)azetidin-1-yl)-[1,2,4]triazolo[1,5-a]pyridin-2-yl)amino)-6-chloro-N-methylpyridazine-3-carboxamide according to the procedure similar to that for compound 1 step 2 to give the product (40 mg, 75%) as a white solid. MS (ESI) m/e $[M+1]^+$=565.9.

Step 3: 6-(cyclopropanecarboxamido)-4-((6-(3-(1-hydroxyethyl)azetidin-1-yl)-[1,2,4]triazolo[1,5-a]pyridin-2-yl)amino)-N-methylpyridazine-3-carboxamide

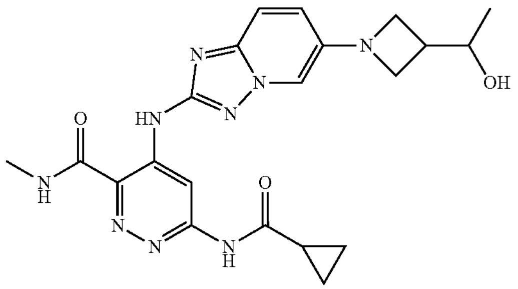 [SMILES: CNC(=O)c1nnc(NC(=O)C2CC2)cc1Nc1nc2ccc(N3CC(C(C)O)C3)cn2n1]

To a solution of 4-((6-(3-(1-((tert-butyldimethylsilyl)oxy)ethyl)azetidin-1-yl)-[1,2,4]triazolo[1,5-a]pyridin-2-yl)amino)-6-(cyclopropanecarboxamido)-N-methylpyridazine-3-carboxamide (30 mg, 0.05 mmol) in 3 mL of THF was added 1 mL of tetrabutylammonium fluoride and the resulting solution was stirred at room temperature for 24 h. Upon completion of the reaction, the solvent was removed in vacuo and the residue was purified by Prep-TLC (MeOH: DCM=1: 7) to give the product (10 mg, 44%) as a white solid. MS (ESI) m/e $[M+1]^+$=451.9. $^1H$ NMR (400 MHz, DMSO-$d_6$) δ 11.98 (s, 1H), 11.37 (s, 1H), 9.39-9.24 (m, 2H), 7.85 (s, 1H), 7.56 (d, J=9.4 Hz, 1H), 7.09 (d, J=9.4 Hz, 1H), 4.73 (d, J=4.9 Hz, 1H), 3.92-3.84 (m, 2H), 3.74 (dd, J=19.7, 6.1 Hz, 2H), 3.58 (s, 1H), 2.86 (d, J=4.7 Hz, 3H), 2.69-2.61 (m, 1H), 2.14 (d, J=4.6 Hz, 1H), 1.04 (d, J=6.1 Hz, 3H), 0.90 (d, J=9.9 Hz, 4H).

Example H

Example H1: Synthesis of 6-(cyclopropanecarboxamido)-4-((6-(3-hydroxyazetidin-1-yl)-[1,2,4]triazolo[1,5-a]pyridin-2-yl)amino)-N-methylpyridazine-3-carboxamide (Compound 27)

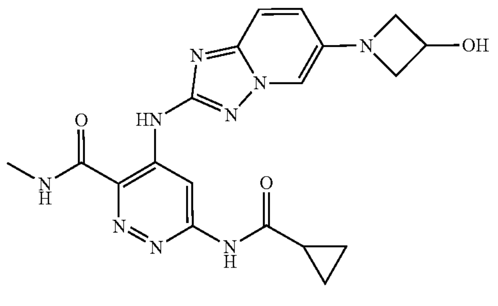 [SMILES: CNC(=O)c1nnc(NC(=O)C2CC2)cc1Nc1nc2ccc(N3CC(O)C3)cn2n1]

Step 1: 1-(6-nitropyridin-3-yl)azetidin-3-ol

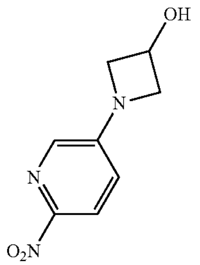 [SMILES: O=[N+]([O-])c1ccc(N2CC(O)C2)cn1]

A mixture of 5-bromo-2-nitropyridine (5 g, 24.6 mmol), azetidin-3-ol hydrochloride (4 g, 39.9 mmol) and $K_2CO_3$ (5 g, 36.9 mmol) in DMSO (100 mL) was stirred at 100° C. for 4 h.

Upon completion of the reaction, the mixture was poured into $H_2O$ (400 mL) and the resulting solution was extracted with EA (50 mL×3). The combined organic layer was dried over $Na_2SO_4$, filtered and concentrated to give the residue, which was purified by silica gel column chromatography (petroleum ether/EA=50:1 to 1:1) to give the product (2.3 g, 25.8%) as a yellow solid.

Step 2: 5-(3-((tert-butyldimethylsilyl)oxy)azetidin-1-yl)-2-nitropyridine

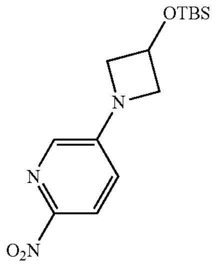 [SMILES: CC(C)(C)[Si](C)(C)OC1CN(c2ccc([N+](=O)[O-])nc2)C1]

To a solution of 1-(6-nitropyridin-3-yl)azetidin-3-ol (2.3 g, 11.8 mmol) and imidazole (3.21 g, 47.1 mmol) in DMF (20 mL) was added TBSCl (3.55 g, 23.6 mmol) and the resulting mixture was stirred at rt for 2 h. Upon completion of the reaction, $H_2O$ (30 mL) was added and the resulting mixture was extracted with EA (50 mL×3). The combined organic layer was dried over $Na_2SO_4$, filtered and concentrated to give the residue, which was purified by silica gel column chromatography (petroleum ether/EA=50:1 to 3:1) to give the product (2.8 g, 76.8%) as a yellow solid.

Step 3: 5-(3-((tert-butyldimethylsilyl)oxy)azetidin-1-yl)pyridin-2-amine

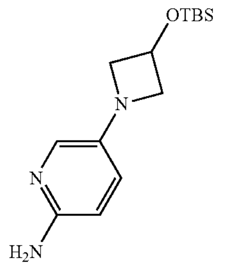

To a solution of 5-(3-((tert-butyldimethylsilyl)oxy)azetidin-1-yl)-2-nitro-pyridine (2.8 g, 9.1 mmol) in THE (300 mL) was added Raney Ni (1 g, wet) and the suspension was degassed under vacuum and purged with H2 for several times. The mixture was stirred under H2 (15 psi) atmosphere at rt for 4 h. Upon completion of the reaction, the catalyst was filtered off and the filtrate was concentrated to give the product (2.5 g, crude) as yellow solid, which was used for the next step without further purification.

Step 4: ethyl N-[(5-(3-[(tert-butyldimethylsilyl)oxy]azetidin-1-yl)pyridin-2-yl)carbamothioyl]carbamate

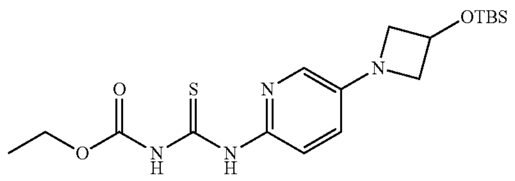 [SMILES: CCOC(=O)NC(=S)Nc1ccc(N2CC(O[Si](C)(C)C(C)(C)C)C2)cn1]

A solution of 5-(3-((tert-butyldimethylsilyl)oxy)azetidin-1-yl)pyridin-2-amine (2.5 g, crude) and O-ethyl carbonisothiocyanatidate (1.4 g, 10.7 mmol) in dioxane (50 mL) was stirred at 60° C. for 12 h. After cooled to room temperature, the solution was removed in vacuo to give the product (3.67 g, crude) as red oil.

Step 5: 6-(3-((tert-butyldimethylsilyl)oxy)azetidin-1-yl)-[1,2,4]triazolo[1,5-a]pyridin-2-amine

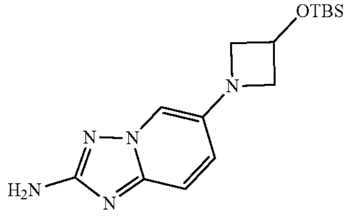 [SMILES: CC(C)(C)[Si](C)(C)OC1CN(c2ccc3nc(N)nn3c2)C1]

The desired compound was prepared from ethyl N-[(5-(3-[(tert-butyldimethylsilyl)oxy]azetidin-1-yl)pyridin-2-yl)carbamothioyl]carbamate according to the procedure similar to that for compound 11 step 4 to give the product (1.5 g, 52.4% yield) as an off-white solid. $^1$H NMR (400 MHz, DMSO-$d_6$) δ ppm 0.07 (s, 6H), 0.87 (s, 9H) 3.46 (d, J=7.63, 5.25 Hz, 2H) 4.10 (t, J=7.07 Hz, 2H) 4.73 (q, J=5.57 Hz, 1H), 5.68 (s, 2H) 6.87 (dd, J=9.32 Hz, 1H) 7.21 (d, J=9.26 Hz, 1H) 7.73 (s, 1H). MS (ESI) m/e [M+1]$^+$=320.2.

Step 6: 4-((6-(3-((tert-butyldimethylsilyl)oxy)azetidin-1-yl)-[1,2,4]triazolo[1,5-a]pyridin-2-yl)amino)-6-chloro-N-methylpyridazine-3-carboxamide

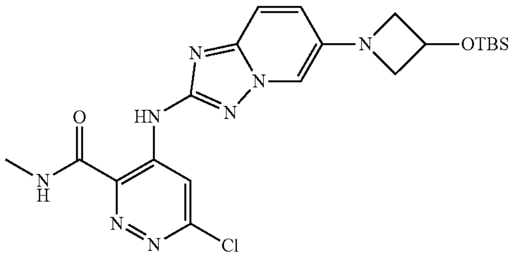 [SMILES: CNC(=O)c1nnc(Cl)cc1Nc1nc2ccc(N3CC(O[Si](C)(C)C(C)(C)C)C3)cn2n1]

The desired compound was prepared from 4,6-dichloro-N-methylpyridazine-3-carboxamide and 6-(3-((tert-butyldimethylsilyl)oxy)azetidin-1-yl)-[1,2,4]triazolo[1,5-a]pyridin-2-amine according to the procedure similar to that for compound 1 step 1 to give the product (50 mg, 32%) as an off-white solid. MS (ESI) m/e [M+1]$^+$=488.9.

Step 7: 6-(cyclopropanecarboxamido)-4-((6-(3-hydroxyazetidin-1-yl)-[1,2,4]triazolo[1,5-a]pyridin-2-yl)amino)-N-methylpyridazine-3-carboxamide

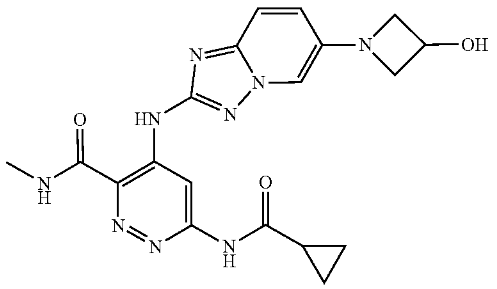 [SMILES: CNC(=O)c1nnc(NC(=O)C2CC2)cc1Nc1nc2ccc(N3CC(O)C3)cn2n1]

The desired compound was prepared from 4-((6-(3-((tert-butyldimethylsilyl)oxy)azetidin-1-yl)-[1,2,4]triazolo[1,5-a]pyridin-2-yl)amino)-6-chloro-N-methylpyridazine-3-carboxamide according to the procedure similar to that for compound 1 step 2 to give the product (6 mg, 13.8%). $^1$H NMR (400 MHz, DMSO-$d_6$) δ 11.99 (s, 1H), 11.37 (s, 1H), 9.34 (s, 1H), 9.29 (m, 1H), 7.91 (d, J=1.9 Hz, 1H), 7.56 (d, J=9.4 Hz, 1H), 7.11 (dd, J=9.5, 2.0 Hz, 1H), 5.68 (d, J=6.5 Hz, 1H), 4.58 (m, 1H), 4.13 (t, J=7.1 Hz, 2H), 3.56 (dd, J=7.6, 5.2 Hz, 2H), 2.87 (d, J=4.7 Hz, 3H), 2.14 (m, 1H), 1.01-0.81 (m, 4H). MS (ESI) m/e [M+1]$^+$=424.4.

Example J

Example J1: Synthesis of 6-(cyclopropanecarboxamido)-4-((6-(3-fluoro-3-(hydroxymethyl)azetidin-1-yl)-[1,2,4]triazolo[1,5-a]pyridin-2-yl)amino)-N-methylpyridazine-3-carboxamide (Compound 32)

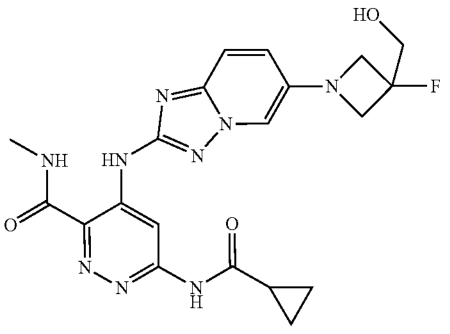 [SMILES: CNC(=O)c1nnc(NC(=O)C2CC2)cc1Nc1nc2ccc(N3CC(F)(CO)C3)cn2n1]

Step 1: (3-fluoro-1-(6-nitropyridin-3-yl)azetidin-3-yl)methanol

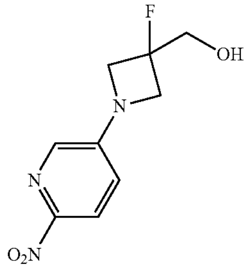 [SMILES: O=[N+]([O-])c1ccc(N2CC(F)(CO)C2)cn1]

To a solution of (3-fluoroazetidin-3-yl)methanol hydrochloride (680 mg, 4.8 mmol) in 1,4-dioxane (5 mL) were added DIEA (2.48 g, 19.2 mmol) and 5-fluoro-2-nitropyridine (682 mg, 19.2 mmol) at rt. The resulting mixture was stirred at 80° C. for 15 h under $N_2$. After cooled to room temperature, the solvent was removed in vacuo and the residue was purified by silica gel column chromatography (petroleum ether:EA=1:1) to give the product (700 mg, 64% yield) as a yellow solid. $^1$H NMR (DMSO-$d_6$) δ 8.17-8.19 (d, J=8 Hz, 1H) 7.79-7.80 (d, J=4 Hz, 1H) 7.03-7.06 (m, 1H) 5.37-5.40 (t, J=12 Hz, 1H) 4.16-4.27 (m, 4H) 3.33-3.78 (m, 2H).

Step 2: 5-(3-(((tert-butyldimethylsilyl)oxy)methyl)-3-fluoroazetidin-1-yl)-2-nitropyridine

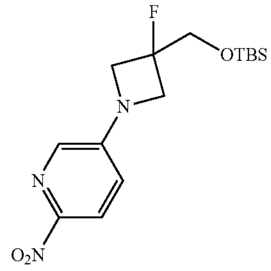

The desired compound was prepared from (3-fluoro-1-(6-nitropyridin-3-yl)azetidin-3-yl)methanol according to the procedure similar to that for compound 27 step 2 to give the product (750 mg, 71.3%) as a yellow solid. $^1$H NMR ($CDCl_3$) δ 8.15-8.17 (d, J=8 Hz, 1H), 7.68-7.69 (d, J=2.8 Hz, 1H), 6.76-6.79 (m, 1H), 4.14-4.26 (m, 4H), 3.87-3.91 (m, 4H), 0.855 (s, 9H), 0.088 (s, 6H).

Step 3: 5-(3-(((tert-butyldimethylsilyl)oxy)methyl)-3-fluoroazetidin-1-yl)pyridin-2-amine

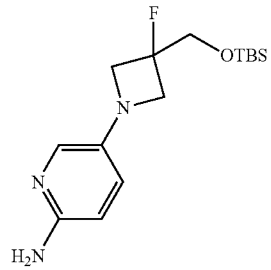 [SMILES: CC(C)(C)[Si](C)(C)OCC1(F)CN(c2ccc([N+](=O)[O-])nc2)C1]

The desired compound was prepared from 5-(3-(((tert-butyldimethylsilyl)oxy)methyl)-3-fluoroazetidin-1-yl)-2-nitropyridine according to the procedure similar to that for compound 27 step 3 to give the product (600 mg, crude) as a gray solid, which was used to the next step without further purification.

Step 4: ethyl N-([5-(3-([(tert-butyldimethylsilyl)oxy]methyl)-3-fluoroazetidin-1-yl)pyridin-2-yl]carbamothioyl)carbamate

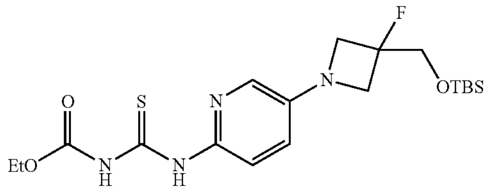 [SMILES: CCOC(=O)NC(=S)Nc1ccc(N2CC(F)(CO[Si](C)(C)C(C)(C)C)C2)cn1]

The desired compound was prepared from 5-(3-(((tert-butyldimethylsilyl)oxy)methyl)-3-fluoroazetidin-1-yl)pyridin-2-amine according to the procedure similar to that for Compound 6 in Example B1 step 1 to give the product (800 mg, crude) as a brown solid, which was used to the next step without further purification.

Step 5: 6-(3-(((tert-butyldimethylsilyl)methyl)-3-fluoroazetidin-1-yl)-[1,2,4]triazolo[1,5-a]pyridin-2-amine

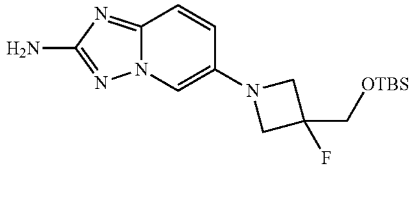 [SMILES: CC(C)(C)[Si](C)(C)OCC1(F)CN(c2ccc3nc(N)nn3c2)C1]

To a solution of ethyl N-([5-(3-([(tert-butyldimethylsilyl) oxy]methyl)-3-fluoro-azetidin-1-yl)pyridin-2-yl]carbamothioyl)carbamate (800 mg, 2.28 mmol) in MeOH/EtOH (v:v=1:1, 8 mL) were added DIEA (882 mg, 6.83 mmol) and $NH_2OH$ HCl (790 mg, 11.38 mmol) at rt. The resulting mixture was stirred at 80° C. for 15 h under $N_2$ atmosphere. After cooled to room temperature, water (5 mL) was added and the resulting solution was extracted with DCM/MeOH (v:v=3:1, 16 mL). The combined organic layer was washed with brine, dried over $Na_2SO_4$ and concentrated in vacuo. The residue was purified by silica gel column chromatography (EA: THF=1:1) to give the product (360 mg, 66.7%) as a light red solid. $^1$H NMR (DMSO-$d_6$) δ 7.77 (s, 1H), 7.15-7.17 (d, J=9.2 Hz, 1H), 6.85-6.87 (m, 1H), 5.64 (s, 2H), 3.82-3.92 (m, 4H), 3.71-3.78 (m, 2H), 0.783 (s, 9H), 0.00 (s, 6H). MS (ESI) m/e $[M+1]^+$=352.2.

Step 6: 4-((6-(3-(((tert-butyldimethylsilyl)oxy) methyl)-3-fluoroazetidin-1-yl)-[1,2,4]triazolo[1,5-a] pyridin-2-yl)amino)-6-chloro-N-methylpyridazine-3-carboxamide

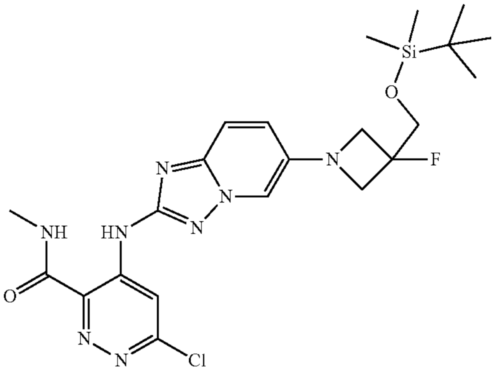 [SMILES: CNC(=O)c1nnc(Cl)cc1Nc1nc2ccc(N3CC(F)(CO[Si](C)(C)C(C)(C)C)C3)cn2n1]

The desired compound was prepared from 4,6-dichloro-N-methylpyridazine-3-carboxamide and 6-(3-(((tert-butyldimethylsilyl)oxy)methyl)-3-fluoroazetidin-1-yl)-[1,2,4]triazolo[1,5-a]pyridin-2-amine according to the procedure similar to that for compound 7 step 3 to give the product (56 mg, 37%) as a yellow solid. MS (ESI) m/e $[M+1]^+$=520.8.

Step 7: 4-((6-(3-(((tert-butyldimethylsilyl)oxy) methyl)-3-fluoroazetidin-1-yl)-[1,2,4]triazolo[1,5-a] pyridin-2-yl)amino)-6-(cyclopropanecarboxamido)-N-methylpyridazine-3-carboxamide

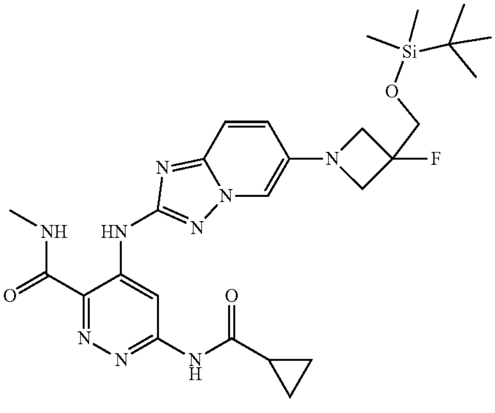 [SMILES: CNC(=O)c1nnc(NC(=O)C2CC2)cc1Nc1nc2ccc(N3CC(F)(CO[Si](C)(C)C(C)(C)C)C3)cn2n1]

The desired compound was prepared from 4-((6-(3-(((tert-butyldimethylsilyl)oxy)methyl)-3-fluoroazetidin-1-yl)-[1,2,4]triazolo[1,5-a]pyridin-2-yl)amino)-6-chloro-N-methylpyridazine-3-carboxamide and cyclopropanecarboxamide according to the procedure similar to that for compound 1 step 2 to give the product (47 mg, 74%) as a yellow solid. $^1$H NMR (DMSO-$d_6$) δ 12.01 (s, 1H), 11.38 (s, 1H), 9.42-9.24 (m, 2H), 8.07 (s, 1H), 7.59 (d, J=9.4 Hz, 1H), 7.19 (d, J=7.7 Hz, 1H), 4.08-3.90 (m, 6H), 2.87 (d, J=4.6 Hz, 3H), 2.14 (s, 1H), 1.23 (s, 6H), 0.9-0.84 (m, 13H). MS (ESI) m/e $[M+1]^+$=570.6.

Step 8: 6-(cyclopropanecarboxamido)-4-((6-(3-fluoro-3-(hydroxymethyl)azetidin-1-yl)-[1,2,4]triazolo[1,5-a]pyridin-2-yl)amino)-N-methylpyridazine-3-carboxamide (Compound 32)

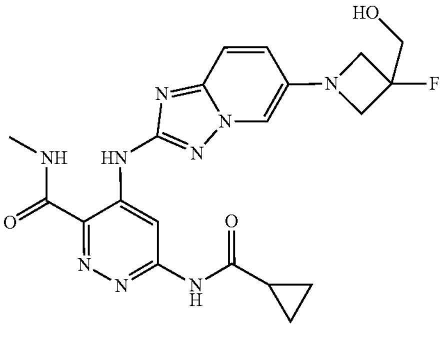 [SMILES: CNC(=O)c1nnc(NC(=O)C2CC2)cc1Nc1nc2ccc(N3CC(F)(CO)C3)cn2n1]

To a solution of 4-((6-(3-(((tert-butyldimethylsilyl)oxy) methyl)-3-fluoroazetidin-1-yl)-[1,2,4]triazolo[1,5-a]pyridin-2-yl)amino)-6-(cyclopropanecarboxamido)-N-methylpyridazine-3-carboxamide (47 mg, 0.082 mmol) in DCM (200 mL) was added TBAF (2 mL, 1 mol/L) and the resulting solution was stirred at rt for overnight. Upon completion of the reaction, the solvent was removed in vacuo and the residue was purified by pre-TLC (MeOH:

DCM=1:20) to give the desired product (5 mg, 13%). $^1H$ NMR (DMSO-$d_6$) δ 12.01 (s, 1H), 11.37 (s, 1H), 9.38-9.21 (m, 2H), 8.04 (s, 1H), 7.60 (d, J=9.4 Hz, 1H), 7.18 (dd, J=9.4, 1.7 Hz, 1H), 4.09-4.02 (m, 2H), 3.95-.3.88 (m, 2H), 3.76 (s, 1H), 3.70 (s, 1H), 2.87 (d, J=4.6 Hz, 3H), 2.17-2.11 (m, 1H), 0.96-0.82 (m, 4H).

| Example | Compound | Name | $^1H$ NMR data LC/MS m/z (M + 1) |
|---|---|---|---|
| Example J2 | Compound 36 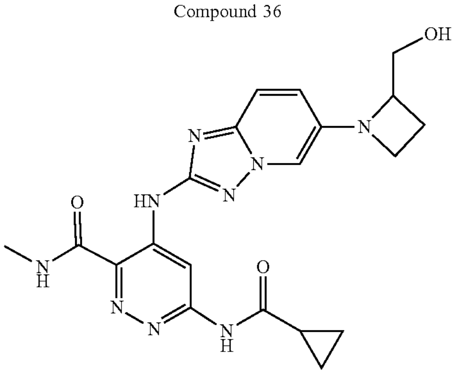 | 6-(cyclopropanecarboxamido)-4-((6-(2-(hydroxymethyl) azetidin-1-yl)-[1,2,4] triazolo[1,5-a] pyridin-2-yl) amino)-N-methylpyridazine-3-carboxamide | $^1H$ NMR (400 MHz, DMSO-$d_6$) δ 11.99 (s, 1H), 11.36 (s, 1H), 9.38-9.24 (m, 2H), 8.08 (s, 1H), 7.55 (d, J = 9.4 Hz, 1H), 7.32 (d, J = 8.2 Hz, 1H), 5.18 (s, 1H), 4.06 (s, 1H), 3.91 (s, 1H), 3.65 (s, 2H), 3.59 (d, J = 7.8 Hz, 1H), 2.87 (d, J = 4.4 Hz, 3H), 2.26 (d, J = 8.9 Hz, 1H), 2.13 (d, J = 7.7 Hz, 2H), 0.97-0.83 (m, 4H). MS (ESI) m/e $[M + 1]^+$ = 438. |

To a solution of 4,6-dichloro-N-methylpyridazine-3-carboxamide (1.16 g, 5.6 mmol) and 6-bromo-[1,2,4]triazolo[1,5-a]pyridin-2-amine (1 g, 4.7 mmol) in THE (20 mL) was added LiHMDS (1M in THF, 11.75 mL, 11.75 mmol) at rt and the resulting mixture was stirred at this temperature for 1 h. Upon completion of the reaction, water was added and the resulting solution was extracted with EA (10 mL×3). The combined organic layer was concentrated in vacuo and the residue was recrystallized in MeOH to give the product as a white solid (820 mg, 45.6%). MS (ESI) m/e $[M+1]^+$=381.8.

Example K

Example K1: Synthesis of 6-(cyclopropanecarboxamido)-N-methyl-4-((6-(2-oxo-4-phenylazetidin-1-yl)-[1,2,4]triazolo[1,5-a]pyridin-2-yl)amino) pyridazine-3-carboxamide (Compound 38)

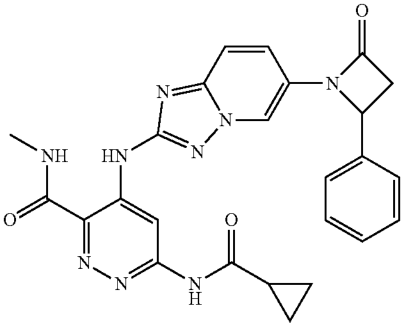 [SMILES: CNC(=O)c1nnc(NC(=O)C2CC2)cc1Nc1nc2ccc(N3C(=O)CC3c3ccccc3)cn2n1]

Step 1: 4-((6-bromo-[1,2,4]triazolo[1,5-a]pyridin-2-yl)amino)-6-chloro-N-methylpyridazine-3-carboxamide

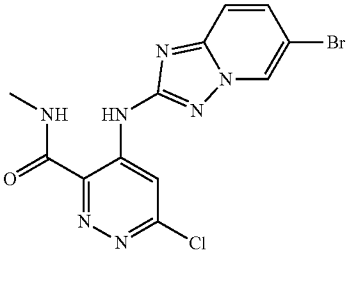 [SMILES: CNC(=O)c1nnc(Cl)cc1Nc1nc2ccc(Br)cn2n1]

Step 2: 6-chloro-N-methyl-4-((6-(2-oxo-4-phenylazetidin-1-yl)-[1,2,4]triazolo[1,5-a]pyridin-2-yl) amino)pyridazine-3-carboxamide

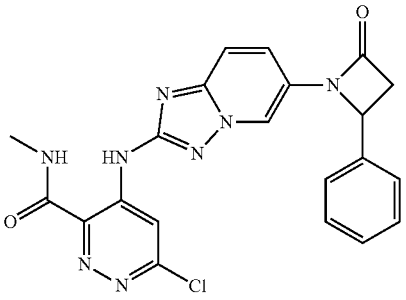 [SMILES: CNC(=O)c1nnc(Cl)cc1Nc1nc2ccc(N3C(=O)CC3c3ccccc3)cn2n1]

A mixture of 4-((6-bromo-[1,2,4]triazolo[1,5-a]pyridin-2-yl)amino)-6-chloro-N-methylpyridazine-3-carboxamide (380 mg, 1 mmol), 4-phenylazetidin-2-one (294 mg, 2 mmol), $Pd_2(dba)_3$ (274.5 mg, 0.3 mmol), XantPhos (346.8 mg, 0.6 mmol) and $Cs_2CO_3$ (652 mg, 2 mmol) in dioxane (10 mL) was stirred at 100° C. for 2 h under $N_2$ atmosphere. After cooled to room temperature, the solid was filtered off the filtrate was concentrated in vacuo. The residue was purified by pre-TLC (DCM:MeOH=15:1) to give the desired product (270 mg, 60% purity) as a brown solid. MS (ESI) m/e $[M+1]^+$=448.9.

Step 3: 6-(cyclopropanecarboxamido)-N-methyl-4-((6-(2-oxo-4-phenylazetidin-1-yl)-[1,2,4]triazolo[1,5-a]pyridin-2-yl)amino)pyridazine-3-carboxamide (Compound 38)

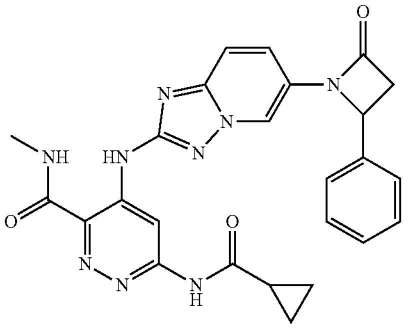 [SMILES: CNC(=O)c1nnc(NC(=O)C2CC2)cc1Nc1nc2ccc(N3C(=O)CC3c3ccccc3)cn2n1]

A mixture of 6-chloro-N-methyl-4-((6-(2-oxo-4-phenylazetidin-1-yl)-[1,2,4]triazolo[1,5-a]pyridin-2-yl)amino) pyridazine-3-carboxamide (200 mg, 0.45 mmol), cyclopropanecarboxamide (189.4 mg, 2.23 mmol), $Pd_2(dba)_3$ (128.1 mg, 0.14 mmol), XantPhos (161.8 mg, 0.28 mmol) and $Cs_2CO_3$ (368.4 mg, 1.13 mmol) in dioxane (7 mL) was stirred at 140° C. for 4 h under $N_2$ atmosphere. After cooled to room temperature, the solid was filtered off the filtrate was concentrated. The residue was purified by pre-TLC (DCM: MeOH=10:1) to give the desired product (17.57 mg, 7.85%). $^1$H NMR (400 MHz, DMSO-$d_6$) δ 12.12 (s, 1H), 11.41 (s, 1H), 9.37 (s, 1H), 9.32 (d, J=4.7 Hz, 1H), 8.64 (s, 1H), 7.67 (d, J=18.1 Hz, 2H), 7.52 (d, J=7.3 Hz, 2H), 7.46-7.26 (m, 3H), 5.40 (d, J=3.0 Hz, 1H), 3.70 (d, J=15.3, 5.6 Hz, 1H), 3.05 (s, 2H), 2.86 (d, J=4.6 Hz, 3H), 2.14 (d, J=4.7 Hz, 1H), 0.99-0.80 (m, 4H).

MS (ESI) m/e $[M+1]^+$=498.5.

Example L

Example L1: Synthesis of 6-(cyclopropanecarboxamido)-N-methyl-4-((6-(1-(methylsulfonyl)azetidin-3-yl)-[1,2,4]triazolo[1,5-a]pyridin-2-yl)amino) pyridazine-3-carboxamide (Compound 39)

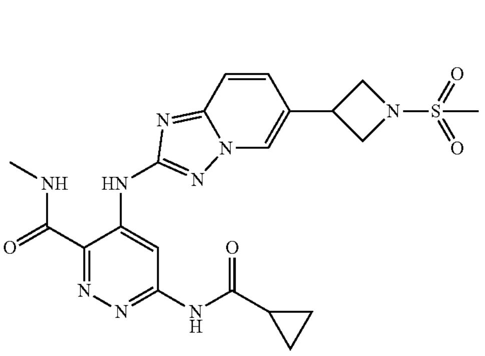 [SMILES: CNC(=O)c1nnc(NC(=O)C2CC2)cc1Nc1nc2ccc(C3CN(S(C)(=O)=O)C3)cn2n1]

Step 1: tert-butyl 3-(6-aminopyridin-3-yl)azetidine-1-carboxylate

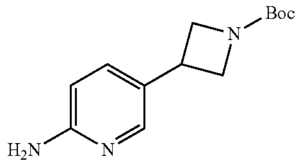 [SMILES: CC(C)(C)OC(=O)N1CC(c2ccc(N)nc2)C1]

The mixture of 5-(4,4,5,5-tetramethyl-1,3,2-dioxaborolan-2-yl)pyridin-2-amine (7 g, 31.80 mmol), tert-butyl 3-iodoazetidine-1-carboxylate (7.21 g, 25.40 mmol), $Pd(PPh_3)_4$ (1.83 g, 1.54 mmol), $K_3PO_4$ (13.3 g, 63.56 mmol) in DMF (105 mL) and $H_2O$ (7 mL) was stirred at 60° C. for 12 h. After cooled to room temperature, the mixture was poured into $H_2O$ (200 mL) and the resulting solution was extracted with EA (50 mL×2). The combined organic layer was washed with brine, dried over $Na_2SO_4$, filtered and concentrated. The residue was purified by silica gel column chromatography (petroleum ether: EA=5:1-1:2) to afford the product (4.5 g, 71%) as a yellow solid.

Step 2: tert-butyl 3-(6-(3-(ethoxycarbonyl)thioureido)pyridin-3-yl)azetidine-1-carboxylate

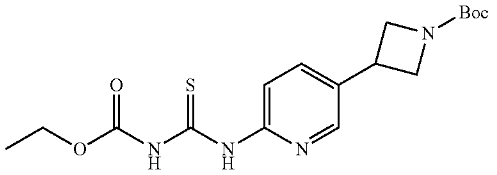 [SMILES: CCOC(=O)NC(=S)Nc1ccc(C2CN(C(=O)OC(C)(C)C)C2)cn1]

The desired compound was prepared from tert-butyl 3-(6-aminopyridin-3-yl)azetidine-1-carboxylate according to the procedure similar to that for compound 6 step 1 to give the product (6.9 g, crude) as brown solid.

Step 3: tert-butyl 3-(2-amino-[1,2,4]triazolo[1,5-a] pyridin-6-yl)azetidine-1-carboxylate

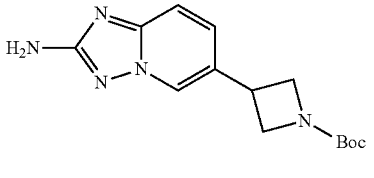 [SMILES: CC(C)(C)OC(=O)N1CC(c2ccc3nc(N)nn3c2)C1]

The desired compound was prepared from tert-butyl 3-(6-(3-(ethoxycarbonyl)thioureido)pyridin-3-yl)azetidine-1-carboxylate according to the procedure similar to that for compound 11 step 4 to give the product (4.2 g, 14.5 mmol, 80%) as a white solid. $^1$H NMR (DMSO-$d_6$) δ 8.52 (s, 1H), 7.48 (d, J=9.01 Hz, 1H), 7.36 (d, J=9.38 Hz, 1H) 5.94 (s, 2H) 4.23 (t, J=6.94 Hz, 2H) 3.80-3.93 (m, 3H) 1.41 (s, 9H). MS (ESI) m/e $[M+1]^+$=290.2.

Step 3: tert-butyl 3-(2-((6-chloro-3-(methylcarbamoyl)pyridazin-4-yl)amino)-[1,2,4]triazolo[1,5-a]pyridin-6-yl)azetidine-1-carboxylate

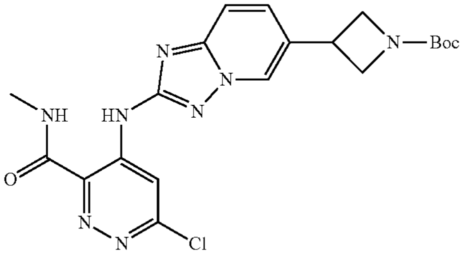 [SMILES: CNC(=O)c1nnc(Cl)cc1Nc1nc2ccc(C3CN(C(=O)OC(C)(C)C)C3)cn2n1]

The desired compound was prepared from tert-butyl 3-(2-amino-[1,2,4]triazolo[1,5-a]pyridin-6-yl)azetidine-1-carboxylate and 2,4-dichloro-N-methylbenzamide according to the procedure similar to that for compound 7 step 3 to give the product (260 mg, 26%) as a yellow solid. MS (ESI) m/e $[M+H]^+$=459.

Step 4: tert-butyl 3-(2-((6-(cyclopropanecarboxamido)-3-(methylcarbamoyl)pyridazin-4-yl)amino)-[1,2,4]triazolo[1,5-a]pyridin-6-yl)azetidine-1-carboxylate

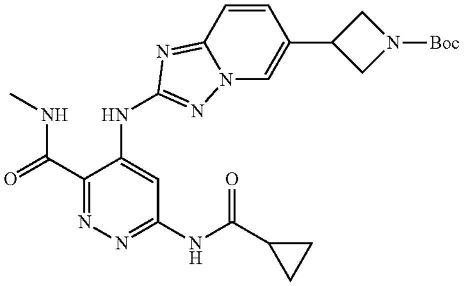 [SMILES: CNC(=O)c1nnc(NC(=O)C2CC2)cc1Nc1nc2ccc(C3CN(C(=O)OC(C)(C)C)C3)cn2n1]

The desired compound was prepared from tert-butyl 3-(2-((6-chloro-3-(methylcarbamoyl)pyridazin-4-yl)amino)-[1,2,4]triazolo[1,5-a]pyridin-6-yl)azetidine-1-carboxylate according to the procedure similar to that for Example A1, compound1, step 2 to give the product (110 mg, 42%) as a yellow solid. $^1$H NMR (400 MHz, DMSO-$d_6$) 12.12 (s, 1H), 11.41 (s, 1H), 9.41 (s, 1H), 9.33 (d, 1H), 8.82 (s, 1H), 7.71-7.77 (m, 2H), 4.26-4.27 (m, 2H), 3.95-3.96 (m, 3H), 2.87 (d, 3H), 2.15-2.16 (m, 1H), 1.42 (s, 9H), 0.89-0.91 (m, 4H). MS (ESI) m/e $[M+H]^+$=508.

Step 5: 4-((6-(azetidin-3-yl)-[1,2,4]triazolo[1,5-a]pyridin-2-yl)amino)-6-(cyclopropanecarboxamido)-N-methylpyridazine-3-carboxamide hydrochloride

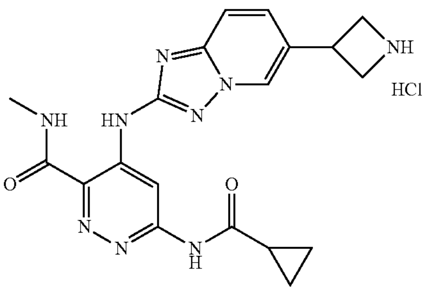 [SMILES: CNC(=O)c1nnc(NC(=O)C2CC2)cc1Nc1nc2ccc(C3CNC3)cn2n1 ; Cl]

To a solution of tert-butyl 3-(2-((6-(cyclopropanecarboxamido)-3-(methylcarbamoyl)pyridazin-4-yl)amino)-[1,2,4]triazolo[1,5-a]pyridin-6-yl)azetidine-1-carboxylate (14 mg, 0.02 mmol) in DCM (2 mL) was added TFA (0.2 mL) and the resulting mixture was stirred at rt for 2 h. Upon completion of the reaction, the solvent was removed in vacuo and the residue was lyophilized with a few drops of 0.5 M HCl to give the product (12 mg, 99%) as a yellow semi-solid. $^1$H NMR (400 MHz, DMSO-$d_6$) 12.17 (s, 1H), 11.45 (s, 1H), 8.95-9.40 (m, 5H), 7.77-7.86 (m, 2H), 4.18-4.27 (m, 5H), 2.87 (d, 3H), 2.14-2.17 (m, 1H), 0.89-0.91 (m, 4H).MS (ESI) m/e $[M+H]^+$=408.

Step 6: 6-(cyclopropanecarboxamido)-N-methyl-4-((6-(1-(methylsulfonyl)azetidin-3-yl)-[1,2,4]triazolo[1,5-a]pyridin-2-yl)amino)pyridazine-3-carboxamide (Compound 39)

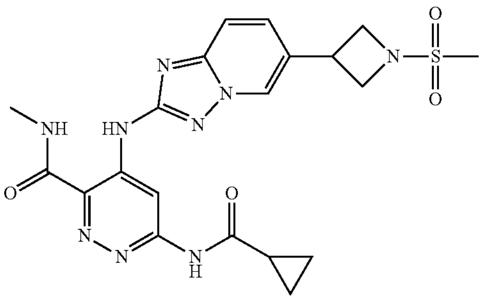 [SMILES: CNC(=O)c1nnc(NC(=O)C2CC2)cc1Nc1nc2ccc(C3CN(S(C)(=O)=O)C3)cn2n1]

The desired compound was prepared from 4-((6-(azetidin-3-yl)-[1,2,4]triazolo[1,5-a]pyridin-2-yl)amino)-6-(cyclopropanecarboxamido)-N-methylpyridazine-3-carboxamide hydrochloride according to the procedure similar to that for compound 7 step 5 to give the product (2.22 mg, 31%). $^1$H NMR (400 MHz, DMSO-$d_6$) 12.15 (s, 1H), 11.43 (s, 1H), 9.40 (s, 1H), 9.33 (d, 1H), 8.85 (s, 1H), 7.74-7.80 (i, 2H), 4.23-4.24 (m, 2H), 4.40-4.45 (m, 3H), 3.11 (s, 3H), 2.87 (d, 3H), 2.15-2.16 (m, 1H), 0.0.89-0.92 (m, 4H). MS (ESI) m/e $[M+H]^+$=486.

Compounds 42-43, 48-50 below were synthesized starting from the corresponding starting materials according to the similar procedures described as those of compound 39.

| Example | Compound | Name | $^1$H NMR data LC/MS m/z (M + 1) |
| --- | --- | --- | --- |
| Example L2 | Compound 42 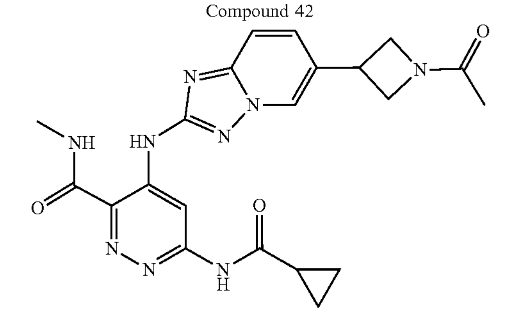 | 4-((6-(1-acetylazetidin-3-yl)-[1,2,4]triazolo[1,5-a]pyridin-2-yl)amino)-6-(cyclopropanecarboxamido)-N-methylpyridazine-3-carboxamide | $^1$H NMR (400 MHz, DMSO-$d_6$) 12.13 (s, 1H), 11.42 (s, 1H), 9.41 (s, 1H), 9.33 (d, 1H), 8.86 (s, 1H), 7.72-7.80 (m, 2H), 4.50 (t, 1H), 4.24 (t, 2H), 4.01-4.02 (m, 1H), 3.88-3.92 (m, 2H), 2.87 (d, 3H), 2.15-2.16 (m, 1H), 1.81 (s, 3H), 0.89-0.92 (m, 4H). MS (ESI) m/e $[M + H]^+$ = 450. |
| Example L3 | Compound 43 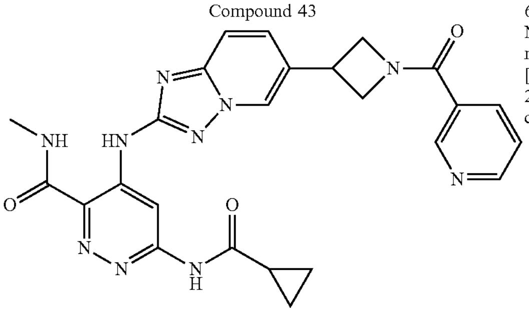 | 6-(cyclopropanecarboxamido)-N-methyl-4-((6-(1-nicotinoylazetidin-3-yl)-[1,2,4]triazolo[1,5-a]pyridin-2-yl)amino)pyridazine-3-carboxamide | $^1$H NMR (400 MHz, DMSO-$d_6$) 12.13 (s, 1H), 11.42 (s, 1H), 9.40 (s, 1H), 9.33 (d, J = 5.1 Hz, 1H), 8.91 (d, J = 11.5 Hz, 2H), 8.71 (d, J = 3.3 Hz, 1H), 8.10 (d, J = 7.8 Hz, 1H), 7.86 (d, J = 9.1 Hz, 1H), 7.73 (d, J = 9.1 Hz, 1H), 7.50-7.53 (m, 1H), 4.70 (d, J = 7.8 Hz, 1H), 4.51-4.57 (m, 2H), 4.14 (d, J = 5.7 Hz, 2H), 2.87 (d, J = 4.7 Hz, 3H), 2.15-2.16 (m, 1H), 0.88-0.90 (m, 4H). MS (ESI) m/e $[M + H]^+$ = 513. |
| Example L4 | Compound 48 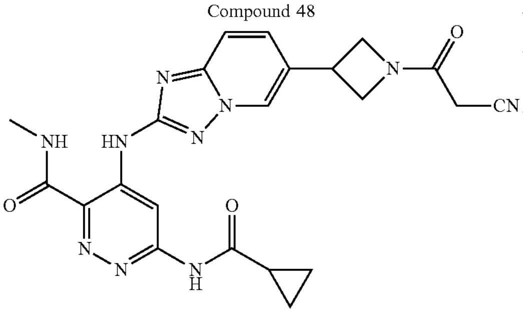 | 4-((6-(1-(2-cyanoacetyl) azetidin-3-yl)-[1,2,4] triazolo [1,5-a]pyridin-2-yl)amino)-6-(cyclopropanecarboxamido)-N-methylpyridazine-3-carboxamide | $^1$H NMR (400 MHz, DMSO-$d_6$) 12.14 (s, 1H), 11.42 (s, 1H), 9.40 (s, 1H), 9.33 (d, J = 4.1 Hz, 1H), 8.88 (s, 1H), 7.82 (d, J = 9.1 Hz, 1H), 7.74 (d, J = 9.0 Hz, 1H), 4.53 (t, J = 8.6 Hz, 1H), 4.26-4.31 (m, 2H), 3.96-4.08 (m, 2H), 3.79 (s, 2H), 2.87 (d, J = 3.7 Hz, 3H), 2.15-2.16 (m, 1H), 0.89-0.91 (m, 4H). MS (ESI) m/e $[M + H]^+$ = 475. |
| Example L5 | Compound 49 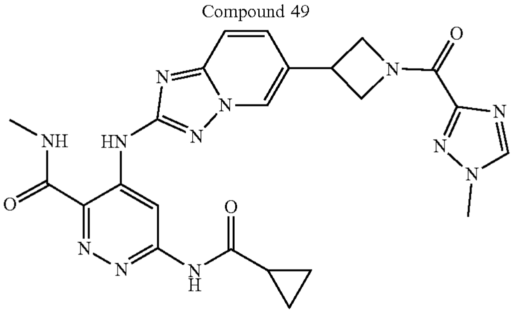 | 6-(cyclopropanecarboxamido)-N-methyl-4-((6-(1-(1-methyl-1H-1,2,4-triazole-3-carbonyl)azetidin-3-yl)-[1,2,4]triazolo[1,5-a]pyridin-2-yl)amino)pyridazine-3-carboxamide | $^1$H NMR (400 MHz, DMSO-$d_6$) 12.12 (s, 1H), 11.41 (s, 1H), 9.41 (s, 1H), 9.32 (s, 1H), 8.87 (s, 1H), 8.59 (s, 1H), 7.81 (d, J = 9.4 Hz, 1H), 7.71 (d, J = 8.8 Hz, 1H), 4.92-4.93 (m, 1H), 4.40-4.60 (m, 2H), 4.13-4.15 (m, 2H), 3.93 (s, 3H), 2.87 (s, 3H), 2.15-2.16 (m, 1H), 0.88-0.90 (m, 4H). MS (ESI) m/e $[M + H]^+$ = 517. |
| Example L6 | Compound 50 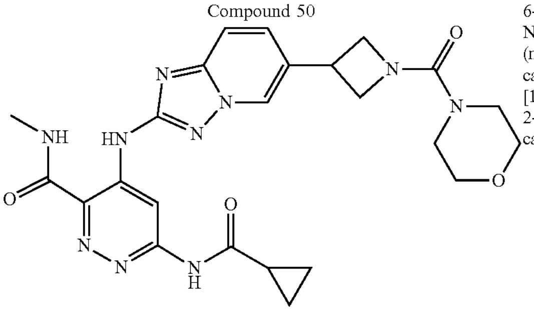 | 6-(cyclopropanecarboxamido)-N-methyl-4-((6-(1-(morpholine-4-carbonyl)azetidin-3-yl)-[1,2,4]triazolo[1,5-a]pyridin-2-yl)amino)pyridazine-3-carboxamide | $^1$H NMR (400 MHz, DMSO-$d_6$) 12.13 (s, 1H), 11.42 (s, 1H), 9.41 (s, 1H), 9.33 (d, J = 4.9 Hz, 1H), 8.81 (s, 1H), 7.72-7.75 (m, 2H), 4.30-4.32 (m, 2H), 3.98-4.00 (m, 3H), 3.53-3.58 (m, 4H), 3.26-3.29 (m, 4H), 2.87 (d, J = 4.7 Hz, 3H), 2.15-2.16 (m, 1H), 0.85-0.92 (m, 4H). MS (ESI) m/e $[M + H]^+$ = 521. |

Example M

Example M1: Synthesis of 6-(cyclopropanecarboxamido)-N-methyl-4-((6-(1-methylazetidin-3-yl)-[1,2,4]triazolo[1,5-a]pyridin-2-yl)amino)pyridazine-3-carboxamide (Compound 41)

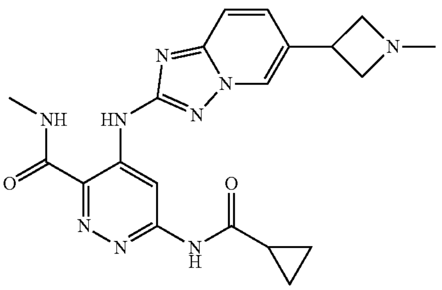 [SMILES: CNC(=O)c1nnc(NC(=O)C2CC2)cc1Nc1nc2ccc(C3CN(C)C3)cn2n1]

To a solution of 4-((6-(azetidin-3-yl)-[1,2,4]triazolo[1,5-a]pyridin-2-yl)amino)-6-(cyclopropanecarboxamido)-N-methylpyridazine-3-carboxamide (200 mg, 0.49 mmol) in MeOH (200 mL) were added formaldehyde in water (500 mg, 4.9 mmol) and $NaBH(OAc)_3$ (1.04 g, 4.9 mmol). The resulting mixture was stirred at room temperature for overnight. Upon completion of the reaction, the solvent was removed in vacuo and the residue was purified by reversed phase C18-column chromatography ($ACN/H_2O$=20-60%) to give the product (70 mg, 34%). $^1H$ NMR (400 MHz, DMSO-$d_6$) 12.15 (s, 1H), 11.43 (s, 1H), 9.40 (s, 1H), 9.34 (d, J=4.4 Hz, 1H), 8.88 (s, 1H), 7.83 (d, J=9.1 Hz, 1H), 7.73 (d, J=9.3 Hz, 1H), 4.02-4.05 (m, 3H), 3.80-3.81 (m, 2H), 2.87 (d, J=4.6 Hz, 3H), 2.64 (s, 3H), 2.16-2.17 (m, 1H), 0.89-0.91 (m, 4H). MS (ESI) m/e $[M+H]^+$=422.

Example N

Example N1: Synthesis of 4-((6-(azetidin-1-yl)-8-methoxy-[1,2,4]triazolo[1,5-a]pyridin-2-yl)amino)-6-(cyclopropanecarboxamido)-N-methylpyridazine-3-carboxamide (Compound 44)

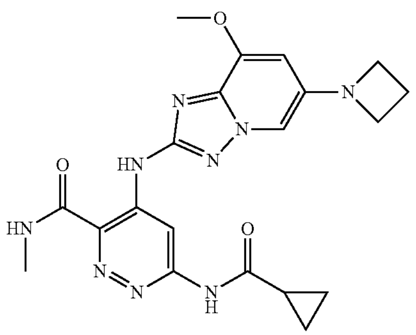 [SMILES: CNC(=O)c1nnc(NC(=O)C2CC2)cc1Nc1nc2c(OC)cc(N3CCC3)cn2n1]

Step 1: tert-butyl (5-bromo-3-methoxypyridin-2-yl)(tert-butoxycarbonyl)carbamate

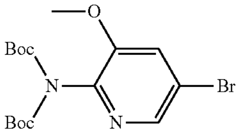 [SMILES: COc1cc(Br)cnc1N(C(=O)OC(C)(C)C)C(=O)OC(C)(C)C]

To a solution of 5-bromo-3-methoxypyridin-2-amine (3.57 g, 17.7 mmol), di-tert-butyl decarbonate (7.7 g, 35.4 mmol) and TEA (3575 mg, 35.4 mmol) in 30 mL of DMF was added DMAP (2116 mg, 17.7 mmol) and the resulting solution was stirred at rt for 48 h. Upon completion of the reaction, the solvent was removed in vacuo and the residue was purified by silica gel column chromatography (petroleum ether: EA=1:1) to give the product (5 g, 70%) as colorless oil. MS (ESI) m/e $[M+1]^+$=402.8.

Step 2: tert-butyl (5-(azetidin-1-yl)-3-methoxypyridin-2-yl)(tert-butoxycarbonyl)carbamate

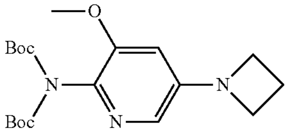 [SMILES: COc1cc(N2CCC2)cnc1N(C(=O)OC(C)(C)C)C(=O)OC(C)(C)C]

The desired compound was prepared from tert-butyl (5-bromo-3-methoxypyridin-2-yl)(tert-butoxycarbonyl)carbamate according to the procedure similar to that for compound 38 step 2 to give the product (500 mg, 52%) as a brown solid. MS (ESI) m/e $[M+1]^+$=379.9.

Step 3: 5-(azetidin-1-yl)-3-methoxypyridin-2-amine

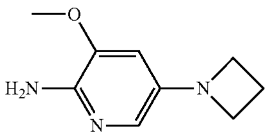

A solution of tert-butyl (5-(azetidin-1-yl)-3-methoxypyridin-2-yl)(tert-butoxycarbonyl)carbamate (500 mg, 1.32 mmol) in 6 mL of DCM/TFA (v:v=3:1) was stirred at room temperature for overnight. Upon completion of the reaction, the solvent was removed in vacuo to give the product 500 mg (crude) as brown oil. MS (ESI) m/e $[M+1]^+$=180.

Step 4: ethyl N-([5-(azetidin-1-yl)pyridin-2-yl]-2-methoxy-carbonothioyl)carbamate

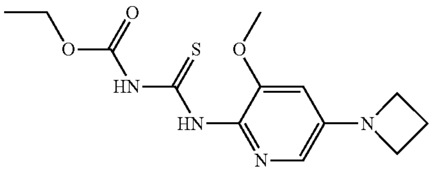 [SMILES: CCOC(=O)NC(=S)Nc1ncc(N2CCC2)cc1OC]

The desired compound was prepared from 5-(azetidin-1-yl)-3-methoxypyridin-2-amine according to the procedure similar to that for compound 2 step 1 to give the product (310 mg, 100%) as a brown solid. MS (ESI) m/e $[M+1]^+$ =310.9.

Step 5: 6-(azetidin-1-yl)-8-methoxy-[1,2,4]triazolo[1,5-a]pyridin-2-amine

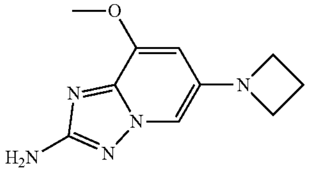 [SMILES: COc1cc(N2CCC2)cn2nc(N)nc12]

The desired compound was prepared from ethyl N-([5-(azetidin-1-yl)pyridin-2-yl]-2-methoxy-carbamothioyl)carbamate according to the procedure similar to that for compound 11 step 4 to give the product (75 mg, 91%) as a white solid.

Step 6: 4-((6-(azetidin-1-yl)-8-methoxy-[1,2,4]triazolo[1,5-a]pyridin-2-yl)amino)-6-chloro-N-methylpyridazine-3-carboxamide

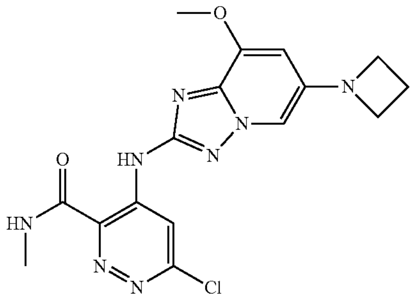 [SMILES: CNC(=O)c1nnc(Cl)cc1Nc1nc2c(OC)cc(N3CCC3)cn2n1]

The desired compound was prepared from 6-(azetidin-1-yl)-8-methoxy-[1,2,4]triazolo[1,5-a]pyridin-2-amine according to the procedure similar to that for compound 1 step 1 to give the product (75 mg, 60%) as a brown solid. MS (ESI) m/e $[M+1]^+$=388.9.

Step 7: 4-((6-(azetidin-1-yl)-8-methoxy-[1,2,4]triazolo[1,5-a]pyridin-2-yl)amino)-6-(cyclopropanecarboxamido)-N-methylpyridazine-3-carboxamide

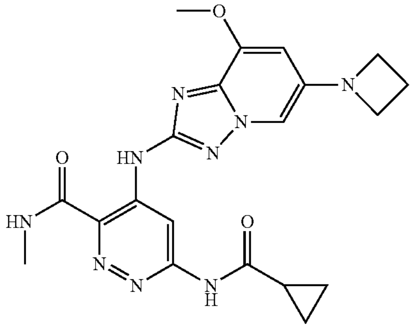 [SMILES: CNC(=O)c1nnc(NC(=O)C2CC2)cc1Nc1nc2c(OC)cc(N3CCC3)cn2n1]

The desired compound was prepared from 4-((6-(azetidin-1-yl)-8-methoxy-[1,2,4]triazolo[1,5-a]pyridin-2-yl)amino)-6-chloro-N-methylpyridazine-3-carboxamide according to the procedure similar to that for compound 1 step 2 to give the product (2 mg, 2.5%) as a white solid. $^1H$ NMR (400 MHz, DMSO-$d_6$) δ 11.95 (s, 1H), 11.36 (s, 1H), 9.34-9.15 (m, 2H), 7.45 (s, 1H), 6.51 (s, 1H), 3.99 (s, 3H), 3.86 (t, J=7.1 Hz, 4H), 2.86 (d, J=4.6 Hz, 3H), 2.35-2.30 (m, 2H), 2.14 (s, 1H), 0.88 (d, J=8.0 Hz, 4H). MS (ESI) m/e $[M+1]^+$=437.9.

Compounds 45 and 46 below were synthesized starting from the corresponding starting materials according to the similar procedures described as those of compound 11.

| Example | Compound | Name | $^1H$ NMR data LC/MS m/z (M + 1) |
|---|---|---|---|
| Example N2 | Compound 45 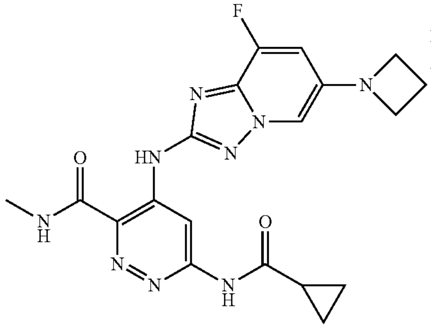 [SMILES: CNC(=O)c1nnc(NC(=O)C2CC2)cc1Nc1nc2c(F)cc(N3CCC3)cn2n1] | 4-((6-(azetidin-1-yl)-8-fluoro-[1,2,4]triazolo [1,5-a] pyridin-2-yl)amino)-6-(cyclopropanecarboxamido)-N-methylpyridazine-3-carboxamide | $^1H$ NMR (400 MHz, DMSO) δ 12.11 (d, J = 3.1 Hz, 1H), 11.40 (s, 1H), 9.32 (d, J = 3.1 Hz, 2H), 7.79 (s, 1H), 7.18 (d, J = 11.4 Hz, 1H), 3.87 (d, J = 3.0 Hz. 4H). 2.87 (s. 3H). 2.33 (s, 2H), 2.14 (s, 1H), 0.91 (s, 4H). MS (ESI) m/e $[M + 1]^+$ = 426. |

-continued

| Example | Compound | Name | $^1H$ NMR data LC/MS m/z (M + 1) |
| --- | --- | --- | --- |
| Example N3 | Compound 46 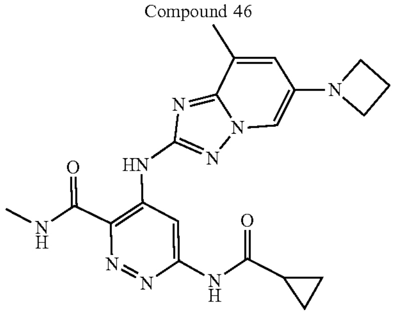 | 4-((6-(azetidin-1-yl)-8-methyl-[1,2,4]triazolo [1,5-alpyridin-2-yl)amino)-6-(cyclopropanecarboxamido)-N-methylpyridazine-3-carboxamide | $^1H$ NMR (400 MHz, DMSO-$d_6$) δ 11.95 (s, 1H), 11.35 (s, 1H), 9.42 (s, 1H), 9.29 (s, 1H), 7.69 (s, 1H), 6.94 (s, 1H), 3.84 (t, J = 6.5 Hz, 4H), 2.87 (d, J = 3.8 Hz, 3H), 2.33 (s, 3H), 2.14 (s, 1H), 1.23 (s, 2H), 0.88 (d, J = 8.1 Hz, 4H). MS (ESI) m/e $[M + 1]^+$ = 422. |

Example O

Example O1: Synthesis of 4-((6-(azetidine-1-carbonyl)-[1,2,4]triazolo[1,5-a]pyridin-2-yl)amino)-6-chloro-N-methylpyridazine-3-carboxamide (Compound 48)

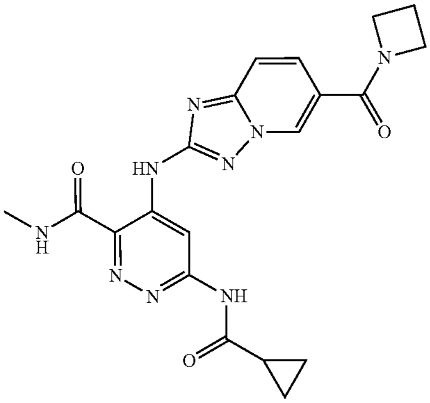 [SMILES: CNC(=O)c1nnc(NC(=O)C2CC2)cc1Nc1nc2ccc(C(=O)N3CCC3)cn2n1]

Step 1: 2-amino-[1,2,4]triazolo[1,5-a]pyridine-6-carboxylic acid

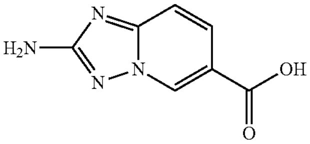 [SMILES: Nc1nc2ccc(C(=O)O)cn2n1]

To a solution of methyl 2-amino-[1,2,4]triazolo[1,5-a]pyridine-6-carboxylate (2 g, 10.4 mmol) in MeOH/THF (10 mL/10 mL) was added a solution of LiOH $H_2O$ (1.3 g, 31.3 mmol) in $H_2O$ (10 mL). The resulting mixture was stirred at rt for 12 h. Upon completion of the reaction, the organic solvent was removed in vacuo and the remained water solution was acidified with 1 N HCl to adjust the pH=3. The precipitated solid was collected by filtration and the filter cake was washed with water (5 mL), dried in air to give the product (700 mg, yield: 37.8%) as a light yellow solid. $^1H$ NMR (DMSO-$d_6$) δ 13.23 (s, 1H), 8.96 (s, 1H), 7.83 (dd, J=9.3 Hz, 1.4 Hz, 1H), 7.39 (d, J=9.1 Hz, 1H), 6.34 (s, 2H). MS (ESI) m/e $[M+1]^+$=179.3.

Step 2: (2-amino-[1,2,4]triazolo[1,5-a]pyridin-6-yl)(azetidin-1-yl)methanone

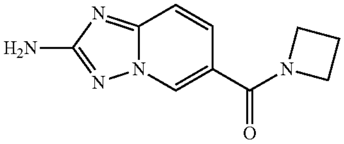 [SMILES: Nc1nc2ccc(C(=O)N3CCC3)cn2n1]

To a solution of 2-amino-[1,2,4]triazolo[1,5-a]pyridine-6-carboxylic acid (300 mg, 1.7 mmol) and TEA (511 mg, 5.1 mmol) in DCM (5 mL) and DMF (15 mL) was added HATU (768 mg, 2.0 mmol). The resulting mixture was stirred at rt for 30 min. Then azetidine hydrochloride (189 mg, 2.0 mmol) was added and the mixture was stirred at rt for another 12 h.

Upon completion of the reaction, the precipitated solid was collected by filtration and the filter cake was washed with DCM (10 mL), dried in air to give the product (220 mg, 60.1% yield) as an off-white solid. $^1H$ NMR (DMSO-$d_6$) δ 8.76 (s, 1H), 7.63 (d, J=9.1 Hz, 1H), 7.37 (d, J=9.0 Hz, 1H), 6.21 (s, 2H), 4.41 (s, 2H), 4.06 (s, 2H), 2.34-2.21 (m, 2H). MS (ESI) m/e $[M+1]^+$=218.3.

Step 3: 4-((6-(azetidine-1-carbonyl)-[1,2,4]triazolo[1,5-a]pyridin-2-yl)amino)-6-chloro-N-methylpyridazine-3-carboxamide

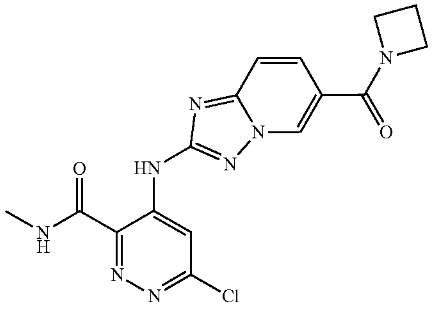 [SMILES: CNC(=O)c1nnc(Cl)cc1Nc1nc2ccc(C(=O)N3CCC3)cn2n1]

To a suspension of 4,6-dichloro-N-methylpyridazine-3-carboxamide (100 mg, 0.49 mmol) and (2-amino-[1,2,4]triazolo[1,5-a]pyridin-6-yl)(azetidin-1-yl)methanone (100 mg, 0.46 mmol) in THE (100 mL) was added NaHMDS (2 mL, 2 mmol, 1M in THF) in one portion at 70° C. and the mixture was stirred at this temperature for 5 min. After cooled to room temperature, the solvent was removed in vacuo and the residue was purified by combi-flash (MeOH/DCM=0-10%) to give the product (100 mg, 53% yield) as a brown solid. MS (ESI) m/e $[M+1]^+$=386.9.

Step 4: 4-((6-(azetidine-1-carbonyl)-[1,2,4]triazolo[1,5-a]pyridin-2-yl)amino)-6-(cyclopropanecarboxamido)-N-methylpyridazine-3-carboxamide (Compound 48)

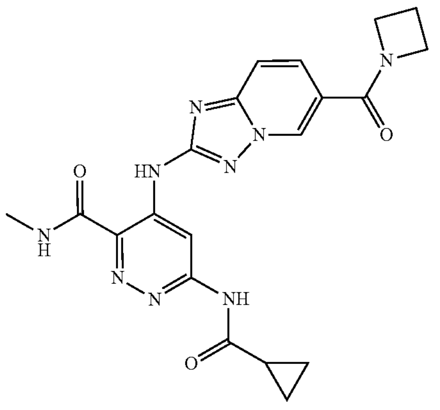 [SMILES: CNC(=O)c1nnc(NC(=O)C2CC2)cc1Nc1nc2ccc(C(=O)N3CCC3)cn2n1]

The desired compound was prepared from 4-((6-(azetidine-1-carbonyl)-[1,2,4]triazolo[1,5-a]pyridin-2-yl)amino)-6-chloro-N-methylpyridazine-3-carboxamide according to the procedure similar to that for compound 6 step 2 to give the product (3 mg, 5.3%). $^1H$ NMR (400 MHz, DMSO-$d_6$) δ 12.24 (s, 1H), 11.45 (s, 1H), 9.43 (s, 1H), 9.36 (m, 1H), 9.01 (s, 1H), 7.86 (d, J=9.3 Hz, 1H), 7.74 (d, J=9.3 Hz, 1H), 4.45 (s, 2H), 4.09 (s, 2H), 2.88 (d, J=4.8 Hz, 3H), 2.35-2.23 (m, 2H), 2.18-2.12 (m, 1H), 0.97-0.85 (m, 4H). MS (ESI) m/e $[M+1]^+$=435.9.

Example P

Example P1: Synthesis of 6-(cyclopropanecarboxamido)-N-methyl-4-((6-(4-(1-methylazetidin-3-yl)piperidin-1-yl)-[1,2,4]triazolo[1,5-a]pyridin-2-yl)amino)pyridazine-3-carboxamide (Compound 55)

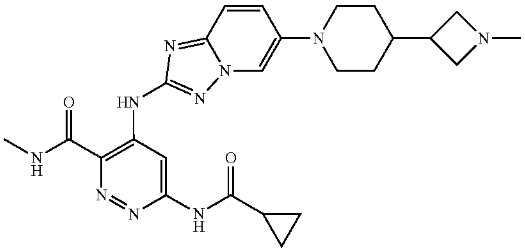

Step 1: tert-butyl 3-(pyridin-4-yl)azetidine-1-carboxylate

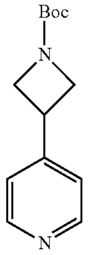

A mixture of pyridin-4-ylboronic acid (1 g, 8.13 mmol), tert-butyl 3-iodoazetidine-1-carboxylate (1.84 g, 6.50 mmol), $Pd(PPh_3)_4$ (469.7 mg, 406.50 umol) and $K_3PO_4$ (3.4 g, 16.20 mmol) in DMF (15 mL) and $H_2O$ (1 mL) was stirred at 60° C. for 12 h. After cooled to room temperature, $H_2O$ (50 mL) was added and the resulting solution was extracted with EA (30 mL×3). The combined organic layer was washed with brine, dried over with $Na_2SO_4$, filtered and concentrated. The residue was purified by silica gel column chromatography (petroleum ether:EA=20:1 to 1:1) to afford the product (240 mg, 12% yield) as brown oil. $^1H$ NMR ($CDCl_3$) δ 8.59 (d, J=5.04 Hz, 2H), 7.25 (d, J=6.00 Hz, 2H), 4.36 (t, J=8.69 Hz, 2H), 3.71 (t, J=8.61 Hz, 1H), 1.47 (s, 9H).

Step 2: tert-butyl 3-(piperidin-4-yl)azetidine-1-carboxylate

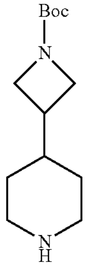 [SMILES: CC(C)(C)OC(=O)N1CC(C2CCNCC2)C1]

The mixture of tert-butyl 3-(pyridin-4-yl)azetidine-1-carboxylate (570 mg, 2.43 mmol) and PtO2 (300 mg) in AcOH (10 mL) and MeOH (10 mL) was stirred at rt for 12 h under H2 (30 Psi) atmosphere. Upon completion of the reaction, the catalyst was removed by filtration and the filtrate was concentrated in vacuo to give the product (500 mg, crude) as brown oil. It was used directly for next step without further purification.

Step 3: tert-butyl 3-(1-(6-nitropyridin-3-yl)piperidin-4-yl)azetidine-1-carboxylate

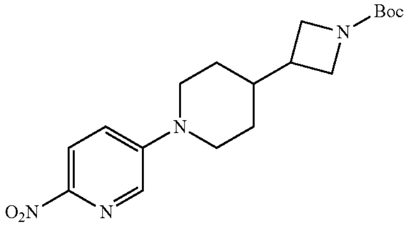 [SMILES: CC(C)(C)OC(=O)N1CC(C2CCN(c3ccc([N+](=O)[O-])nc3)CC2)C1]

The mixture of 5-fluoro-2-nitropyridine (300 mg, 2.08 mmol), tert-butyl 3-(piperidin-4-yl)azetidine-1-carboxylate (500 mg, 2.12 mmol) and DIEA (1.6 g, 12.48 mmol) in dioxane (30 mL) was stirred at 100° C. for 12 h. After cooled to room temperature, the solution was removed in vacuo and the residue was re-dissolved with $H_2O$ (30 mL). The resulting solution was extracted with EA (20 mL×3) and the combined organic layers was dried over $Na_2SO_4$ and concentrated. The residue was purified by silica gel column chromatography (petroleum ether:EA=1:1) to afford the product (410 mg, 1.13 mmol, 54% yield) as a yellow solid.

Step 4: tert-butyl 3-(1-(6-aminopyridin-3-yl)piperidin-4-yl)azetidine-1-carboxylate

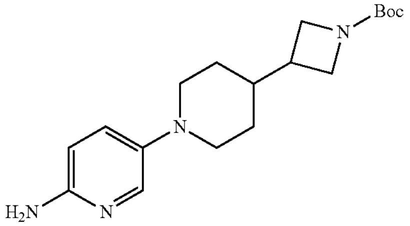

A mixture of tert-butyl 3-(1-(6-nitropyridin-3-yl)piperidin-4-yl)azetidine-1-carboxylate (410 mg, 1.13 mmol) and Pd/C (10%, 200 mg) in THE (10 mL) was stirred at rt for 3 h under H2 (15 Psi) atmosphere. Upon completion of the reaction, the catalyst was removed by filtration and the filtrate was concentrated in vacuo to give the product (450 mg, crude) as brown oil. It was used directly for next step without further purification.

Step 5: tert-butyl 3-(1-(6-(3-(ethoxycarbonyl)thioureido)pyridin-3-yl)piperidin-4-yl)azetidine-1-carboxylate

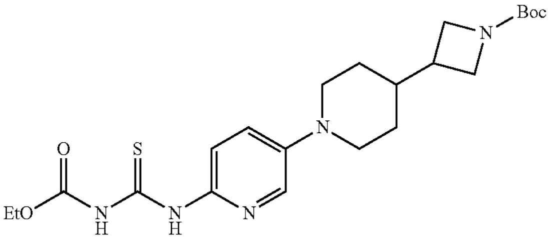 [SMILES: CCOC(=O)NC(=S)Nc1ccc(N2CCC(C3CN(C(=O)OC(C)(C)C)C3)CC2)cn1]

The desired compound was prepared from tert-butyl 3-(1-(6-aminopyridin-3-yl)piperidin-4-yl)azetidine-1-carboxylate according to the procedure similar to that for compound 11 step 3 to give the product (625 mg, crude) as brown oil. It was used directly for next step without further purification.

Step 6: tert-butyl 3-(1-(2-amino-[1,2,4]triazolo[1,5-a]pyridin-6-yl)piperidin-4-yl)azeti dine-1-carboxylate

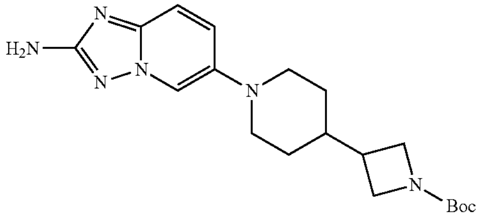 [SMILES: CC(C)(C)OC(=O)N1CC(C2CCN(c3ccc4nc(N)nn4c3)CC2)C1]

The desired compound was prepared from tert-butyl 3-(1-(6-(3-(ethoxycarbonyl)thioureido)pyridin-3-yl)piperidin-4-yl)azetidine-1-carboxylate according to the procedure similar to that for compound 11 step 4 to give the product (202 mg, 42% yield) as an off-white solid. $^1$H NMR (DMSO-$d_6$) δ 7.96 (d, J=1.75 Hz, 1H), 7.35 (dd, J=9.57, 2.06 Hz, 1H), 7.21 (d, J=9.51 Hz, 1H), 5.71 (s, 2H), 3.87 (brs, 2H), 3.59 (brs, 2H), 3.46-3.54 (m, 2H), 2.53-2.60 (m, 2H), 2.23-2.35 (m, 1H), 1.71 (d, J=12.13 Hz, 2H), 1.52 (d, J=9.76 Hz, 1H), 1.37 (s, 9H), 1.10-1.23 (m, 2H). MS (ESI) m/e $[M+1]^+$=373.3.

Step 7: tert-butyl 3-(1-(2-((6-chloro-3-(methylcarbamoyl)pyridazin-4-yl)amino)-[1,2,4]triazolo[1,5-a]pyridin-6-yl)piperidin-4-yl)azetidine-1-carboxylate

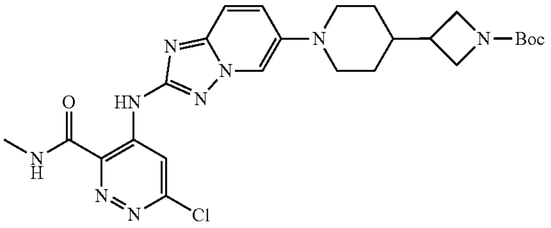 [SMILES: CNC(=O)c1nnc(Cl)cc1Nc1nc2ccc(N3CCC(C4CN(C(=O)OC(C)(C)C)C4)CC3)cn2n1]

The desired compound was prepared from tert-butyl 3-(1-(2-amino-[1,2,4]triazolo[1,5-a]pyridin-6-yl)piperidin-4-yl)azetidine-1-carboxylate according to the procedure similar to that for compound 26 step 1 to give the product (150 mg, 43%) as a brown solid. MS (ESI) m/e $[M+1]^+$=542.

Step 8: tert-butyl 3-(1-(2-((6-(cyclopropanecarboxamido)-3-(methylcarbamoyl)pyridazin-4-yl)amino)-[1,2,4]triazolo[1,5-a]pyridin-6-yl)piperidin-4-yl)azetidine-1-carboxylate

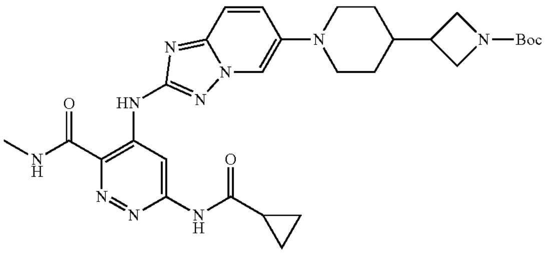 [SMILES: CNC(=O)c1nnc(NC(=O)C2CC2)cc1Nc1nc2ccc(N3CCC(C4CN(C(=O)OC(C)(C)C)C4)CC3)cn2n1]

The desired compound was prepared from tert-butyl 3-(1-(2-((6-chloro-3-(methylcarbamoyl)pyridazin-4-yl)amino)-[1,2,4]triazolo[1,5-a]pyridin-6-yl)piperidin-4-yl)azetidine-1-carboxylate according to the procedure similar to that for compound 1 step 2 to give the product (100 mg, 62%) as a yellow solid. MS (ESI) m/e $[M+1]^+$=590.9.

Step 9: 4-((6-(4-(azetidin-3-yl)piperidin-1-yl)-[1,2,4]triazolo[1,5-a]pyridin-2-yl)amino)-6-(cyclopropanecarboxamido)-N-methylpyridazine-3-carboxamide

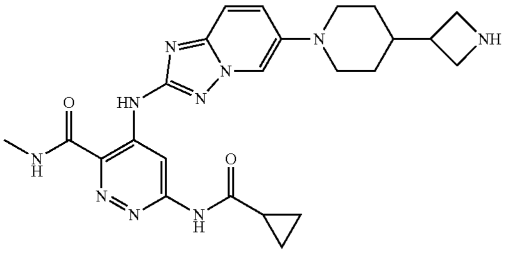 [SMILES: CNC(=O)c1nnc(NC(=O)C2CC2)cc1Nc1nc2ccc(N3CCC(C4CNC4)CC3)cn2n1]

A solution of tert-butyl 3-(1-(2-((6-(cyclopropanecarboxamido)-3-(methylcarbamoyl)pyridazin-4-yl)amino)-[1,2,4]triazolo[1,5-a]pyridin-6-yl)piperidin-4-yl)azetidine-1-carboxylate (100 mg, 0.17 mmol) in 2 mL of DCM/TFA (v:v=3:1) was stirred at room temperature for 2 h. Upon completion of the reaction, the solution was removed in vacuo and the residue was purified by Prep-TLC (MeOH/DCM=10%) to give the product (80 mg, 96%) as a brown solid. MS (ESI) m/e $[M+1]^+$=490.9.

Step 10: 6-(cyclopropanecarboxamido)-N-methyl-4-((6-(4-(1-methylazetidin-3-yl)piperidin-1-yl)-[1,2,4]triazolo[1,5-a]pyridin-2-yl)amino)pyridazine-3-carboxamide (Compound 55)

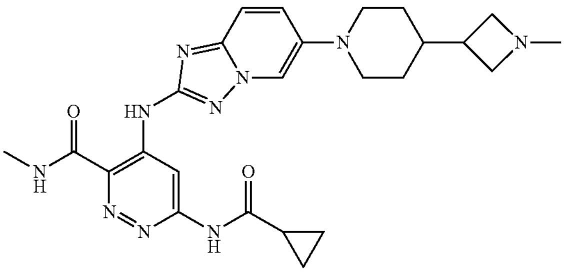

The desired compound was prepared from 4-((6-(4-(azetidin-3-yl)piperidin-1-yl)-[1,2,4]triazolo[1,5-a]pyridin-2-yl)amino)-6-(cyclopropanecarboxamido)-N-methylpyridazine-3-carboxamide according to the procedure similar to that for compound 41 to give the product (10 mg, 13%). $^1$H NMR (400 MHz, DMSO-$d_6$) δ 12.02 (s, 1H), 11.39 (s, 1H), 9.32 (d, J=17.9 Hz, 2H), 8.18 (s, 1H), 7.64 (d, J=9.6 Hz, 1H), 7.57 (d, J=9.5 Hz, 1H), 4.15 (s, 1H), 4.02 (s, 1H), 3.91 (s, 1H), 3.77 (d, J=7.6 Hz, 1H), 3.64 (d, J=10.9 Hz, 2H), 2.87 (d, J=4.3 Hz, 3H), 2.82 (d, J=4.9 Hz, 1H), 2.76 (d, J=4.8 Hz, 2H), 2.68-2.59 (m, 2H), 2.15 (s, 1H), 1.72 (dd, J=34.1, 12.1 Hz, 3H), 1.23 (s, 3H), 0.89 (d, J=8.1 Hz, 4H). MS (ESI) m/e $[M+1]^+$=505.1.

Example Q

Example Q1: Synthesis of 6-(cyclopropanecarboxamido)-N-methyl-4-((6-(3-(thiazolidine-3-carbonyl)azetidin-1-yl)-[1,2,4]triazolo[1,5-a]pyridin-2-yl)amino)pyridazine-3-carboxamide (Compound 56)

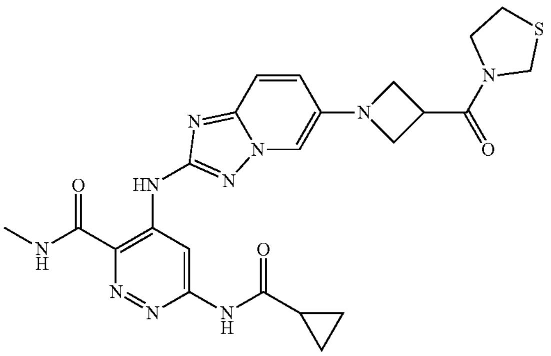 [SMILES: CNC(=O)c1nnc(NC(=O)C2CC2)cc1Nc1nc2ccc(N3CC(C(=O)N4CCSC4)C3)cn2n1]

Step 1: tert-butyl 3-(thiazolidine-3-carbonyl)azetidine-1-carboxylate

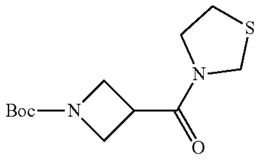 [SMILES: CC(C)(C)OC(=O)N1CC(C(=O)N2CCSC2)C1]

To a solution of 1-(tert-butoxycarbonyl)azetidine-3-carboxylic acid (1 g, 4.9 mmol) and thiazolidine (885 mg, 9.9 mmol) in DCM (30 mL) were added HOBt (795 mg, 5.9 mmol), EDCI (1.4 g, 7.4 mmol) and DIPEA (2.5 g, 19.6 mmol) at rt and the resulting mixture was stirred at this temperature for 12 h. Upon completion of the reaction, the solvent was removed in vacuo and the residue was re-dissolved with water (100 mL). The resulting solution was extracted with DCM (50 mL×3) and the combined organic layer was washed with brine (30 mL), dried over $Na_2SO_4$, filtered and concentrated in vacuo. The residue was purified by silica gel column chromatography (petroleum ether/EA=10:1) to give the product (1.2 g, 89%) as a yellow oil. MS (ESI) m/e $[M+1]^+$=273.1.

Step 2: azetidin-3-yl(thiazolidin-3-yl)methanone

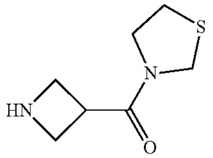 [SMILES: O=C(C1CNC1)N1CCSC1]

To a solution of tert-butyl 3-(thiazolidine-3-carbonyl)azetidine-1-carboxylate (1.2 g, 4.4 mmol) in DCM (10 mL) was added TFA (10 mL) and the reaction mixture was stirred at rt for 1 h. Upon completion of the reaction, aq. $Na_2CO_3$ was added to adjust pH value to 9-10 and then extracted with DCM (30 mL×3). The combined organic layer was washed with brine (10 mL), dried over $Na_2SO_4$, filtered and concentrated to give the product (0.75 g, crude) as a yellow solid. MS (ESI) m/e $[M+1]^+$=173.1.

Step 3: (1-(6-nitropyridin-3-yl)azetidin-3-yl)(thiazolidin-3-yl)methanone

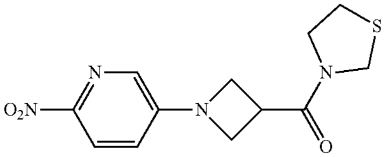

To a solution of azetidin-3-yl(thiazolidin-3-yl)methanone (750 mg, 4.36 mmol) in 1,4-dioxane (20 mL) were added DIPEA (1.69 g, 13.08 mmol) and 5-fluoro-2-nitropyridine (619 mg, 4.36 mmol) at rt and the resulting mixture was stirred at 100° C. for 12 h. After cooled to room temperature, the solvent was removed in vacuo and the residue was re-dissolved with water (50 mL). The resulting solution was extracted with EA (40 mL×3) and the combined organic layer was washed with brine (30 mL), dried over $Na_2SO_4$, filtered and concentrated. The residue was purified by silica gel column chromatography (petroleum ether/EA=10:1) to give the product (1 g, 78%) as a yellow solid.

Step 4: (1-(6-aminopyridin-3-yl)azetidin-3-yl)(thiazolidin-3-yl)methanone

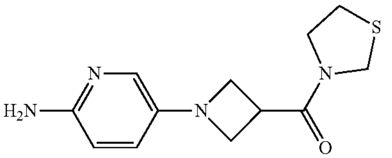 [SMILES: O=C(C1CN(c2ccc([N+](=O)[O-])nc2)C1)N1CCSC1]

To a solution of (1-(6-nitropyridin-3-yl)azetidin-3-yl)(thiazolidin-3-yl)methanone (1 g, 3.4 mmol) in THE (20 mL) was added Pd/C (10%, 100 mg) and the mixture was stirred at rt for 2 h under H2 (15 psi) atmosphere. Upon completion of the reaction, the catalyst was removed by filtration and the filtrate was concentrated in vacuo to give the product (800 mg, crude) as yellow oil, which was used for the next step without further purification. MS (ESI) m/e $[M+1]^+$=265.1.

Step 5: ethyl N-((5-[3-(1,3-thiazolidine-3-carbonyl)azetidin-1-yl]pyridin-2-yl)carbamothioyl)carbamate

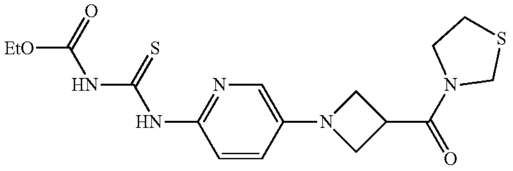 [SMILES: CCOC(=O)NC(=S)Nc1ccc(N2CC(C(=O)N3CCSC3)C2)cn1]

The desired compound was prepared from (1-(6-aminopyridin-3-yl)azetidin-3-yl)(thiazolidin-3-yl)methanone according to the procedure similar to that for compound 11 step 3 to give the product (1 g, crude) as yellow oil, which was used for the next step without further purification.

Step 6: (1-(2-amino-[1,2,4]triazolo[1,5-a]pyridin-6-yl)azetidin-3-yl)(thiazolidin-3-yl)methanone

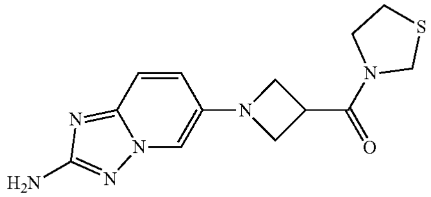 [SMILES: Nc1nc2ccc(N3CC(C(=O)N4CCSC4)C3)cn2n1]

The desired compound was prepared from ethyl N-((5-[3-(1,3-thiazolidine-3-carbonyl)azetidin-1-yl]pyridin-2-yl)carbamothioyl)carbamate according to the procedure similar to that for compound 11 step 4 to give the product (416 mg, 54%) as a yellow solid. $^1H$ NMR (DMSO-$d_6$) δ: 7.75 (s, 1H), 7.23 (d, J=9.3 Hz, 1H), 6.88 (d, J=9.1 Hz, 1H), 5.69 (s, 2H), 4.47 (s, 2H), 3.97-4.07 (m, 2H), 3.76-3.91 (m, 3H), 3.65 (d, J=12.6 Hz, 2H), 3.08 (t, J=6.2 Hz, 1H), 3.00 (t, J=6.3 Hz, 1H). MS (ESI) m/e $[M+1]^+$=305.1.

Step 7: 6-chloro-N-methyl-4-((6-(3-(thiazolidine-3-carbonyl)azetidin-1-yl)-[1,2,4]triazolo[1,5-a]pyridin-2-yl)amino)pyridazine-3-carboxamide

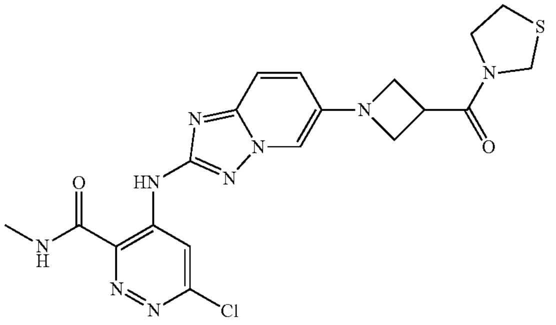 [SMILES: CNC(=O)c1nnc(Cl)cc1Nc1nc2ccc(N3CC(C(=O)N4CCSC4)C3)cn2n1]

The desired compound was prepared from (1-(2-amino-[1,2,4]triazolo[1,5-a]pyridin-6-yl)azetidin-3-yl)(thiazolidin-3-yl)methanone according to the procedure similar to that for compound 26 step 1 to give the product (50 mg, 13%) as a brown solid. MS (ESI) m/e $[M+1]^+$=474.

Step 8: 6-(cyclopropanecarboxamido)-N-methyl-4-((6-(3-(thiazolidine-3-carbonyl)azetidin-1-yl)-[1,2,4]triazolo[1,5-a]pyridin-2-yl)amino)pyridazine-3-carboxamide (Compound 56)

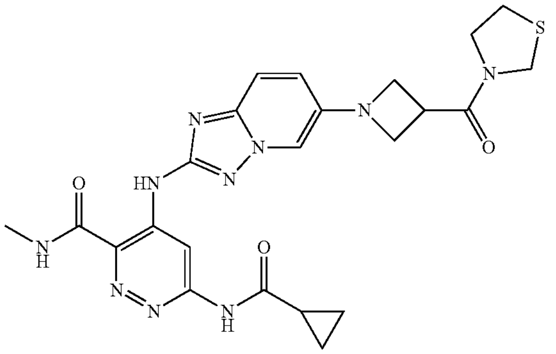 [SMILES: CNC(=O)c1nnc(NC(=O)C2CC2)cc1Nc1nc2ccc(N3CC(C(=O)N4CCSC4)C3)cn2n1]

The desired compound was prepared from 6-chloro-N-methyl-4-((6-(3-(thiazolidine-3-carbonyl)azetidin-1-yl)-[1,2,4]triazolo[1,5-a]pyridin-2-yl)amino)pyridazine-3-carboxamide according to the procedure similar to that for compound 1 step 2 to give the product (5 mg, 11%). $^1$H NMR (400 MHz, DMSO-$d_6$) δ 12.01 (s, 1H), 11.37 (s, 1H), 9.32 (d, J=23.3 Hz, 2H), 7.96 (s, 1H), 7.58 (d, J=9.7 Hz, 1H), 7.15 (s, 1H), 4.49 (s, 2H), 4.11 (s, 2H), 3.96 (s, 2H), 3.65 (s, 2H), 3.10 (s, 1H), 3.01 (s, 2H), 2.87 (d, J=4.5 Hz, 3H), 2.14 (s, 1H), 0.89 (d, J=8.2 Hz, 4H). MS (ESI) m/e $[M+1]^+$=522.9.

Assay A: TYK2-JH2 Biochemical Assay

Compounds disclosed herein were tested for blocking of TYK2-JH2 (aa 575-869, in-house) protein with its probe in an assay based on Homogeneous Time Resolved Fluorescence.

Compound dilution is done according to the following protocol: (1) Prepare 500× compounds solution in DMSO from 500 uM by 5-fold dilution, total 10 doses were included; (2) Prepare 10× compounds solution in an assay buffer containing 20 mM HEPES, pH 7.5, 10 mM MgCl2, 0.005% BSA, 2 mM DTT, 0.015% Brij-35 by transferring 1 μl serial 500× stock solution into 49 μl assay buffer. 4 μl of 0.2 nM recombinant TYK2-JH2 protein was pre-incubated with 1 μl of 10×serial dilution of compounds at room temperature for 0.5 hour. Then 5 μl of 10 nM in-house Probe 1 (6-((3,5-dimethylphenyl)amino)-8-((4,26-dioxo-30-((3aS,4S,6aR)-2-oxohexahydro-1H-thieno[3,4-d]imidazol-4-yl)-7,10,13,16,19,22-hexaoxa-3,25-diazatriacontyl)amino)imidazo[1,2-b]pyridazine-3-carboxamide, KD=10 nM), 5 μl Mab Anti-6His Tb cryptate Gold (Cat: 61HI2TLB, Cisbio Bioassays) and Streptavidin-XL665(Cat: 610SAXLB, Cisobio Bioassays) mixture were added to plate and further incubated at room temperature for 1 hour. The HTRF signals (ex337 nm, em620 nm/665 nm) were read on BMG PHERAstar FS instrument. The inhibition percentage of TYK2 interaction with its probe in presence of increasing concentrations of compounds was calculated based on the ratio of fluorescence at 615 nm to that at 665 nm. The IC50 for each compound was derived from fitting the data to the four-parameter logistic equation by Dotmatics.

Assay B: JAK1-JH2 Biochemical Assay

Compounds disclosed herein were tested for blocking of JAK1-JH2 protein (aa 561-860, in-house) with its probe in an assay based on Homogeneous Time Resolved Fluorescence. Compound dilution is done according to the following protocol: (1) Prepare 500× compounds solution in DMSO from 500 uM by 5-fold dilution, total 10 doses were included; (2) Prepare 10× compounds solution in an assay buffer containing 20 mM HEPES, pH 7.5, 10 mM MgCl2, 0.005% BSA, 2 mM DTT, 0.015% Brij-35 by transferring 1 μl serial 500× stock solution into 49 μl assay buffer. 4 μL of 1.17 nM recombinant JAK1-JH2 protein was pre-incubated with 1 μl of 10×serial dilution of compounds at room temperature for 0.5 hour. Then 5 μL of 2.9 nM in-house Probe 2 (N-(2-(4-(2-(methyl(4-((((Z)-2-oxoindolin-3-ylidene)(phenyl)methyl)amino)phenyl)amino)-2-oxoethyl)piperazin-1-yl)ethyl)-1-(5-((3aS,4S,6aR)-2-oxohexahydro-1H-thieno[3,4-d]imidazol-4-yl)pentanamido)-3,6,9,12,15,18-hexaoxahenicosan-21-amide, KD=2.9 nM), 5 μl Mab Anti-6His Tb cryptate Gold (Cat: 61HI2TLB, Cisbio Bioassays) and Streptavidin-XL665(Cat: 610SAXLB, Cisobio Bioassays) mixture were added to plate and further incubated at room temperature for 1 hour. The HTRF signals (ex337 nm, em620 nm/665 nm) were read on BMG PHERAstar FS instrument. The inhibition percentage of JAK1 interaction with its probe in presence of increasing concentrations of compounds was calculated based on the ratio of fluorescence at 615 nm to that at 665 nm. The IC50 for each compound was derived from fitting the data to the four-parameter logistic equation by Dotmatics.

Assay C: IL-12-JAK2, TYK2/p-STAT4 (Tyr693) Inhibition IC50 Cellular Assay

To evaluate the inhibition effect of compounds disclosed herein on JAK2, TYK2/p-STAT4 (Tyr693) activated by IL-12 in NK-92 cell line, NK-92 cells were collected and washed 3 times by DPBS and resuspended in MEM-α (GIBCO,Cat #12561056) with 10% FBS (Gibco, Cat #10099, Lot #1891605), without IL-2 (R&D systems,Cat #202-IL), starved overnight. Cells were collected and resuspended in 1640 medium (phenol red free, Gibco, Cat #11835-030) with 0.1% BSA, and 12.5 μl/5×$10^4$/well cell suspension were seeded to the 96-well plate (Corning, Cat

#3799). Then cells were treated with compounds diluted in 0.2% DMSO 1640 medium, at 37° C., 1 h. Dilution is done according to the following protocol: (1) make 500× compounds solution in DMSO from 5 mM by 4-fold dilution, total 8 doses were included; (3) make 2× compounds solution in assay medium by transferring 0.5 μl serial 500× stock solution into 125 μl assay medium; (4) 15 μl of 2× serial solution is added to cells and incubate at 37° C. for 1 h, the final compound conc. is 10000,2500,625,156.25,39,9.8,2.4 and 0.61 nM, respectively. After 1 h, cells were treated with 2.5 μl medium containing IL-12 at 37° C. (R&D systems, Cat #219-IL-005, final conc.40 ng/ml), 30 min. Following cells were lysed with 7.5 μl lysis buffer at RT, shaking on shaker for 1 h. 10 μL of cell lysate were transferred to a PE 384-well Proxiplate detection plate, and 5 μL of pre-mixed Alphascreen beads were added to each well. Covered the plate with a plate sealer, span 1000 rpm for 1 min, mix, Incubated overnight at room temperature. Read on BMG PheraStar with Alphascreen protocol. IC 50 values were calculated by fitting dependent data to the four-parameter logistic model using dotmatics software. The assay was performed by using AlphaLISA SureFire Ultra p-STAT4 (Tyr693) Assay Kit—High Volume (PE, Cat #ALSU-PST4-A-HV).

Assay D: IL-6-JAK1/p-STAT3(Tyr705) Inhibition IC50 Cellular Assay

To evaluate the inhibition effect of compounds disclosed herein on JAK1/p-STAT3(Tyr705) activated by IL-6 in TF-1 cell line, TF-1 cells were collected and washed 3 times by DPBS and resuspended in RPMI-1640 (phenol red free, Gibco, Cat #11835-030) with 0.1% FBS (Gibco, Cat #10099, Lot #1891605), without GM-CSF(R&D systems, Cat #215-GM-050), starved overnight. Cells were collected and resuspended in 1640 medium (phenol red free, Gibco, Cat #11835-030) with 0.1% BSA, and 12.5 μl/10×10$^4$/well cell suspension were seeded to the 96-well plate (Corning, Cat #3799). Then cells were treated with compounds diluted in 0.2% DMSO 1640 medium, at 37° C., 1 h. Dilution is done according to the following protocol: (1) make 500× compounds solution in DMSO from 5 mM by 4-fold dilution, total 8 doses were included; (3) make 2× compounds solution in assay medium by transferring 0.5 μl serial 500× stock solution into 125 μl assay medium; (4) 15 μl of 2× solution is added to cells and incubate at 37° C. for 1 h, the final compound conc. is 10000,2500,625,156.25,39,9.8,2.4 and 0.61 nM, respectively. After 1 h, cells were treated with 2.5 μl medium containing IL-6 at 37° C. (R&D systems, Cat #206-IL-010, final conc.50 ng/ml), 30 min. Following cells were lysed with 10 μl lysis buffer at RT, shaking on shaker for 1 h. 16 μL of cell lysate were transferred to a PE 384-well HTRF detection plate, and 4 μL of pre-mixed HTRF antibodies were added to each well. Covered the plate with a plate sealer, span 1000 rpm for 1 min, mix, Incubated overnight at room temperature. Read on BMG PheraStar with HTRF protocol (337 nm-665 nm-620 nm). IC 50 values were calculated by fitting dependent data to the four-parameter logistic model using dotmatics software. The assay was performed by using HTRF Phospho-STAT3(Tyr705) Cellular Assay Kit (Cisbio, Cat #62AT3PEG).

Compounds disclosed herein showed picomolar to nanomolar bio-chemical activity in TYK2-JH2 binding assay and also showed nanomolar activity in cellular assay. In the meanwhile, these compounds showed excellent selectivity in TYK2 bio-chemical/cellular assay against JAK1. See Table 1.

TABLE 1

| | | Biochemical assay | | | Cellular assay | | |
|---|---|---|---|---|---|---|---|
| Example | Compound | TYK2-JH2 IC50 (nM) | JAK1-JH2 IC50 (nM) | Selectivity fold (TYK2/ JAK1) | pSTAT4/IL-12 IC50 (nM) | pSTAT3/ IL-6 IC50 (nM) | Selectivity fold (TYK2/ JAK1) |
| Example A1 | Compound 1 | 456 | >10000 | >22 | ND | ND | ND |
| Example A2 | Compound 2 | 34 | 174 | 5 | ND | ND | ND |
| Example A3 | Compound 3 | 1.4 | 3.7 | 2.6 | ND | ND | ND |
| Example A4 | Compound 4 | 0.16 | 1.3 | 8 | 104 | 2410 | 23 |
| Example A5 | Compound 5 | 0.56 | 13 | 23 | >10000 | >10000 | 1 |
| Example B1 | Compound 6 | 0.936 | 2.03 | 2 | 3530 | >10000 | >3 |
| Example C1 | Compound 7 | 0.1 | 1.3 | 13 | ND | ND | ND |
| Example C2 | Compound 8 | 0.14 | 1.2 | 9 | ND | ND | ND |
| Example C3 | Compound 9 | 0.08 | 1.2 | 15 | 68.8 | >10000 | >145 |
| Example C4 | Compound 10 | 0.08 | 1.2 | 15 | 309 | >10000 | >32 |
| Example C5 | Compound 51 | 0.143 | 1.56 | 11 | 1320 | >10000 | >8 |
| Example D1 | Compound 52 | 0.099 | 1.21 | 12 | 68.4 | >10000 | >146 |
| Example E1 | Compound 11 | 0.047 | 1.6 | 34 | 13.3 | 6330 | 475 |
| Example E2 | Compound 12 | 0.047 | 1.2 | 26 | 9.01 | 9800 | 1087 |
| Example E3 | Compound 13 | 0.038 | 1.3 | 34 | 8.9 | 4060 | 453 |

TABLE 1-continued

| Example | Compound | Biochemical assay TYK2-JH2 IC50 (nM) | JAK1-JH2 IC50 (nM) | Selectivity fold (TYK2/JAK1) | Cellular assay pSTAT4/IL-12 IC50 (nM) | pSTAT3/IL-6 IC50 (nM) | Selectivity fold (TYK2/JAK1) |
|---|---|---|---|---|---|---|---|
| Example E4 | Compound 14 | 0.044 | 1.5 | 34 | 10 | 5400 | 540 |
| Example E5 | Compound 15 | 0.064 | 1.7 | 26 | 16 | 7270 | 454 |
| Example E6 | Compound 16 | 0.056 | 0.56 | 10 | 15.4 | 1640 | 106 |
| Example E7 | Compound 17 | 0.084 | 0.78 | 9 | 47.8 | >10000 | >209 |
| Example E8 | Compound 19 | 0.044 | 3.0 | 68 | 13.8 | >10000 | >724 |
| Example E9 | Compound 20 | 0.097 | 2.4 | 25 | 19.6 | >10000 | >510 |
| Example E10 | Compound 21 | 0.15 | 3.0 | 20 | 47 | >10000 | >212 |
| Example E11 | Compound 22 | 0.18 | 5.8 | 32 | ND | ND | ND |
| Example E12 | Compound 23 | 0.024 | 1.7 | 71 | 6.31 | 9930 | 1478 |
| Example E13 | Compound 24 | 0.047 | 2.6 | 55 | 15.9 | >10000 | >629 |
| Example E14 | Compound 25 | 0.11 | 1.8 | 16 | 42.6 | >10000 | >234 |
| Example E15 | Compound 29 | 0.045 | 1.3 | 29 | 8.14 | >10000 | >1228 |
| Example E16 | Compound 30 | 0.046 | 0.93 | 20 | 15.6 | 2910 | 186 |
| Example E17 | Compound 31 | 0.071 | 2.5 | 35 | 8.28 | 2630 | 317 |
| Example E18 | Compound 33 | 0.12 | 1.5 | 13 | 645 | >10000 | >15.5 |
| Example E19 | Compound 34 | 0.14 | 8.4 | 60 | 105 | >10000 | >95 |
| Example E20 | Compound 35 | 0.089 | 3.2 | 36 | 16.4 | >10000 | >609 |
| Example E21 | Compound 53 | 0.077 | 2.78 | 36 | 42 | >10000 | >238 |
| Example E22 | Compound 54 | 0.093 | 1.03 | 11 | 37.2 | 5120 | 138 |
| Example F1 | Compound 16 | 0.12 | 2.6 | 22 | 95 | >10000 | >105 |
| Example G1 | Compound 26 | 0.076 | 1.8 | 24 | 9.05 | >10000 | >1104 |
| Example H1 | Compound 27 | 0.057 | 1.2 | 21 | 34.2 | >10000 | >292 |
| Example J1 | Compound 32 | 0.086 | 1.8 | 21 | 15.6 | >10000 | >641 |
| Example J2 | Compound 36 | 0.053 | 1.3 | 25 | 14.9 | 4360 | 292 |
| Example K1 | Compound 38 | 0.50 | 3.8 | 8 | 219 | >10000 | >46 |
| Example L1 | Compound 39 | 0.093 | 3.7 | 40 | 50.9 | >10000 | >196 |
| Example L2 | Compound 42 | 0.081 | 2.6 | 32 | 276 | >10000 | >36 |
| Example L3 | Compound 43 | 0.072 | 1.5 | 21 | 127 | >10000 | >79 |
| Example L4 | Compound 48 | | | | | | |
| Example L5 | Compound 49 | 0.076 | 1.7 | 22 | 2000 | >10000 | >5 |
| Example L6 | Compound 50 | 0.04 | 1.5 | 38 | 86 | >10000 | >117 |
| Example M1 | Compound 41 | 0.26 | 2.6 | 10 | 63 | >10000 | >158 |
| Example N1 | Compound 44 | 0.87 | 1.4 | 2 | 687 | >10000 | >14 |
| Example N2 | Compound 45 | 0.063 | 1.28 | 20 | 14 | 9640 | 688 |
| Example N3 | Compound 46 | 0.089 | 1.47 | 17 | 21 | 4100 | 192 |
| Example O1 | Compound 48 | 0.17 | 1.06 | 6 | 169 | 4880 | 28 |

TABLE 1-continued

| | | Biochemical assay | | | Cellular assay | | |
|---|---|---|---|---|---|---|---|
| Example | Compound | TYK2-JH2 IC50 (nM) | JAK1-JH2 IC50 (nM) | Selectivity fold (TYK2/ JAK1) | pSTAT4/IL-12 IC50 (nM) | pSTAT3/ IL-6 IC50 (nM) | Selectivity fold (TYK2/ JAK1) |
| Example P1 | Compound 55 | 0.039 | 1.4 | 36 | 29 | >10000 | >344 |
| Example Q1 | Compound 56 | 0.16 | 2.18 | 14 | 157 | >10000 | >64 |

It is to be understood that, if any prior art publication is referred to herein, such reference does not constitute an admission that the publication forms a part of the common general knowledge in the art in any country.

In the claims which follow and in the preceding description of the invention, except where the context requires otherwise due to express language or necessary implication, the word "comprise" or variations such as "comprises" or "comprising" is used in an inclusive sense, i.e., to specify the presence of the stated features but not to preclude the presence or addition of further features in various embodiments of the invention.

The disclosures of all publications, patents, patent applications and published patent applications referred to herein by an identifying citation are hereby incorporated herein by reference in their entirety.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

What is claimed is:

1. A compound of Formula (I):

(I)

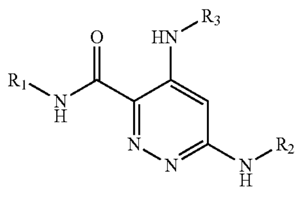

or a stereoisomer or pharmaceutically acceptable salt hereof wherein:

$R^1$ is hydrogen, $C_{1-6}$alkyl or $C_{3-6}$cycloalkyl, wherein said $C_{1-6}$alkyl and $C_{3-6}$cycloalkyl are each optionally substituted with 0-7 $R^{1a}$;

$R^{1a}$ at each occurrence is independently hydrogen, deuterium, halogen, —CN or —OMe;

$R^2$ is —C(O)$R^{2a}$ or a 4-10 membered heterocyclyl containing 1-2 heteroatoms selected from nitrogen, oxygen or sulfur, wherein said 4-10 membered heterocyclyl is optionally substituted with 0-4 $R^{2b}$;

$R^{2a}$ is independently $C_{1-6}$alkyl or $C_{3-6}$cycloalkyl;

$R^{2b}$ at each occurrence is independently hydrogen, =O, halo, —CN, —$(CH_2)_r$—$C_{3-6}$cycloalkyl, or a —$(CH_2)_r$-3-10 membered heterocyclyl comprising carbon atoms and 1-4 heteroatoms selected from nitrogen, oxygen or sulfur, wherein said —$(CH_2)_r$—$C_{3-6}$cycloalkyl and —$(CH_2)_r$-3-10 membered heterocyclyl are each optionally substituted with 0-2 $R^{2c}$;

$R^{2c}$ at each occurrence is independently hydrogen, -halo$C_{1-3}$alkyl or —$C_{1-3}$alkyl;

$R^3$ is

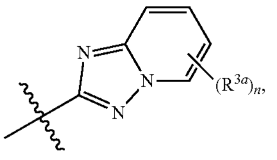

wherein n is an integer selected from 0, 1, 2, 3 and 4; and $R^{3a}$ at each occurrence is independently hydrogen, halogen, —CN, —$C_{1-6}$alkyl, —$C_{1-6}$alkoxyl, —P(O)$R^{3d}R^{3e}$, -$(L^1)_r$-CyA; or CyA, wherein said —$C_{1-6}$alkyl, and —$C_{1-6}$alkoxyl are each optionally substituted with 0-3 $R^{3d}$;

$L^1$ at each occurrence is independently —O—, —S—, —C(O)—, —NH—, —$CH_2$— or —NHC(O)—;

CyA is $C_{3-10}$ cycloalkyl, 3-10 membered heterocyclyl comprising carbon atoms and 1-4 heteroatoms selected from nitrogen, oxygen or sulfur, 6-10 membered aryl, or 4-10 membered heteroaryl comprising carbon atoms and 1-4 heteroatoms selected from nitrogen, oxygen or sulfur, wherein said $C_{3-10}$ cycloalkyl, 3-10 membered heterocyclyl, 6-10 membered aryl and 4-10 membered heteroaryl are each substituted with 0-3 $R^{3b}$;

$R^{3b}$ at each occurrence is independently hydrogen, halogen, —$C_{1-6}$alkyl, -oxo-, —O$R^{3c}$, —C(O)$R^{3d}$, —$S(O)_2R^{3d}$, —N$R^{3d}R^{3e}$, $C_{3-10}$cycloalkyl, a 3-10 membered heterocyclyl containing 1-4 heteroatoms selected from nitrogen, oxygen or sulfur, a 6-10 membered aryl, or a 4-10 membered heteroaryl comprising carbon atoms and 1-4 heteroatoms selected from nitrogen, oxygen or sulfur; wherein said-$C_{1-6}$alkyl, $C_{3-10}$ cycloalkyl, 3-10 membered heterocyclyl, 6-10 membered aryl and 4-10 membered heteroaryl are each optionally substituted with 0-3 —$R^{3d}$;

$R^{3c}$ and $R^{3d}$ at each occurrence are independently hydrogen, halogen, —CN, hydroxyl, —$C_{1-6}$alkyl, —$C_{1-6}$alkoxy, a 5-6 membered aryl, a 3-6 membered heterocyclyl containing 1-2 heteroatoms selected from nitrogen, oxygen or sulfur, or a 5-6 membered heteroaryl comprising carbon atoms and 1-3 heteroatoms selected from nitrogen, oxygen or sulfur, wherein said —$C_{1-6}$alkyl, —$C_{1-6}$alkoxy, 5-6 membered aryl, 3-6 membered heterocyclyl, 5-6 membered heteroaryl are optionally substituted by -halogen, —CN, hydroxyl, —$C_{1-6}$alkyl, —$C_{1-6}$alkoxyl, $C_{1-6}$alkylamino, di$C_{1-6}$alkylamino, a 3-6 membered heterocyclyl, a 6-10 membered aryl or a 5-10 membered heteroaryl;

$R^{3e}$ at each occurrence is independently selected from —H, —$C_{1-6}$alkyl, —$S(O)_2R^{3f}$ or —$C(O)R^{3f}$, wherein $R^{3f}$ is independently $C_{1-6}$alkyl or $C_{3-6}$cycloalkyl; and r is an integer of 0, 1 or 2.

2. A compound according to claim 1, wherein:

a) $R^2$ is oxetanyl, thiazolyl, pyridyl, pyrimidinyl, pyridazinyl, pyrazinyl or quinolinyl, each of which is substituted with 0-3 $R^{2b}$; or b) $R^2$ is —$C(O)R^{2a}$; or c) $R^2$ is

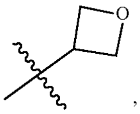, 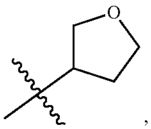, 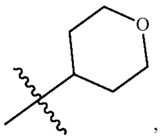, 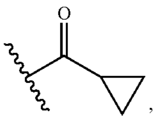, 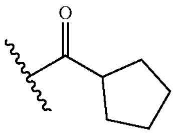 or 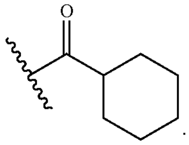.

3. A compound according to claim 1, wherein $R^1$ is methyl, ethyl, propyl, isopropyl, isobutyl, cyclopropyl, cyclobutyl, cyclopentyl and cyclohexanyl, each of which is optionally substituted with 0-3 $R^{1a}$.

4. A compound according to claim 3, wherein $R^1$ is methyl, or —$CD_3$.

5. A compound according to claim 1, wherein $R^3$ is

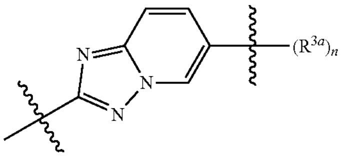

and n is 1.

6. A compound according to claim 5, wherein $R^{3a}$ is hydrogen, halogen, —CN, —$C_{1-6}$alkyl, —$P(O)R^{3d}R^{3e}$, -$(L^1)_{0-2}$-CyA or CyA, wherein CyA is a 3-6 membered heterocyclyl or 4-10 membered heteroaryl comprising carbon atoms and 1-4 heteroatoms selected from nitrogen, oxygen or sulfur and optionally substituted with 0-3 $R^{3b}$.

7. A compound according to claim 5, wherein $R^{3a}$ is 3-6 membered heterocyclyl or 4-10 membered heteroaryl comprising carbon atoms and 1-4 heteroatoms selected from nitrogen, oxygen or sulfur.

8. A compound according to claim 5, wherein:

a) CyA is a 5-6 membered heterocyclyl comprising carbon atoms and 1-4 heteroatoms selected from nitrogen or oxygen, or b) CyA is azetidinyl, piperidinyl and piperazinyl, each of which is substituted with 0-3 $R^{3b}$; or c) CyA is a 7-10 membered bridged heterocyclyl comprising carbon atoms and 1-2 heteroatoms selected from N and O substituted with 0-3 $R^{3b}$.

9. A compound according to claim 5, wherein CyA is

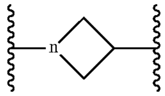, 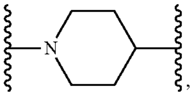, 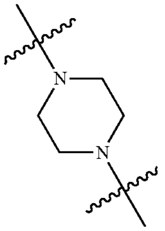, 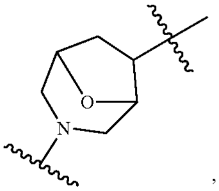, 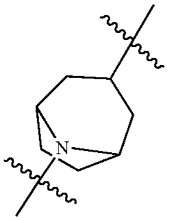 or 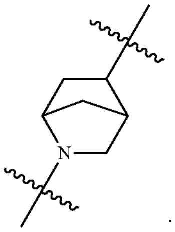.

10. A compound according to claim 9, wherein the N heteroatom on CyA is attached to $R^3$.

11. A compound according to claim 1, wherein $R^{3b}$ is hydrogen, halogen, —$C_{1-3}$alkyl, —$OR^{3c}$, —$C(O)R^{3d}$, $NR^{3d}R^{3e}$ or $C_{3-10}$cycloalkyl, wherein said —$C_{1-3}$alkyl and $C_{3-10}$cycloalkyl are optionally substituted with 0-3 —$R^{3d}$.

12. A compound according to claim 1, wherein $R^{3c}$ and $R^{3d}$ at each occurrence is independently selected from hydrogen, halogen, —CN, hydroxyl, —$C_{1-3}$alkyl, —$C_{1-3}$alkoxy, phenyl, a 3-6 membered heterocyclyl containing 1-2 heteroatoms selected from nitrogen, oxygen or sulfur, a 5-6 membered heteroaryl comprising carbon atoms and 1-3 heteroatoms selected from nitrogen, oxygen or sulfur, wherein said $C_{1-3}$alkyl, —$C_{1-3}$alkoxy, phenyl, 3-6 membered heterocyclyl, 5-6 membered heteroaryl are optionally substituted by -halogen, —CN, hydroxyl, —$C_{1-3}$alkyl, —$C_{1-3}$alkoxyl, $C_{1-3}$alkylamino, di$C_{1-6}$alkylamino, a 3-6 membered heterocyclyl, a 6-10 membered aryl or a 5-10 membered heteroaryl.

13. A compound according to claim 1, wherein $R^{3c}$ is —$C_{1-3}$alkyl, —$S(O)_2$ $C_{1-3}$alkyl and —$C(O)C_{1-3}$alkyl.

14. A compound according to claim 1, wherein $R^{3b}$ is hydrogen, halogen, methyl, ethyl, propyl, isopropyl, isobutyl, methoxyl, cyclopropyl, cyclobutyl, cyclopentyl, cyclohexyl, —$OR^{3c}$, —$NR^{3d}R^{3e}$, $C_{3-10}$cycloalkyl, wherein methyl, ethyl, propyl, isopropyl, isobutyl, cyclopropyl, cyclobutyl, cyclopentyl, cyclohexyl are optionally substituted with 0-3 —$R^{3d}$.

15. A compound according to claim 1, wherein $R^3$ is

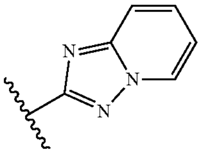, 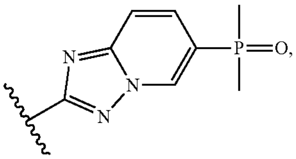,

-continued
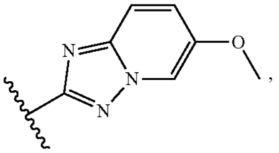
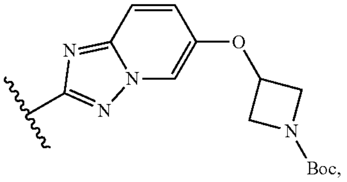
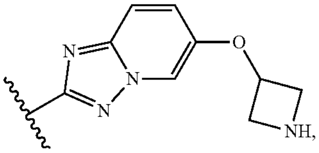
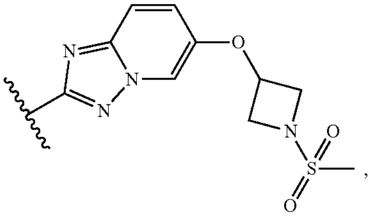
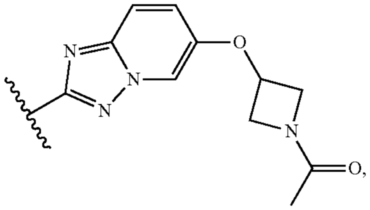
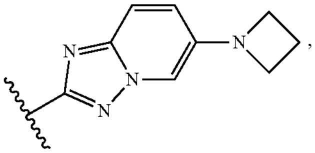
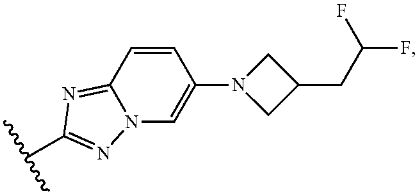
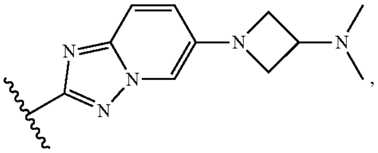
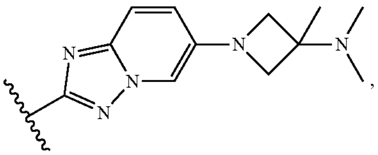
-continued
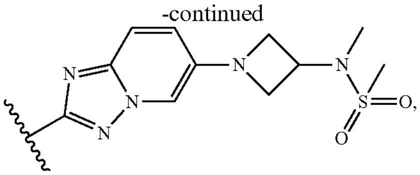
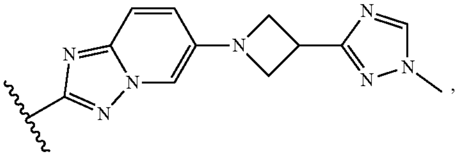
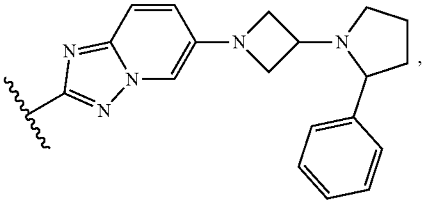
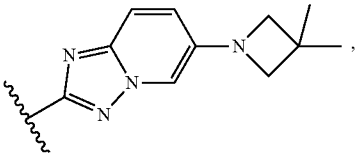
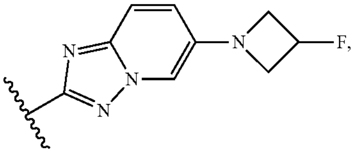
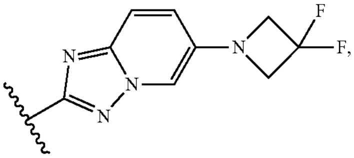
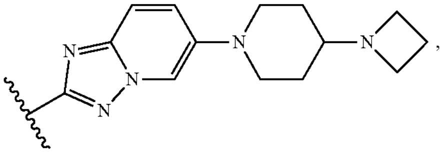
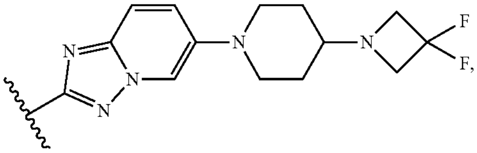
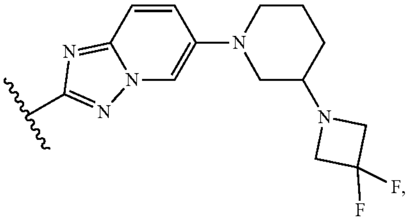
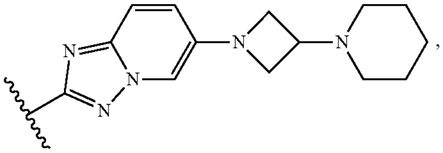

-continued
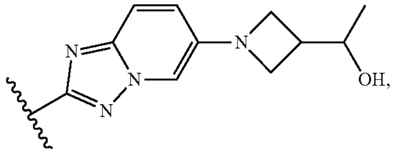
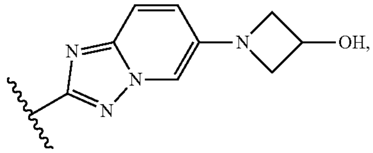
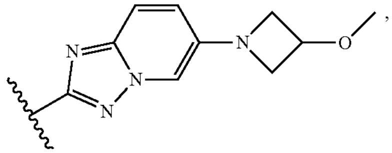
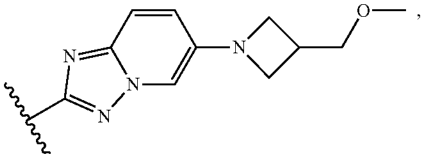
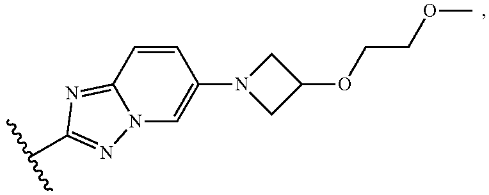
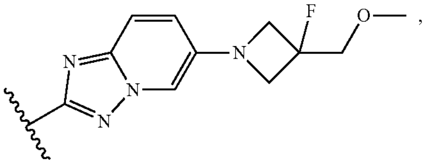
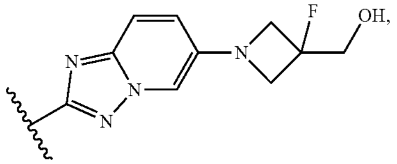
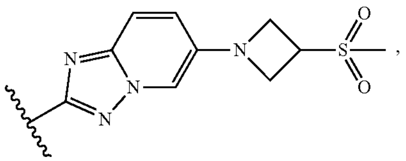
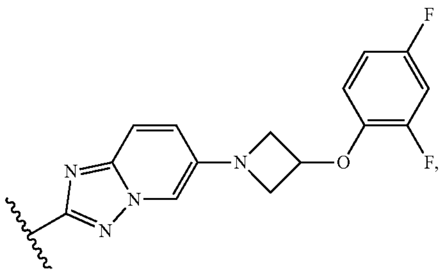
-continued
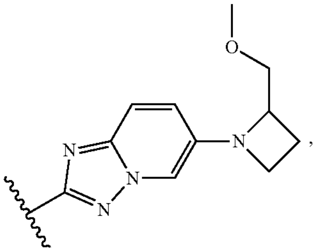
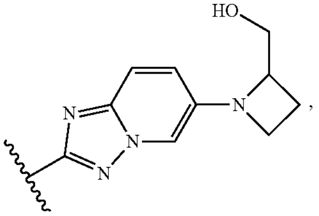
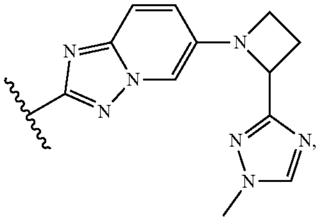
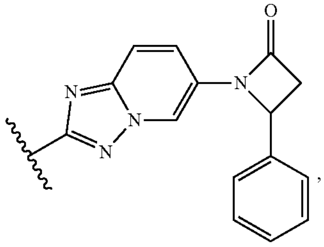
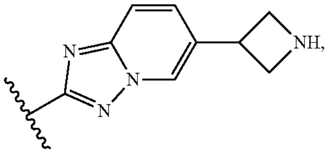
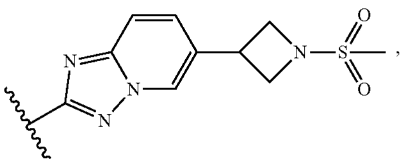
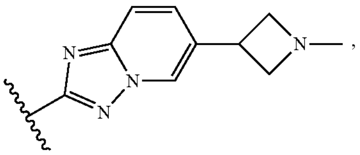
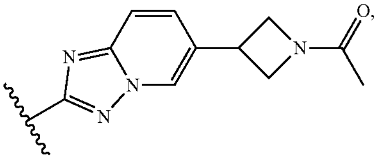

-continued
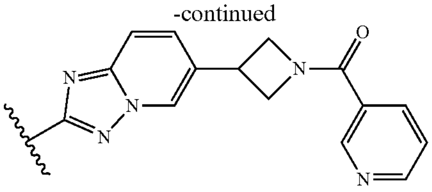
,
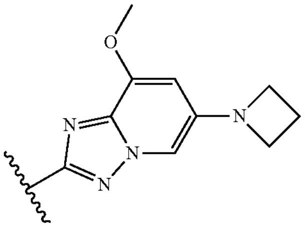
,
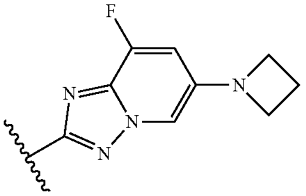
,
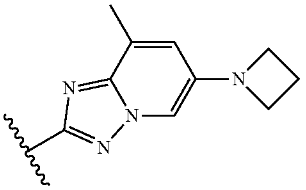
,
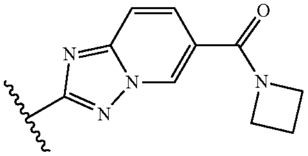
,
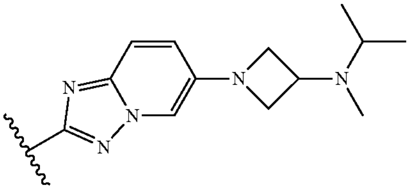
,
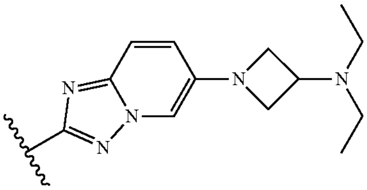
,
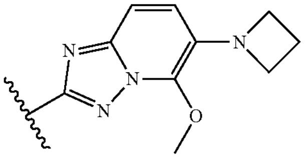
,
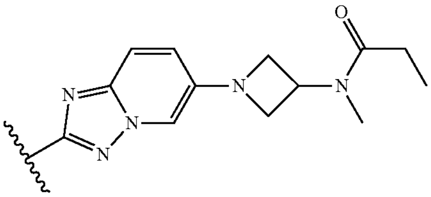
,
-continued
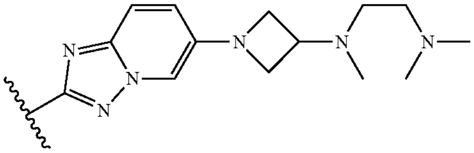
,
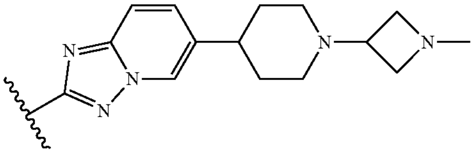
,
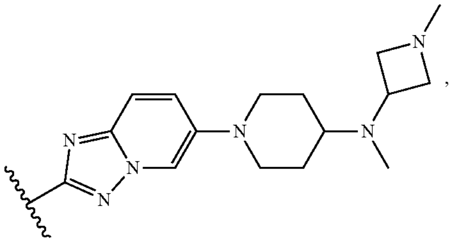
,
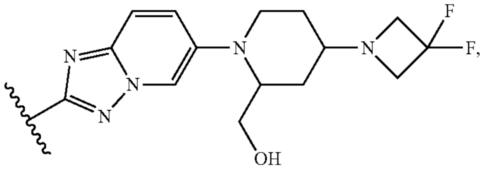
,
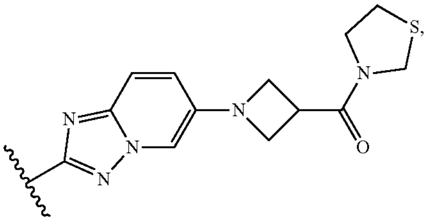
,
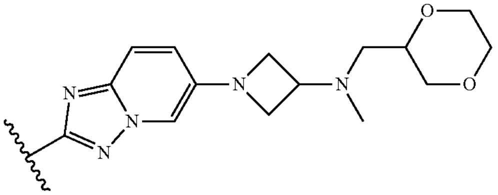
,
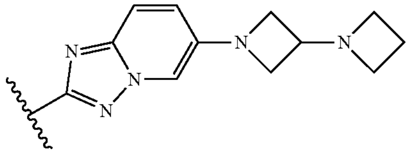
,
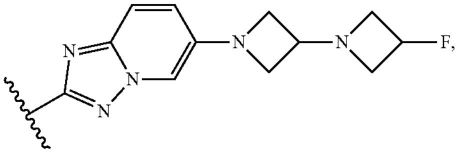
,
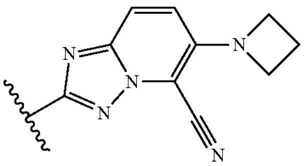
, -continued
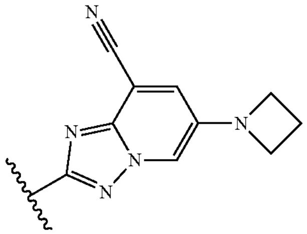,
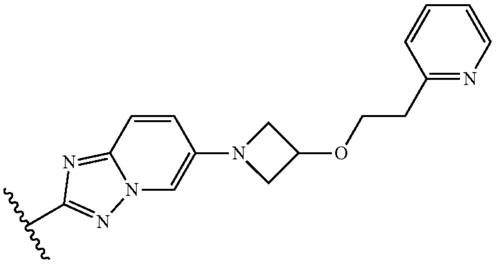,
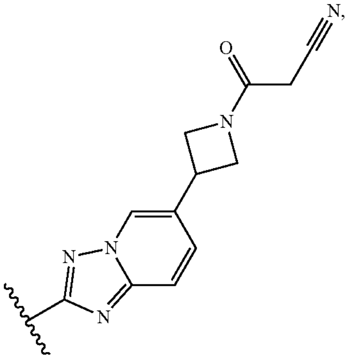,
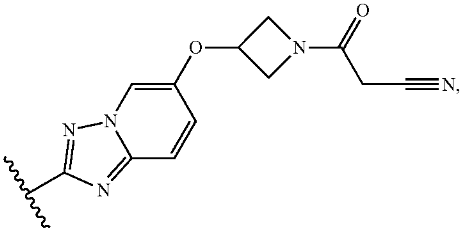,
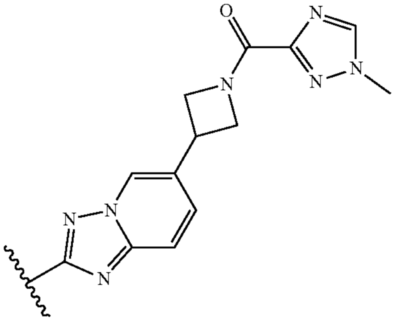,
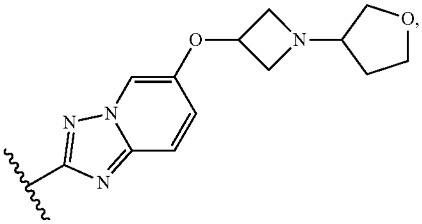,
-continued
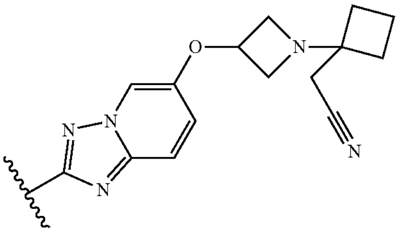,
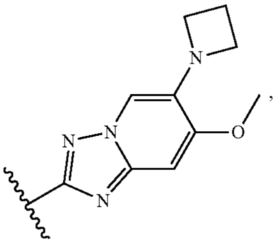,
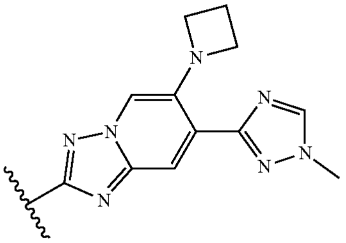, or
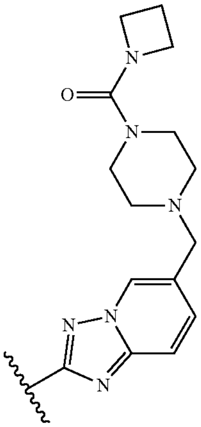.
16. A compound according to claim 1, wherein the compound is selected from the group consisting of
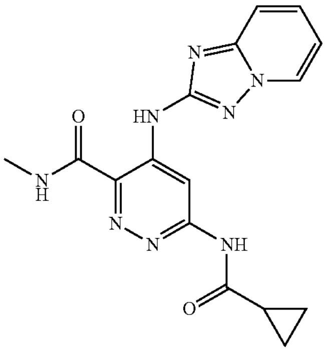, -continued
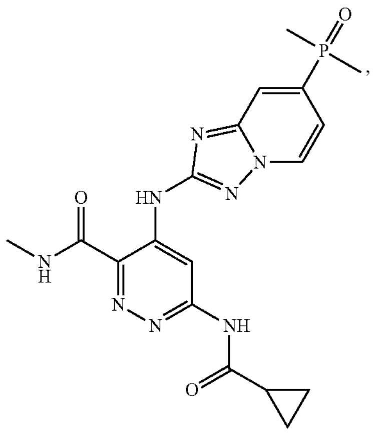
,
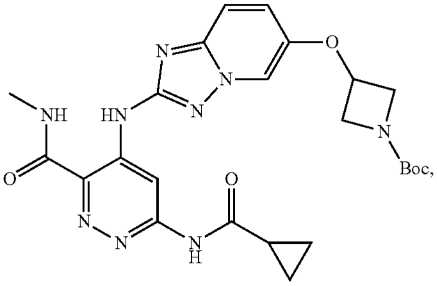
,
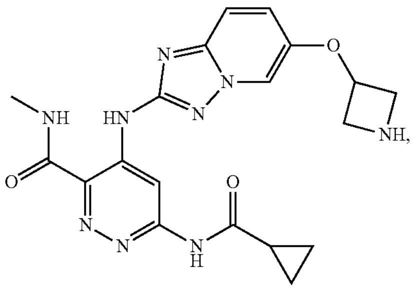
,
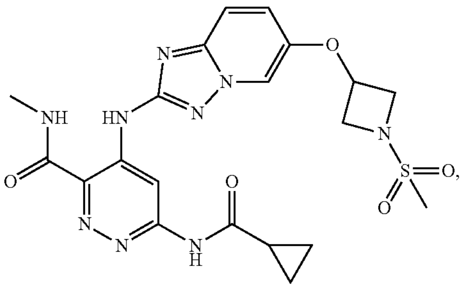
,
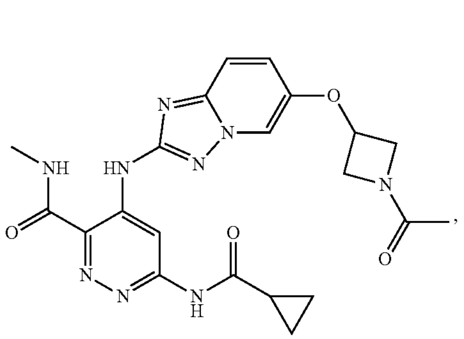
,
-continued
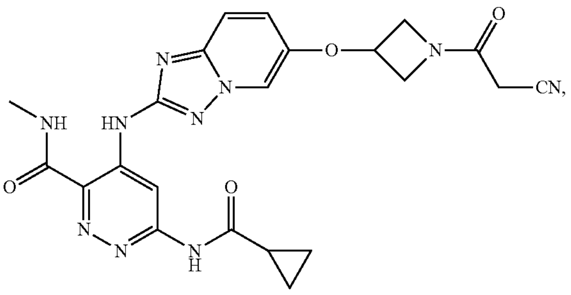
,
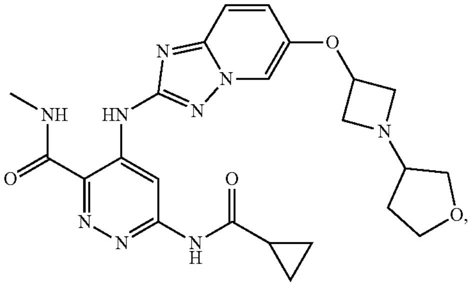
,
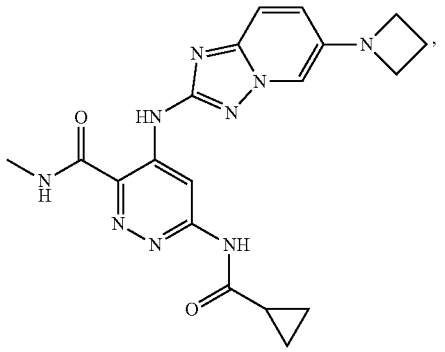
,
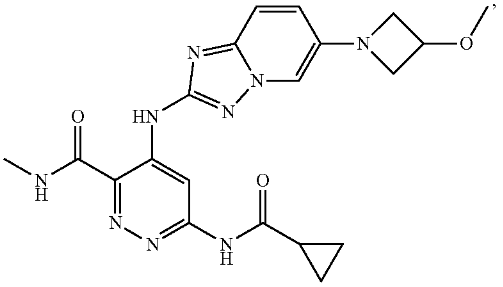
,
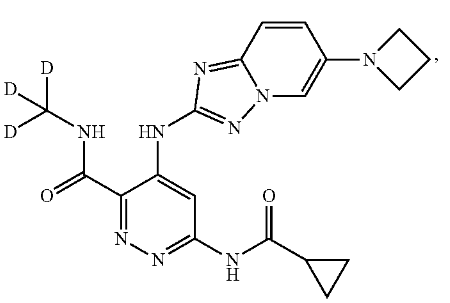
, -continued
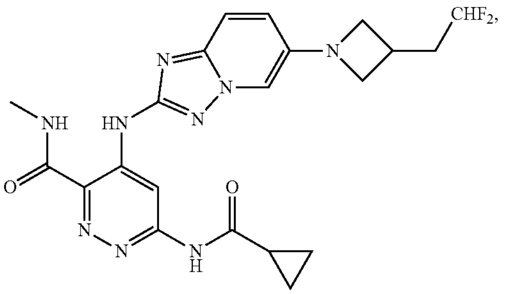
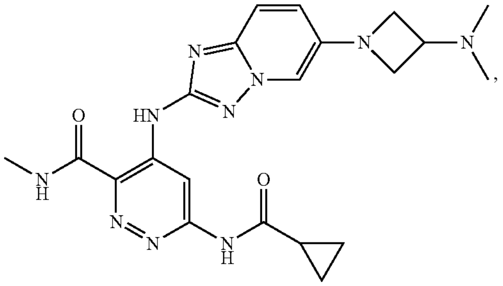
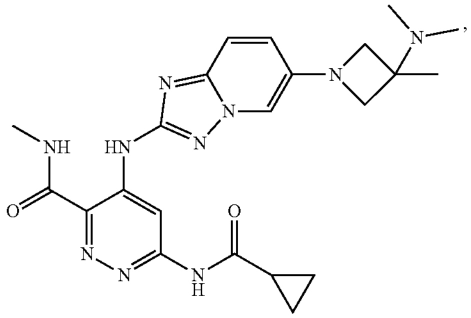
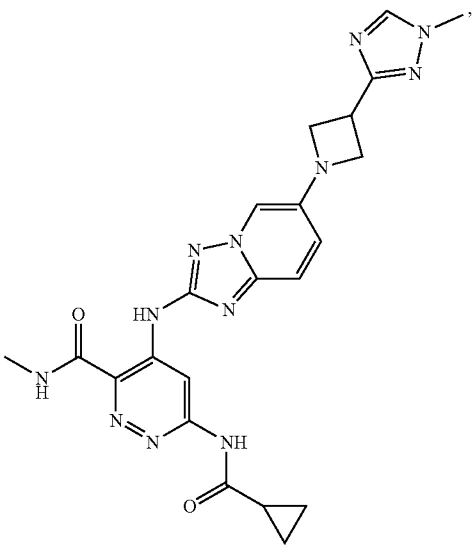
-continued
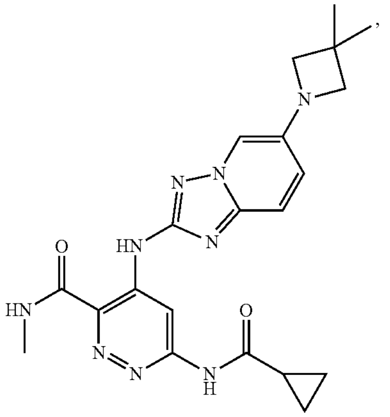
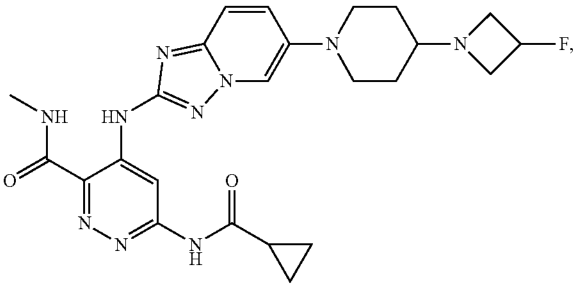 [SMILES: CNC(=O)c1nnc(NC(=O)C2CC2)cc1Nc1nc2ccc(N3CCC(N4CC(F)C4)CC3)cn2n1]
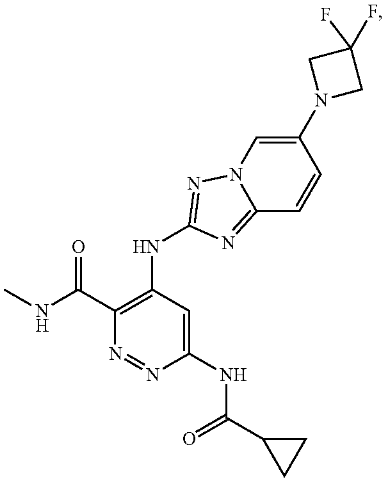
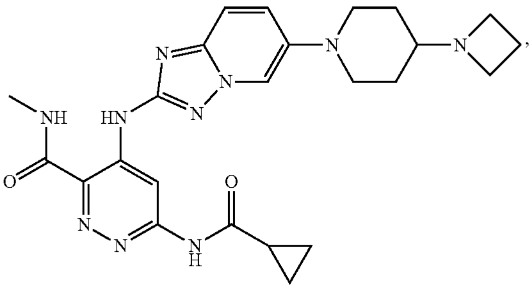

-continued
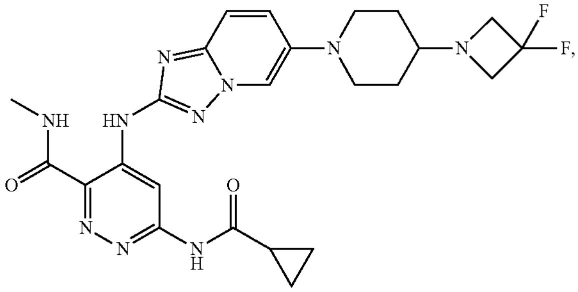
,
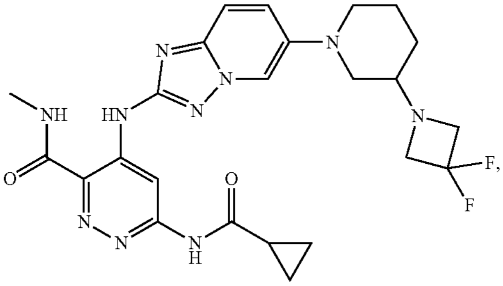
,
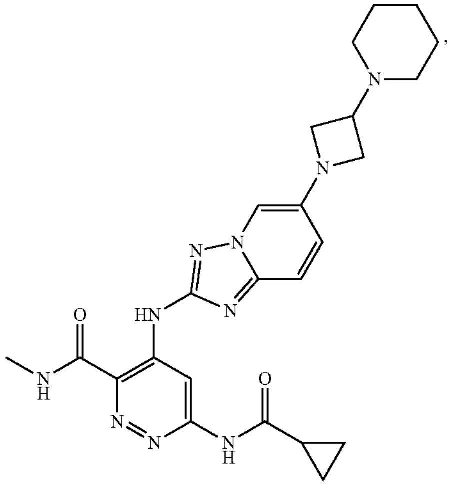
,
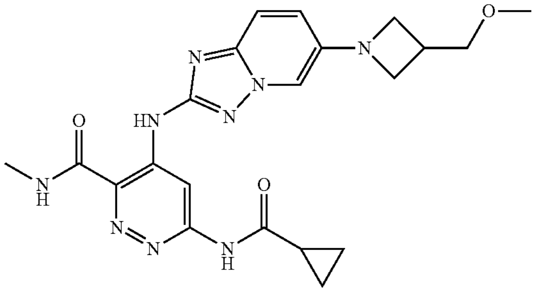
,
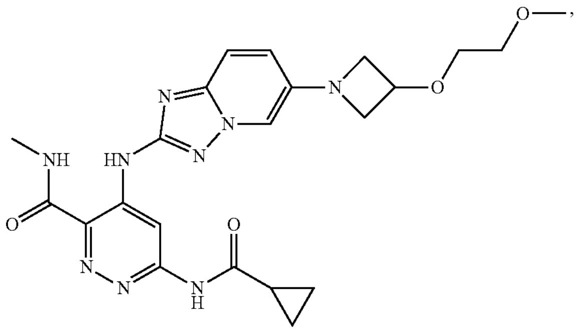
,
-continued
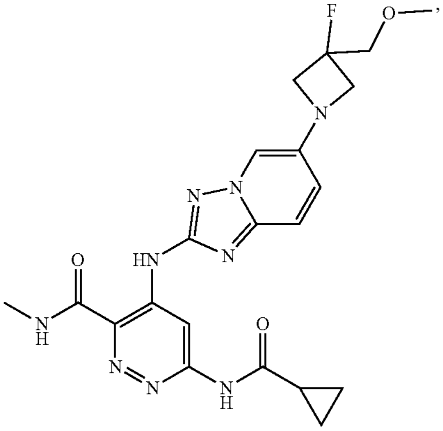
,
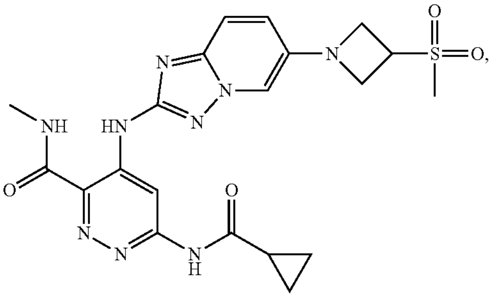
,
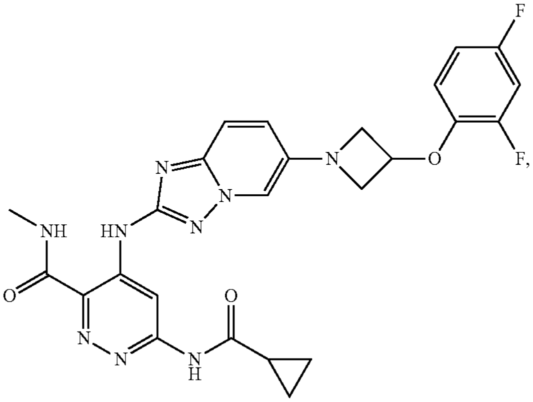
,
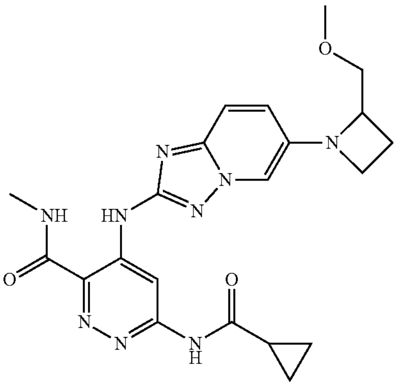
, -continued
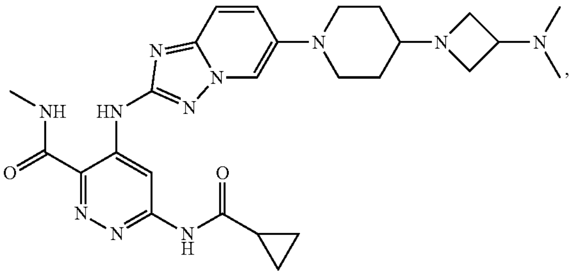
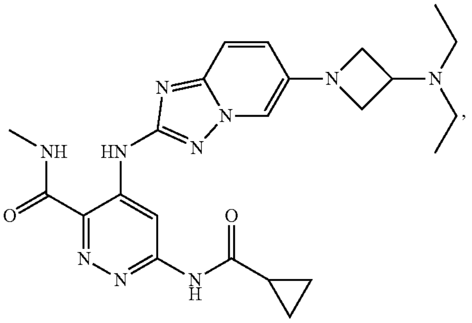
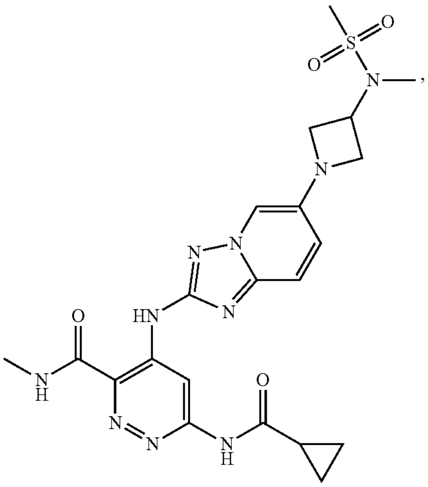
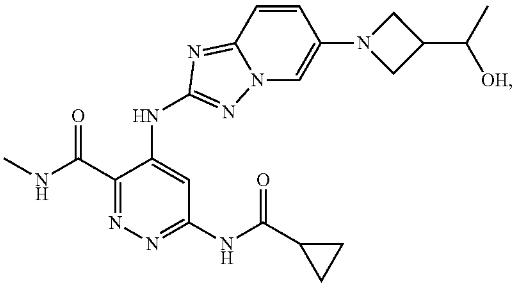
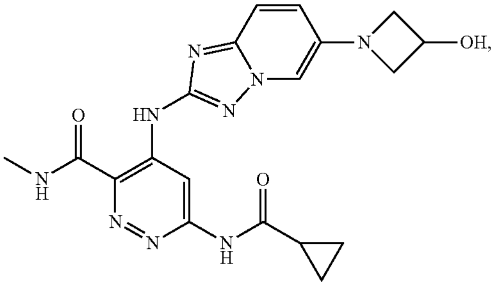
-continued
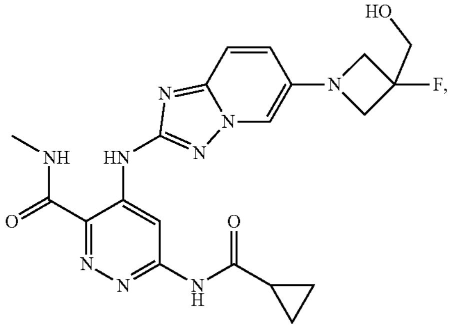
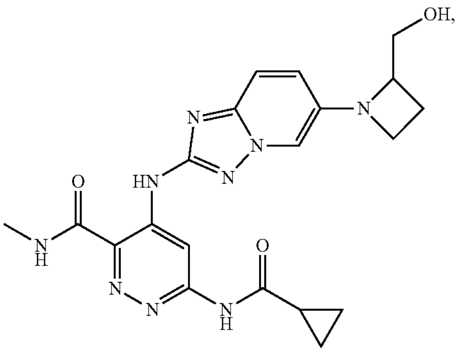
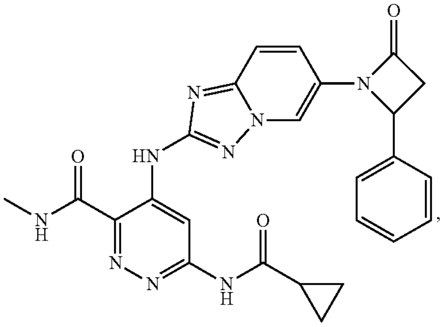
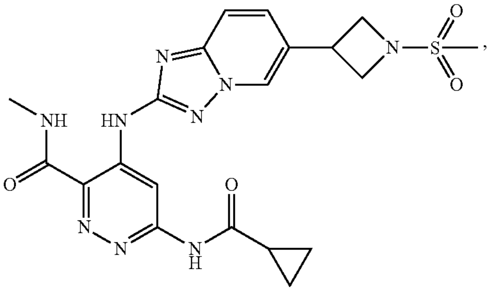
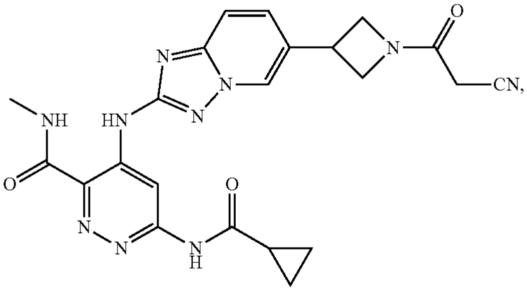

-continued
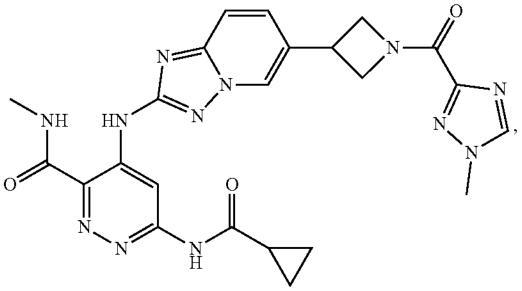
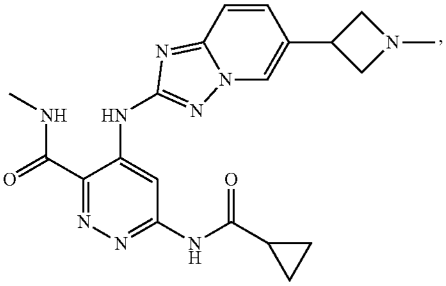
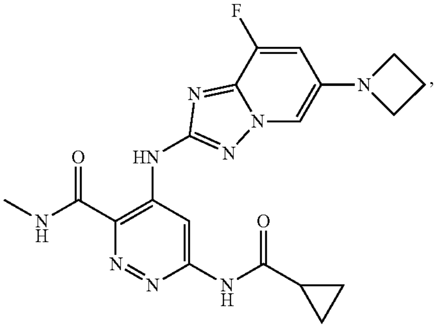
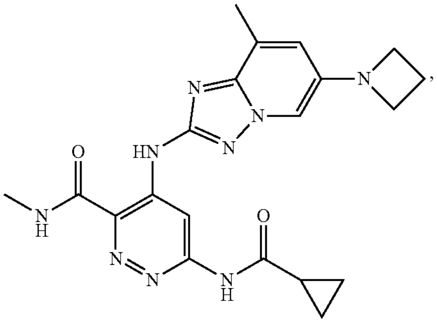
-continued
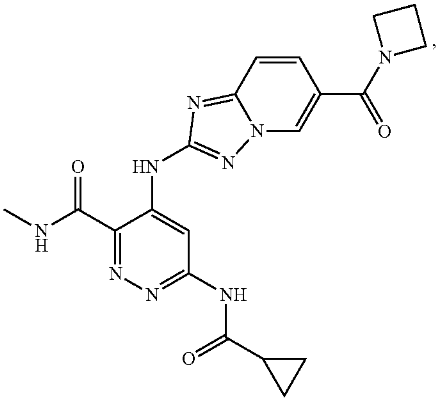
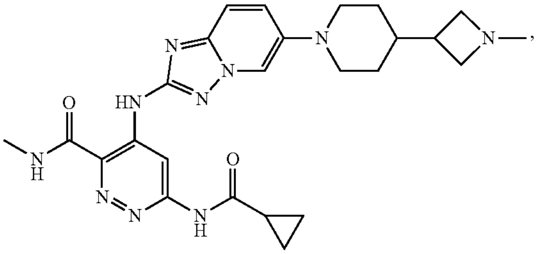
and
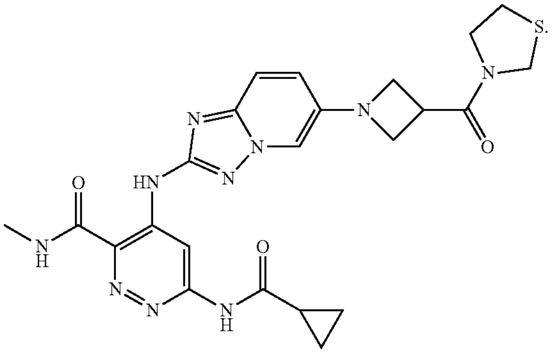
17. A pharmaceutical composition comprising one or more compounds according to claim 1 or a stereoisomer or pharmaceutically acceptable salt thereof, and a pharmaceutically acceptable excipient.
* * * * *